(12) United States Patent
Wang et al.

(10) Patent No.: US 10,457,680 B2
(45) Date of Patent: Oct. 29, 2019

(54) PROCESS FOR PREPARING A PARP INHIBITOR, CRYSTALLINE FORMS, AND USES THEREOF

(71) Applicant: BeiGene, Ltd., Camana Bay, Grand Cayman (KY)

(72) Inventors: Hexiang Wang, Beijing (CN); Changyou Zhou, Princeton, NJ (US); Bo Ren, Beijing (CN); Xianzhao Kuang, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 15/753,993

(22) PCT Filed: Aug. 22, 2016

(86) PCT No.: PCT/CN2016/096200
§ 371 (c)(1),
(2) Date: Feb. 21, 2018

(87) PCT Pub. No.: WO2017/032289
PCT Pub. Date: Mar. 2, 2017

(65) Prior Publication Data
US 2019/0177325 A1   Jun. 13, 2019

(30) Foreign Application Priority Data

Aug. 25, 2015   (WO) ............... PCT/CN2015/088003

(51) Int. Cl.
| | |
|---|---|
| *C07D 487/06* | (2006.01) |
| *C07D 487/22* | (2006.01) |
| *C07D 471/22* | (2006.01) |
| *C07D 471/04* | (2006.01) |
| *A61P 35/04* | (2006.01) |

(52) U.S. Cl.
CPC ............ *C07D 471/22* (2013.01); *A61P 35/04* (2018.01); *C07D 471/04* (2013.01); *C07B 2200/13* (2013.01)

(58) Field of Classification Search
CPC .......................... C07D 487/06; C07D 487/22
See application file for complete search history.

(56) References Cited

U.S. PATENT DOCUMENTS

| | | |
|---|---|---|
| 9,260,440 B2 | 2/2016 | Zhou et al. |
| 9,617,273 B2 | 4/2017 | Zhou et al. |
| 10,112,952 B2 | 10/2018 | Zhou et al. |
| 2016/0222012 A1 | 8/2016 | Ruan |
| 2017/0305921 A1 | 10/2017 | Zhou et al. |
| 2019/0016731 A1 | 1/2019 | Zhou et al. |

FOREIGN PATENT DOCUMENTS

| | | |
|---|---|---|
| JP | 2002-534523 | 10/2002 |
| WO | WO 2000/042040 | 7/2000 |
| WO | WO 2002/044183 | 6/2002 |
| WO | WO 2004/063198 | 7/2004 |
| WO | WO 2010/017055 | 2/2010 |
| WO | WO 2013/097225 | 7/2013 |
| WO | WO 2015/035606 | 3/2015 |
| WO | WO 2016/000619 | 1/2016 |
| WO | WO 2017/032289 | 3/2017 |
| WO | WO 2018/059437 | 4/2018 |
| WO | WO 2018/157794 | 9/2018 |
| WO | WO 2019/015561 | 1/2019 |

OTHER PUBLICATIONS

Supplementary European Search Report for European Application No. 11878508.8, dated Sep. 22, 2015, 3 pages.
International Preliminary Report on Patentability for International Application No. PCT/CN2011/085148, dated Jul. 1, 2014, 7 pages.
International Search Report and Written Opinion for International Application No. PCT/CN2011/085148, dated Sep. 27, 2012, 12 pages.
International Search Report and Written Opinion for International Application No. PCT/CN2016/096200, dated Nov. 11, 2016, 12 pages.
Chen, A., "PARP inhibitors: its role in treatment of cancer," Chinese Journal of Cancer, 2011, vol. 30, Issue 7, pp. 463-471.
Underhill, C. et al., "A review of PARP inhibitors: from bench to bedside," Annals of Oncology, Advance Access published Jul. 19, 2010, doi:10.1093/annonc/mdq322, Retrieved from the Internet: <URL: http://annonc.oxfordjournals.org/>. Retrieved from the Internet on Jun. 14, 2016, 12 pages.
STN International, RN: 1858211-28-5, STN Registry, Feb. 2, 2016, 2 pages.
Extended European Search Report for European Application No. 16838548.2, dated Dec. 19, 2018, 8 pages.
International Search Report and Written Opinion for International Application No. PCT/CN2017/103660, dated Jan. 9, 2018, 11 pages.
International Search Report and Written Opinion for International Application No. PCT/CN2018/077433, dated Jun. 5, 2018, 11 pages.
International Search Report and Written Opinion for International Application No. PCT/CN2018/095911, dated Oct. 26, 2018, 9 pages.
Morissette, S. L., "High-throughput crystallization: polymorphs, salts, co-crystals and solvates of pharmaceutical solids," Advanced Drug Delivery Reviews, vol. 56, No. 3, Feb. 2004, pp. 275-300.
Fujiwara, M. et al., "First-principles and direct design approaches for the control of pharmaceutical crystallization," Journal of Process Control, vol. 15, No. 5, Aug. 2005, pp. 493-504.
Variankaval, N. et al., "From form to function: Crystallization of active pharmaceutical ingredients," AIChE Journal, vol. 54, No. 7, Jul. 2008, pp. 1682-1688.
Caira, M. R., "Crystalline polymorphism of organic compounds," Topics in Current Chemistry, vol. 198, 1998, pp. 163-208.

*Primary Examiner* — Bruck Kifle
(74) *Attorney, Agent, or Firm* — Cooley LLP

(57) ABSTRACT

Provided are a process for preparing a Parp1/2 inhibitor, i.e., (R)-2-fluoro-10a-methyl-7,8,9,10,10a,11-hexahydro-5,6,7a, 11-tetraazacyclohepta[def]cyclopenta[a]fluoren-4(5H)-one (hereinafter referred to as Compound A), crystalline forms (poly-morphs) of Compound A or hydrate or solvate thereof, methods for preparing the crystalline forms, and the use thereof.

23 Claims, 23 Drawing Sheets

PROCESS FOR PREPARING A PARP INHIBITOR, CRYSTALLINE FORMS, AND USES THEREOF

CROSS-REFERENCE TO RELATED APPLICATION

This application is a U.S. National Stage Application under 35 U.S.C. § 371 of International Application No. PCT/CN2016/096200, filed on Aug. 22, 2016, and entitled "PROCESS FOR PREPARING A PARP INHIBITOR, CRYSTALLINE FORMS, AND USES THEREOF", which claims the benefit of International Application No. PCT/CN2015/088003, filed Aug. 25, 2015.

FIELD OF THE INVENTION

The present invention relates to a process for preparing a Parp1/2 inhibitor, i.e., (R)-2-fluoro-10a-methyl-7,8,9,10,10a,11-hexahydro-5,6,7a,11-tetraazacyclohepta[def]cyclopenta[a]fluoren-4(5H)-one (hereinafter referred to as Compound A), crystalline forms (polymorphs) of Compound A or hydrate or solvate thereof, especially crystalline form C of Compound A sesqui-hydrate, methods for preparing the crystalline forms, and the use thereof.

BACKGROUND OF THE INVENTION

One of the hallmarks and driving forces of cancer is genetic instability [Hanahan D and Weinberg R A, Hallmarks of cancer: the next generation. Cell, 2011. 144(5): p. 646-74.]. Specifically in familial cancers, mutations in the breast cancer susceptibility BRCA1 and BRCA2 tumor suppressor genes, key players in homologous recombination (HR), have been associated with an increased risk of developing breast or ovarian cancer [Li X and Heyer W D, Homologous recombination in DNA repair and DNA damage tolerance. Cell Res, 2008. 18(1): p. 99-113.]. It is in this patient population that inhibitors of poly (ADP-ribose) polymerase (PARP) have gained recent attention. PARP family members PARP1 and PARP2 play important roles in DNA replication, transcriptional regulation, and DNA damage repair [Rouleau M, Patel A, Hendzel M J, et al., PARP inhibition: PARP1 and beyond. Nat Rev Cancer, 2010. 10(4): p. 293-301.]. In 2005, two breakthrough Nature papers showed that PARP inhibitors given alone could kill cancer cells with pre-existing DNA repair defects, specifically mutations in BRCA1/2 genes [Bryant H E, Schultz N, Thomas H D, et al., Specific killing of BRCA2-deficient tumours with inhibitors of poly(ADP-ribose) polymerase. Nature, 2005. 434(7035): p. 913-7; Farmer H, McCabe N, Lord C J, et al., Targeting the DNA repair defect in BRCA mutant cells as a therapeutic strategy. Nature, 2005. 434 (7035): p. 917-21].

PARP inhibition and mutant BRCA were synthetically lethal in preclinical models, suggesting an elegant, targeted and minimally toxic way to treat patients.

Testing of PARP inhibitors in the clinic has grown exponentially in the past few years. These clinical trials started with using PARP inhibitors as a single-agent or in the combination with another DNA-damaging agent to treat hereditary tumors, and have now moved on to treating many different types of sporadic tumors. Initial excitement with PARP inhibitors came around when olaparib (AZD2281, KU0059436; AstraZeneca/KuDOS) was found to be active in patients with BRCA-deficient breast, ovarian and prostate cancers [Fong P C, Boss D S, Yap T A, et al., Inhibition of poly(ADP-ribose) polymerase in tumors from BRCA mutation carriers. N Engl J Med, 2009. 361(2): p. 123-34.]. There were minimal adverse events (AEs) in these particular patients and there was no increase in the frequency of AEs in BRCA carriers compared to that in noncarriers. Subsequent proof-of-concept phase II trials in ovarian and breast cancer patients confirmed the responses as well as the low side effect profile of olaparib in this group of BRCA mutant cancer patients [Audeh M W, Carmichael J, Penson R T, et al., Oral poly(ADP-ribose) polymerase inhibitor olaparib in patients with BRCA1 or BRCA2 mutations and recurrent ovarian cancer: a proof-of-concept trial. Lancet, 2010. 376 (9737): p. 245-51; Tuft A, Robson M, Garber J E, et al., Oral poly(ADP-ribose) polymerase inhibitor olaparib in patients with BRCA1 or BRCA2 mutations and advanced breast cancer: a proof-of-concept trial. Lancet, 2010. 376(9737): p. 235-44.]

Interestingly, response of ovarian cancer patients carrying BRCA1/2 mutations to PARP inhibitors was associated with their sensitivity to prior platinum treatment [Fong P C, Yap T A, Boss D S, et al., Poly(ADP)-ribose polymerase inhibition: frequent durable responses in BRCA carrier ovarian cancer correlating with platinum-free interval. J Clin Oncol, 2010. 28(15): p. 2512-9.]. Similar correlation with platinum-sensitivity was also seen in high-grade serous ovarian cancer patients without BRCA mutations [Gelmon K A, Tischkowitz M, Mackay H, et al., Olaparib in patients with recurrent high-grade serous or poorly differentiated ovarian carcinoma or triple-negative breast cancer: a phase 2, multicentre, open-label, non-randomised study. Lancet Oncol, 2011. 12(9): p. 852-61.]. Another phase II clinical study has shown that olaparib as maintenance therapy was beneficial in patients with relapsed, high-grade serous ovarian cancer, who were sensitive to platinum [Ledermann J, Harter P, Gourley C, et al., Olaparib maintenance therapy in platinum-sensitive relapsed ovarian cancer. N Engl J Med, 2012. 366(15): p. 1382-92.]. Based on these data, phase III registration trials have been initiated for olaparib in breast and ovarian cancer patients.

In a recent phase II study, olaparib demonstrated good clinical activity when given in combination with paclitaxel in patients with recurrent and metastatic gastric cancer who progressed following first-line therapy [Bang Y-J, Im S-A, Lee K-W, et al., Olaparib plus paclitaxel in patients with recurrent or metastatic gastric cancer: A randomized, double-blind phase II study. J Clin Oncol, 2013. 31(suppl; abstr 4013).]. Eligible patients were stratified by their ataxia-telangiectasia mutated (ATM) status. Paclitaxel/olaparib combination extended patient's overall survival (OS) compared to paclitaxel single agent, especially in ATM-low sub-group. ATM is a serine/threonine protein kinase that plays a critical role in DNA damage induced signalling and the initiation of cell cycle checkpoint in response to DNA-damaging agents such as ionizing radiation [Stracker T H, Roig I, Knobel P A, et al., The ATM signaling network in development and disease. Front Genet, 2013. 4: p. 37.].

On Dec. 19, 2014, the U.S. Food and Drug Administration approved olaparib capsules (Lynparza, AstraZeneca Pharmaceuticals LP) as monotherapy for the treatment of patients with deleterious or suspected deleterious germline BRCA mutated (gBRCAm) (as detected by an FDA-approved test) advanced ovarian cancer who have been treated with three or more prior lines of chemotherapy. Concurrent with this action, FDA approved the BRACAnalysis CDx (Myriad Genetics) for the qualitative detection and classification of variants in the BRCA1 and BRCA2 genes.

There are several other investigational PARP inhibitors in the clinic, including veliparib (ABT-888; Abbott Laboratories), rucaparib (AG014669; Clovis), niraparib (MK-4827; Tesaro), BMN-673 (Biomarin), CEP-9722 (Cephalon), and E7016 (Eisai). All these PARP inhibitors are different in their potency, selectivity, and DNA trapping activity. A recent report suggests that DNA trapping by PARP-inhibitor complex is one of the major mechanisms by which PARP inhibitors induce cytotoxicity in cells [Murai J, Huang S Y, Das B B, et al., Trapping of PARP1 and PARP2 by Clinical PARP Inhibitors. Cancer Res, 2012. 72(21): p. 5588-99.]. Veliparib is a potent PARP1/2 inhibitor but with weak DNA trapping activity and cellular cytotoxicity in BRCA mutant cells. Most of its clinical development has been focused on combination with chemotherapeutics. Recently, it was shown in a phase II trial that adding combination of veliparib plus carboplatin to standard neoadjuvant chemotherapy improved outcomes for women with triple-negative breast cancer [Rugo H, Olopade O, DeMichele A, et al., Veliparib/carboplatin plus standard neoadjuvant therapy for high-risk breast cancer: First efficacy results from the I-SPY 2 TRIAL. 2013. Abstract S5-02.]. For rucaparib, niraparib, and BMN-673, monotherapy has demonstrated good clinical activity in BRCA mutant cancer patients [Shapiro G, Kristeleit R, Middleton M, et al., Pharmacokinetics of orally administered rucaparib in patients with advanced solid tumors. Mol Cancer Ther, 2013. 12(11 Suppl): Abstract nr A218; Michie C O, Sandhu S K, Schelman W R, et al., Final results of the phase I trial of niraparib (MK4827), a poly(ADP)ribose polymerase (PARP) inhibitor incorporating proof of concept biomarker studies and expansion cohorts involving BRCA1/2 mutation carriers, sporadic ovarian, and castration resistant prostate cancer (CRPC). J Clin Oncol, 2013. 31(suppl; abstr 2513); Bono J S D, Mina L A, Gonzalez M, et al., First-in-human trial of novel oral PARP inhibitor BMN 673 in patients with solid tumors. J Clin Oncol, 2013. 31(suppl; abstr 2580)].

Phase III trials for these PARP inhibitors are currently underway in breast and/or ovarian cancer patients with BRCA mutation or platinum sensitive disease.

(R)-2-fluoro-10a-methyl-7,8,9,10,10a,11-hexahydro-5,6,7a,11-tetraazacyclohepta[def]cyclopenta[a]fluoren-4(5H)-one (or "Compound A") is a highly selective PARP1/2 inhibitor. Compound A potently inhibits intracellular PARP activity and specifically inhibits the proliferation of cell lines with BRCA1/2 mutations or other HR deficiencies. Compound A significantly induces tumor regression in BRCA1 mutation breast cancer xenograft model at much lower dose than olaparib. Compound A has excellent DMPK properties and significant brain penetration.

Data generated in preclinical biochemical, cell-based and animal studies suggest that Compound A could offer significant patient benefit in inhibiting tumors harboring BRCA gene mutations or homologous recombination defects. It has good brain penetration and might show activity in more indication such as glioblastoma. These unique characteristics warrant further evaluation of Compound A in clinical studies.

The free base, i.e., (R)-2-fluoro-10a-methyl-7,8,9,10,10a, 11-hexahydro-5,6,7a,11-tetraazacyclohepta[def]cyclopenta[a]fluoren-4(5H)-one (or "Compound A") has been disclosed as a highly selective and potent Parp1/2 inhibitor, See WO 2013/097225 A1 which is incorporated herein by reference.

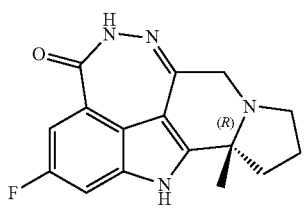

Compound A

Compound A is a multiple ring-fused complex molecule with a quarterly chiral center. Compound A in a free base form was obtained originally through "chiral pool" method which was extremely inefficient and difficult for scale-up because multiple chromatography columns were needed for the purification of the intermediates and the final product. In addition, Compound A prepared in such a way has unsatisfactory optical purity because the partial racemization occurred during manufacturing process (although the underlining reasons remain uncertain). Therefore, there is a great need for a process suitable for large-scale preparation of Compound A (especially crystalline forms thereof) with reproducibility and good quality for formulation development.

SUMMARY OF THE INVENTION

The disclosure of the present application addresses the foregoing challenges and need.

In the first aspect, the present application provides a large scale process for preparing Compound A in free base form, which avoids the use of multiple chromatography columns for the purification of the intermediates and the final product and is therefore cost-effective and of commercial benefit.

In the second aspect, the present application provides crystalline forms of Compound A or hydrate thereof or solvate thereof, which have superior physical properties suitable for pharmaceutical formulations and that can be manufactured on large commercial scales in high quality and good reproducibility.

The inventors unexpectedly and surprisingly discovered that the free base of Compound A can form hydrates and/or solvates, in particular sesqui-hydrate, in crystalline forms. In particular, it was surprisingly discovered that Compound A free base hydrates/solvates can exist in a number of crystalline forms (polymorphs), which are herein referred to as Crystalline Forms A, B, C, C*, C**, D, E, F, G, H, I, J, K and L. The crystalline forms of Compound A free base and the hydrate/solvate thereof, specifically Crystalline Form C, have superior properties, such as excellent chemical stability, particularly the long-term chemical/physical stability, to those of other solvates screened, which make it suitable API candidates for formulation and clinical application. Crystalline Form C (i.e., Compound A Sesqui-Hydrate) has low solubility in water (~0.04 mg/mL). This low solubility in water simplifies the large scale process of API manufacture because recrystallization and slurry of API can be done in water/alcohol solution. Quite surprisingly, its solubility in low pH aqueous medium, such as simulated gastric fluid (SGF, e.g., ~4.5 mg/mL, pH=1.2), is such that a fast dissolution in stomach is possible and a good drug absorption can be achieved in animals and human. The low solubility and high crystalline stability in water also make Compound A Sesqui-Hydrate Crystalline Form C specifically suitable for wet granulating and coating processes in drug product manufacture.

Thus, in one aspect the present invention provides a compound of Formula I, which is a hydrate/solvate of Compound A:

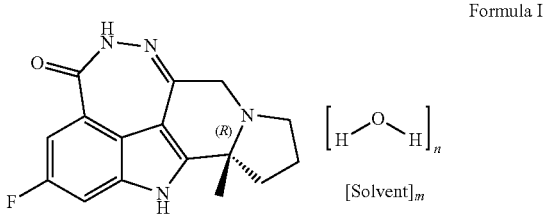

Formula I wherein n is a number from about 0.0 to about 2.0; m is a number from about 0.0 to about 20.0; and wherein the solvent is isopropanol, ethanol, methanol, acetone, THF, 1,4-dioxane, acetic acid, acetonitrile, water, or a combination thereof.

In another embodiment, the present invention provides a compound of Formula II, which is a hydrate of Compound A:

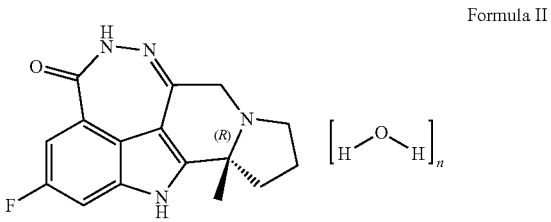

Formula II wherein n is a number from about 0.0 to about 2.0.

In another preferred embodiment, the compound of Formula II is in a crystalline form.

In another preferred embodiment, n is about 1.5, and the compound is a crystalline sesqui-hydrate of (R)-2-fluoro-10a-methyl-7,8,9,10,10a,11-hexahydro-5,6,7a,11-tetraaza-cyclohepta[def]cyclopenta[a]fluoren-4(5H)-one of Formula III:

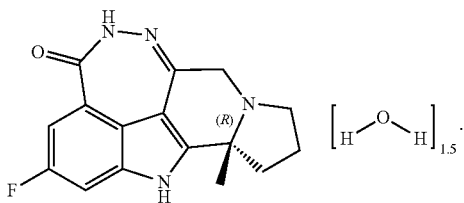

Formula III

In another embodiment, the compound of Formula II is in Crystalline Form A, which is characterized by a powder X-ray diffraction pattern comprising three, four, five, six, seven, eight, nine, or more diffraction peaks having 2θ angle values independently selected from the group consisting of: 6.3±0.2, 8.5±0.2, 8.6±0.2, 9.9±0.2, 10.4±0.2, 11.0±0.2, 11.1±0.2, 12.6±0.2, 12.8±0.2, 14.7±0.2, 18.0±0.2, 18.1±0.2, 20.1±0.2, 21.4±0.2, 22.2±0.2, 24.6±0.2, 25.7±0.2, and 30.0±0.2 degrees.

In another embodiment, the compound of Formula II is in Crystalline Form B, which is characterized by a powder X-ray diffraction pattern comprising three, four, five, six, seven, or more diffraction peaks having 2θ angle values independently selected from the group consisting of: 6.3±0.2, 8.7±0.2, 11.1±0.2, 12.6±0.2, 14.5±0.2, 14.8±0.2, 15.2±0.2, 18.0±0.2, 23.9±0.2, 25.3±0.2, and 25.8±0.2 degrees.

In another embodiment, the compound of Formula II is in Crystalline Form C, which is characterized by a powder X-ray diffraction pattern comprising three, four, five, six, seven, eight, nine, or more diffraction peaks having 2θ angle values independently selected from the group consisting of: 5.3±0.2, 6.3±0.2, 6.5±0.2, 6.9±0.2, 8.7±0.2, 10.6±0.2, 11.1±0.2, 11.6±0.2, 12.6±0.2, 13.1±0.2, 13.7±0.2, 14.4±0.2, 14.8±0.2, 15.1±0.2, 15.9±0.2, 16.2±0.2, 17.3±0.2, 18.0±0.2, 18.7±0.2, 19.0±0.2, 19.4±0.2, 20.2±0.2, 20.6±0.2, 21.0±0.2, 2±0.2, 21.5±0.2, 22.3±0.2, 22.7±0.2, 23.4±0.2, 23.8±0.2, 24.3±0.2, 24.7±0.2, 25.3±0.2, 25.7±0.2, 26.1±0.2, 26.4±0.2, 27.4±0.2 degrees.

In another embodiment, the compound of Formula II is in Crystalline Form C*, which is characterized by a powder X-ray diffraction pattern comprising three, four, five, six, seven, eight, nine, or more diffraction peaks having 2θ angle values independently selected from the group consisting of: 6.1±0.2, 6.3±0.2, 6.9±0.2, 8.5±0.2, 11.1±0.2, 11.6±0.2, 13.2±0.2, 14.5±0.2, 15.2±0.2, 16.3±0.2, 18.1±0.2, 20.3±0.2, 22.5±0.2, 24.8±0.2, 26.1±0.2, 26.6±0.2, and 27.7±0.2 degrees.

In another embodiment, the compound of Formula II is in Crystalline Form D, which is characterized by a powder X-ray diffraction pattern comprising three, four, five, six, seven, eight, nine, or more diffraction peaks having 2θ angle values independently selected from the group consisting of: 5.7±0.2, 6.4±0.2, 6.8±0.2, 9.3±0.2, 9.8±0.2, 10.3±0.2, 11.5±0.2, 12.4±0.2, 12.9±0.2, 13.4±0.2, 13.9±0.2, 17.8±0.2, 18.3±0.2, 18.8±0.2, 18.9±0.2, 23.7±0.2, 25.0±0.2, 25.7±0.2, 25.9±0.2, and 26.7±0.2 degrees.

In another embodiment, the compound of Formula II is in Crystalline Form E, which is characterized by a powder X-ray diffraction pattern comprising three, four, five, six, seven, eight, nine, or more diffraction peaks having 2θ angle values independently selected from the group consisting of: 6.2±0.2, 8.6±0.2, 9.5±0.2, 11.0±0.2, 11.5±0.2, 12.0±0.2, 12.5±0.2, 13.4±0.2, 13.8±0.2, 14.4±0.2, 14.7±0.2, 15.1±0.2, 15.3±0.2, 16.2±0.2, 16.9±0.2, 17.9±0.2, 18.3±0.2, 19.0±0.2, 19.5±0.2, 20.1±0.2, 21.3±0.2, 22.2±0.2, 22.9±0.2, 23.3±0.2, 24.2±0.2, 24.6±0.2, 25.1±0.2, 25.7±0.2, 26.3±0.2, 27.0±0.2, 27.4±0.2, and 30.9±0.2 degrees.

In another embodiment, the compound of Formula II is in Crystalline Form F, which is characterized by a powder X-ray diffraction pattern comprising three, four, five, six, seven, eight, nine, or more diffraction peaks having 2θ angle values independently selected from the group consisting of: 5.2±0.2, 6.3±0.2, 7.7±0.2, 9.7±0.2, 10.4±0.2, 11.8±0.2, 13.7±0.2, 15.6±0.2, 17.5±0.2, 18.0±0.2, 19.5±0.2, 20.2±0.2, 21.7±0.2, 23.1±0.2, 24.7±0.2, 25.3±0.2, and 27.3±0.2 degrees.

In another embodiment, the compound of Formula II is in Crystalline Form G, which is characterized by a powder X-ray diffraction pattern comprising three, four, five, or more diffraction peaks having 2θ angle values independently selected from the group consisting of: 6.3±0.2, 8.6±0.2, 9.6±0.2, 10.3±0.2, 11.0±0.2, 12.6±0.2, 17.5±0.2, and 25.4±0.2 degrees.

In another embodiment, the compound of Formula II is in Crystalline Form H, which is characterized by a powder X-ray diffraction pattern comprising three, four, five, six, seven, eight, nine, or more diffraction peaks having 2θ angle values independently selected from the group consisting of:

9.5±0.2, 12.0±0.2, 13.5±0.2, 15.4±0.2, 17.0±0.2, 19.0±0.2, 23.0±0.2, 24.2±0.2, 27.0±0.2, 27.4±0.2, 31.0±0.2, 34.7±0.2, and 34.8±0.2 degrees.

In another embodiment, the compound of Formula II is in Crystalline Form I, which is characterized by a powder X-ray diffraction pattern comprising three, four, five, six, seven, eight, nine, or more diffraction peaks having 2θ angle values independently selected from the group consisting of: 9.8±0.2, 10.0±0.2, 11.1±0.2, 11.7±0.2, 12.9±0.2, 13.3±0.2, 13.9±0.2, 14.4±0.2, 17.1±0.2, 17.4±0.2, 17.6±0.2, 17.9±0.2, 18.4±0.2, 18.5±0.2, 19.4±0.2, 20.8±0.2, 21.9±0.2, 23.7±0.2, 26.4±0.2, 26.9±0.2, and 29.4±0.2 degrees.

In another embodiment, the compound of Formula II is in Crystalline Form J, which is characterized by a powder X-ray diffraction pattern comprising three, four, five, six, seven, eight, nine, or more diffraction peaks having 2θ angle values independently selected from the group consisting of: 6.4±0.2, 8.7±0.2, 9.9±0.2, 10.3±0.2, 11.7±0.2, 12.8±0.2, 13.9±0.2, 18.1±0.2, 19.3±0.2, 23.0±0.2, 23.8±0.2, and 25.8±0.2 degrees.

In another embodiment, the compound of Formula II is in Crystalline Form K, which is characterized by a powder X-ray diffraction pattern comprising three, four, five, six, seven, or more diffraction peaks having 2θ angle values independently selected from the group consisting of: 6.4±0.2, 10.8±0.2, 12.6±0.2, 12.8±0.2, 19.2±0.2, 25.2±0.2, 25.8±0.2, 32.4±0.2, and 34.1±0.2 degrees.

In another embodiment, the compound of Formula II is in Crystalline Form L, which is characterized by a powder X-ray diffraction pattern comprising three, four, or more diffraction peaks having 2θ angle values independently selected from the group consisting of: 6.8±0.2, 17.8±0.2, 20.6±0.2, 23.4±0.2, and 27.6±0.2 degrees.

In another embodiment, the compound of Formula II is in a crystalline form substantially characterized by a powder X-ray diffraction pattern selected from the group consisting of FIGS. 5, 6, 7A, 7B, 8, 9, 10, 11, 12, 13, 14, 15, and 16.

In another aspect, the present invention provides a method for preparing a crystalline form of Compound A sesqui-hydrate of Formula III, comprising any one of the following steps:

(a) dissolving free base of (R)-2-fluoro-10a-methyl-7,8,9,10,10a,11-hexahydro-5,6,7a,11-tetraazacyclohepta[def]cyclopenta[a]fluoren-4(5H)-one in a solvent or solvent mixture to form a solution or suspension; and precipitating out (R)-2-fluoro-10a-methyl-7,8,9,10,10a,11-hexahydro-5,6,7a,11-tetraazacyclohepta[def]cyclopenta[a]fluoren-4(5H)-one sesqui-hydrate in a target crystalline form;

(b) dissolving or suspending (R)-2-fluoro-10a-methyl-7,8,9,10,10a,11-hexahydro-5,6,7a,11-tetraazacyclohepta[def]cyclopenta[a]fluoren-4(5H)-one sesqui-hydrate in a solvent or solvent mixture; and precipitating out (R)-2-fluoro-10a-methyl-7,8,9,10,10a,11-hexahydro-5,6,7a,11-tetraazacyclohepta[def]cyclopenta[a]fluoren-4(5H)-one solvates/hydrates in a target crystalline form;

(c) storing a crystalline (R)-2-fluoro-10a-methyl-7,8,9,10,10a,11-hexahydro-5,6,7a,11-tetraazacyclohepta[def]cyclopenta[a]fluoren-4(5H)-one hydrate/solvate for an extended period to obtain a target crystalline form;

(d) heating a crystalline (R)-2-fluoro-10a-methyl-7,8,9,10,10a,11-hexahydro-5,6,7a,11-tetraazacyclohepta[def]cyclopenta[a]fluoren-4(5H)-one hydrate/solvate to an elevated temperature, and cooling the hydrate to obtain a target crystalline form; and (e) exposing a crystalline (R)-2-fluoro-10a-methyl-7,8,9,10,10a,11-hexahydro-5,6,7a,11-tetraazacyclohepta[def]cyclopenta[a]fluoren-4(5H)-one hydrate/solvate to a vapor of a solvent to obtain a target crystalline form.

In one embodiment of this aspect, the free base of Compound A is optionally reacted with a resolving agent (such as a chiral acid, e.g., (+)-di-p-methylbenzoyl-D-tartaric acid) in an appropriate solvent (such as, alcohol, further such as isopropyl alcohol) in the presence of an alkaline before Step (a).

In one embodiment of this aspect, Step (a) or (b) further comprises one or more Steps independently selected from heating, filtering to remove undissolved impurities, distilling solvent, adding a counter solvent or solvent mixture, adding crystal seeds, adding precipitation inducing agent(s), cooling, precipitating, and filtering to collect the crystalline product.

In another embodiment of this aspect, Step (a) or (b), wherein the solvent or solvent mixture is selected from the group consisting of water, lower alkyl alcohols, ketones, ethers, esters, lower aliphatic carboxylic acids, lower aliphatic nitriles, optionally halogenated aromatic solvents, and combinations thereof.

In another embodiment of this aspect, in Step (a) or (b) the solvent is isopropanol, ethanol, methanol, acetone, THF, 1,4-dioxane, acetic acid, acetonitrile, water, or a combination thereof.

In another embodiment of this aspect, in Step (a) the solvent is a mixture of water and any one of isopropanol, ethanol, methanol, acetone, THF, 1,4-dioxane, acetic acid, or acetonitrile. In further embodiment of this aspect, in Step (a), the solvent is a mixture of water and isopropanol.

In another embodiment of this aspect, in Step (a) the free base is an isolated and purified free base, an isolated but unpurified free base, or a crude reaction product containing the free base.

In another embodiment of this aspect, in Step (c) the extended period is at least three days, at least one week, or at least two weeks.

In another embodiment of this aspect, in Step (d) the elevated temperature is at least 40° C., at least 60° C., at least 80° C., or at least 100° C., but lower than decomposition temperature of the sesqui-hydrate.

In another embodiment of this aspect, in Step (e) the vapor is a vapor of acetic acid.

In another embodiment of this aspect, the method is selected from:

1) Step (a) or (b) using isopropanol-water (v/v=20/40) as the solvent to produce Crystalline Form C**;

2) Step (a) or (b) using MTBE as the solvent to produce Crystalline Form B;

3) Step (a) or (b) using i-PrOH/H$_2$O as the solvent to produce Crystalline Form C or C*;

4) Step (c) adding toluene into HOAc as the solvent to produce Crystalline Form D;

5) Step (d) letting Crystalline Form A interact with DMA vapor to produce Crystalline Form E;

6) Step (e) letting Crystalline Form A interact with acetic acid vapor to produce Crystalline Form F;

7) Step (d) letting Crystalline Form A (De/ad) sorption in DVS to produce Crystalline Form G;

8) Step (d) heating Crystalline Form E to 80° C. to produce Crystalline Form H;

9) Step (d) heating Crystalline Form E to 150° C. to produce Crystalline Form I;

10) Step (d) heating Crystalline Form A to 150° C. to produce Crystalline Form J;

11) Step (e)) letting Crystalline Form A interact with MeOH vapor to produce Crystalline Form K;

12) Step (d) heating Crystalline Form K to 150° C. to produce Crystalline Form L.

In some embodiment, the present invention provides a process for preparing a crystalline Form C (i.e., Compound A sesqui-hydrate) comprising mixing at a temperature below the reflux temperature, for example, mixing at about 80° C. Compound A in a mixed solvent of i-PrOH and $H_2O$, or mixing at a temperature below the reflux temperature, for example, mixing at about 70° C. Compound A in a mixed solvent of i-PrOH and $H_2O$, or mixing at a temperature below the reflux temperature, for example, mixing at about 50° C. Compound A in a mixed solvent of i-PrOH and $H_2O$, wherein the amount of i-PrOH is greater than 40 vol % in terms of the total volume of i-PrOH and water, preferably 60 vol %, and more preferably 90 vol %. In some preferred embodiment, the above-mentioned mixed solvent is replaced with i-PrOH. In other embodiment, the process further comprises adding some crystal seeds into the resultant mixture after cooling to room temperature, and then letting the mixture stand for a certain duration, such as 12 hours, 24 hours, 2, 3, or 4 days or 1 week, 2 weeks.

Another purpose of the present invention is to provide the scalable synthetic methods for preparing the compound of Formula I, Formula II and Formula III (Compound A Sesqui-Hydrate-Crystalline Form C).

In another aspect, the present invention provides a pharmaceutical composition comprising a compound of Formula I or Formula II or Formula III according to any of the embodiments described herein and a pharmaceutically acceptable carrier.

In one embodiment, the pharmaceutical composition is suitable for oral administration.

In another embodiment, the pharmaceutical composition is in the form of tablet or capsule.

In another embodiment, the unit dosage of the tablet or capsule is 1-160 mg.

In another embodiment, the weight percentage of the compound in the pharmaceutical composition is 1-99%.

In another aspect, the present invention provides a method of treating or preventing a disease or disorder in a patient, comprising administering to said patient a therapeutically effective amount of a compound of Formula I or Formula II or Formula III according to any of the embodiments described herein or a pharmaceutical composition comprising a compound of Formula I or Formula II or Formula III.

In one embodiment, the disease or disorder is a cancer selected from the group consisting of brain cancer, lung cancer including small cell lung cancer, kidney cancer, bone cancer, liver cancer, bladder cancer, breast, head and neck cancer, ovarian cancer, melanoma, skin cancer, adrenal cancer, cervical cancer, lymphoma, or thyroid tumors and their complications.

In another embodiment, the disease is selected from the group consisting of BRCA1 and BRCA2 mutant breast, ovarian cancer, stomach cancer and their complications.

In another embodiment, the administered dosage of the compound is 5-320 mg/day, and the administration frequency is one to three times a day.

In another embodiment, the administered dosage of the compound is 5-240 mg/day, and the administration frequency is one to three times a day.

In another embodiment, the administered dosage of the compound is 10-200 mg/day, and the administration frequency is twice a day.

In another embodiment, the compound is (R)-2-fluoro-10a-methyl-7,8,9,10,10a,11-hexahydro-5,6,7a,11-tetraaza-cyclohepta[def]cyclopenta[a]fluoren-4(5H)-one free base or solvate or hydrate thereof in a crystalline form selected from the group consisting of Crystalline Forms A, B, C, C*, C**, D, E, F, G, H, I, J, K and L.

In another aspect, the present invention provides use of a compound of Formula I or Formula II or Formula III according to any of the embodiments described herein in the manufacture of a medicament for treatment of a disease or disorder associated with BRCA1 and BRCA2 mutant activities and HR-deficiencies.

In a preferred embodiment, the disease is a cancer.

These and other aspects of the present invention will be better appreciated in view of the following drawings, detailed description, and claims.

BRIEF DESCRIPTIONS OF THE DRAWINGS

DETAILED DESCRIPTION OF THE INVENTION

In one aspect, the present invention provides Crystalline Form C of Compound A Sesqui-Hydrate in a single crystal. The structure of Crystalline Form C of Compound A Sesqui-Hydrate was determined to be a single crystal by using a set of diffraction data collected from a single crystal grown via vapor diffusion at room temperature from IPA/water. Crystal data and structure refinement are listed in Table 1.

TABLE 1

Single Crystal Data and Structure Refinement of Crystalline Form C** of Compound A Sesqui-Hydrate

| | | |
|---|---|---|
| Identification code | CP1818 | — |
| Empirical formula | $C_{32}H_{36}N_8O_5F_2$ | — |
| Formula weight | 650.69 | — |
| Temperature | 293(2) | — |
| Wavelength | 1.54178 Å | — |
| Crystal system, space group | monoclinic | $P2_1$ |
| Unit cell dimensions | a = 7.1501(2) Å | alpha = 90.00 deg. . . |
| | b = 25.8668(6) Å | beta = 101.8840(10) deg. |
| | c = 17.1815(4) Å | gamma = 90.00 deg. |
| Volume | 3109.61(13) Å$^3$ | — |
| Z, Calculated density | 4 | 1.390 mg/mm3 |
| Absorption coefficient | 0.875 mm$^{-1}$ | — |
| F(000) | 1368.0 | — |
| Crystal size | 0.22 × 0.15 × 0.14 mm$^3$ | — |
| Theta range for data collection | 2.63 to 64.9 deg. | — |
| Limiting indices | −7 <= h <= 8, | — |
| | −27 <= k <= 30, | |
| | −19 <= l <= 20 | |
| Reflections collected/unique | 14364/7379[R(int) = 0.0376] | — |
| Completeness | 87.1% | — |
| Refinement method | Full matrix least squares on $F_2$ | — |
| Data/restraints/parameters | 7379/4/863 | |
| Goodness-of-fit on F2 | 1.062 | — |
| Final R indices [I > 2sigma(I)] | R1 = 0.0660 | wR$_2$ = 0.1802 |
| Absolute structure Flack | 0.03(12) | |
| Largest diff. peak and hole | 1.16 and −0.47e.A−3 | — |

Figure 1:
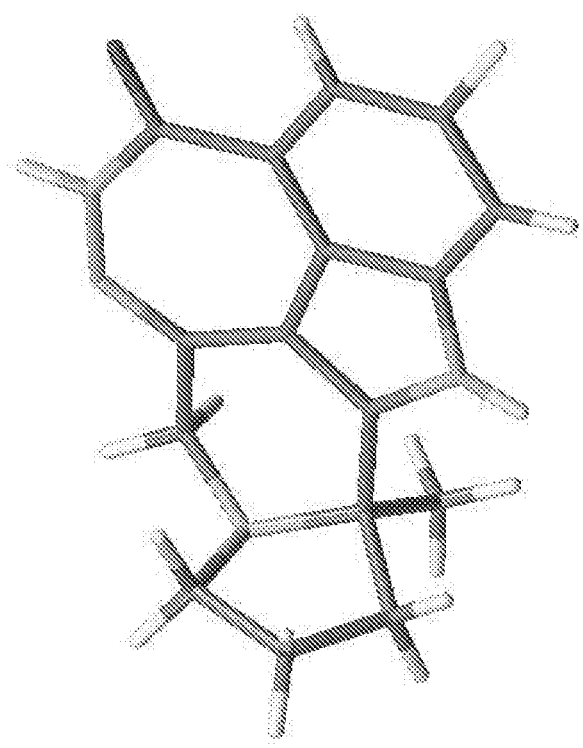
FIG. 1 shows the absolute structure of Compound A.
Figure 2:
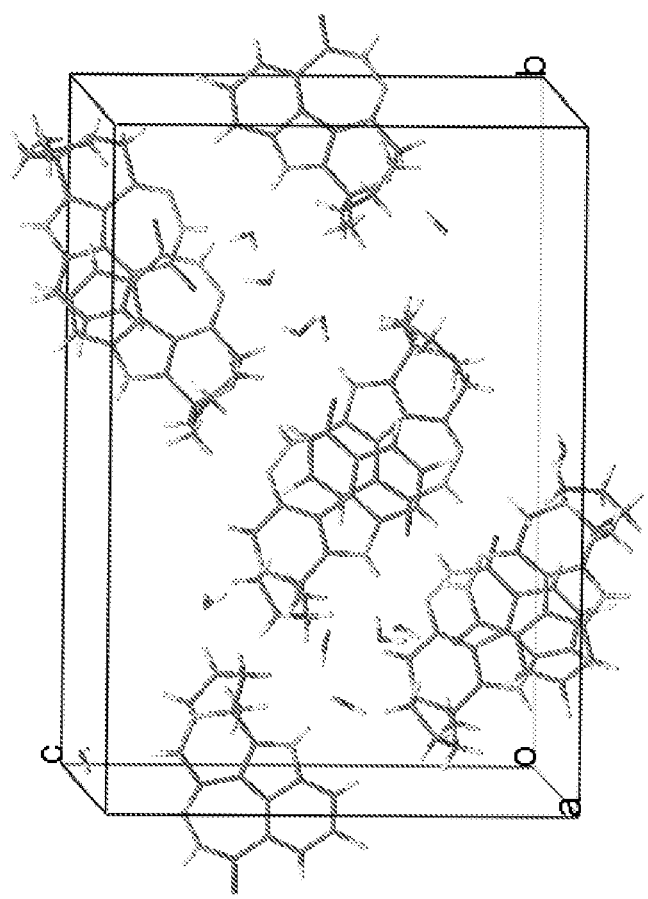
FIG. 2 shows a unit cell of Crystalline Form C** of Compound A Sesqui-Hydrate in a single crystal.
Figure 3:
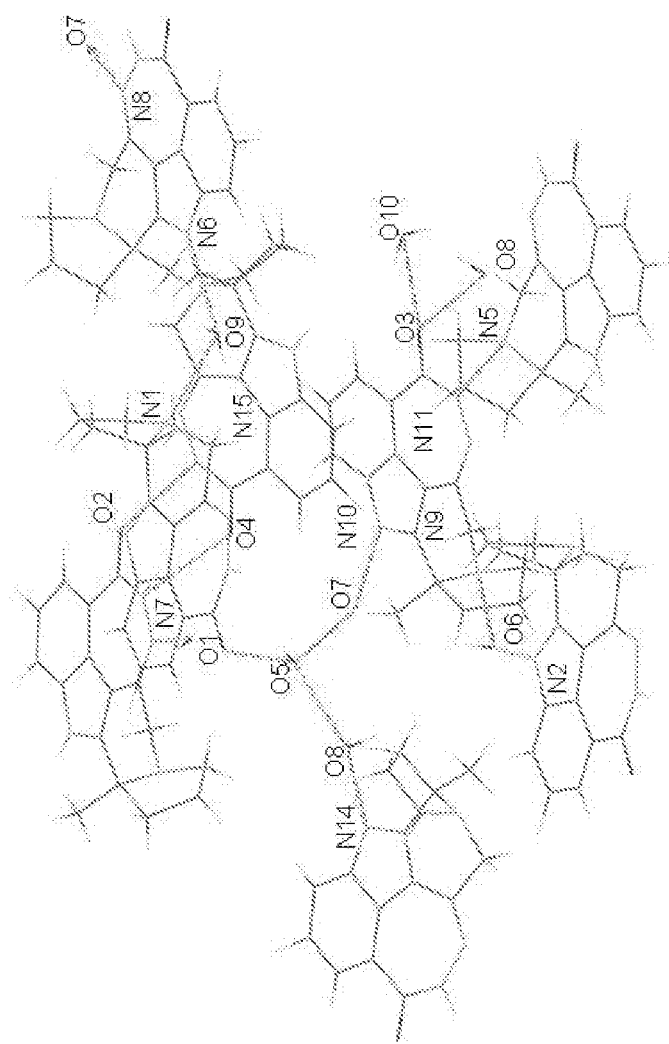
FIG. 3 illustrates hydrogen bonds of Crystalline Form C** of Compound A Sesqui-Hydrate in a single crystal.
Figure 4:
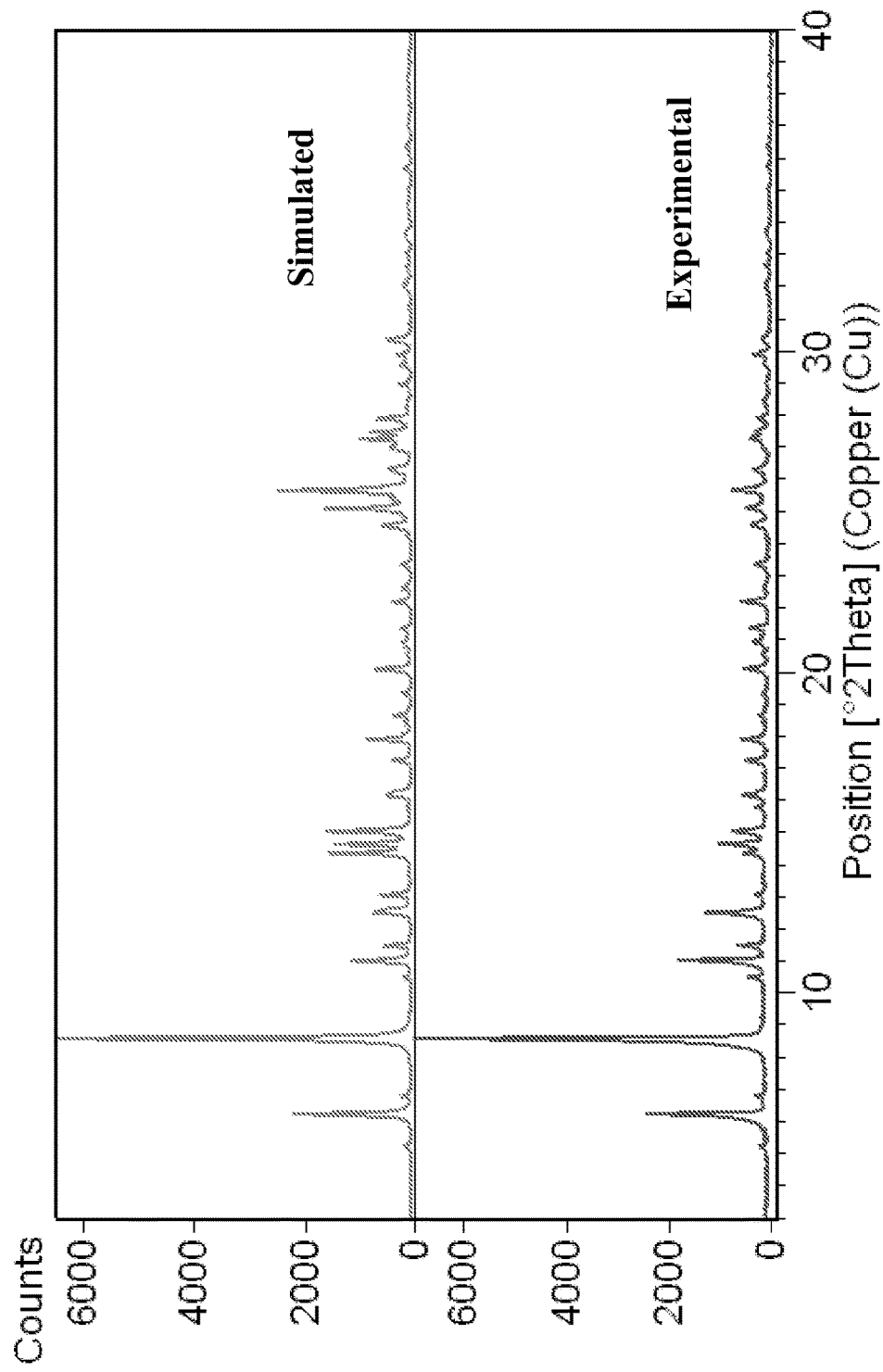
FIG. 4 shows simulated and experimental XRPD patterns of Crystalline Form C** of Compound A Sesqui-Hydrate in a single crystal.

The crystal structure of Crystalline Form C of Compound A Sesqui-Hydrate has been successfully determined using a set of diffraction data collected from a single crystal grown via vapor diffusion at room temperature from IPA/water. The absolute structure of Compound A is displayed in FIG. 1. Result shows that single crystal of sesquihydrate was obtained. Configuration of C4 (R) was determined. Unit cell of Crystalline Form C of Compound A Sesqui-Hydrate in a single crystal is shown in FIG. 2. Hydrogen bonds of Crystalline Form C** of Compound A Sesqui-Hydrate a single crystal are shown in FIG. 3. A zigzag chain was formed via hydrogen bonds N11-H11 . . . N5, N7-H7 . . . O4 and N15-H15 . . . O2. These zigzag chains were connected by hydrogen bonds between (N2-H2 . . . O 6, O6-H6A . . . N9, O9-H9A . . . N1 and N6-H6 . . . O9) and within (O8-H8B . . . O5, N10-H10 . . . O7, N14-H14 . . . O8, O5-H5B . . . O1, O7-H7A . . . N8, O7-H7B . . . O5, O8-H8A . . . O3 and O10-H10B . . . O3) these chains to form a three dimensional structure. The theoretical XRPD pattern calculated from the single crystal structure and experimental XRPD pattern are very similar and displayed in FIG. 4.

Figure 5:
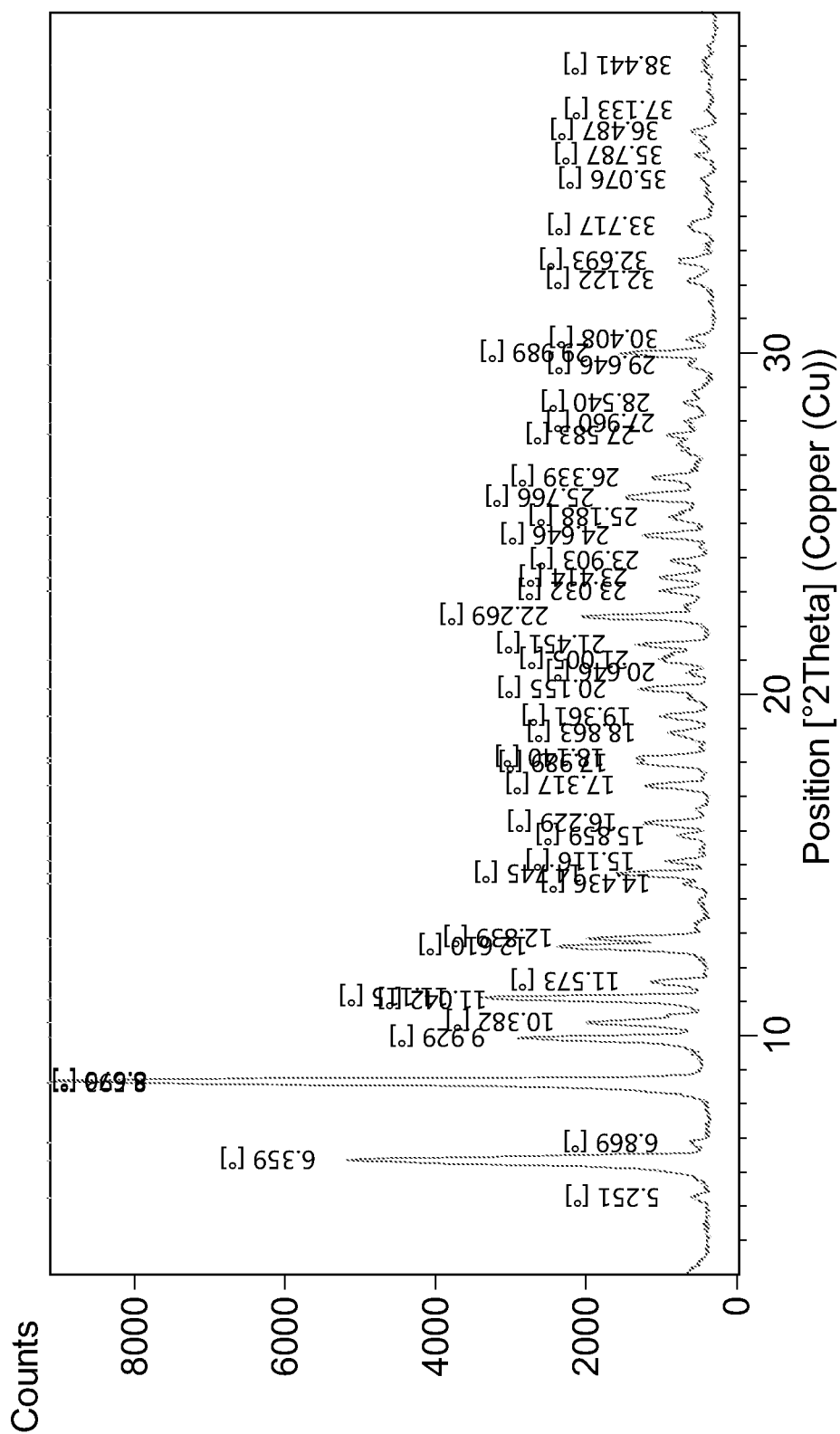
FIG. 5 shows an X-ray diffraction pattern of Crystalline Form A of Compound A (obtained by recrystallization from isopropanol/water).

In another embodiment, the present invention provides Crystalline Form A of Compound A. As shown in FIG. 5, Crystalline Form A's X-ray powder diffraction spectra typically have the following peak diffraction angles (where "spacing" is shown as the "d-value" in FIG. 5):

TABLE 2

X-ray Diffraction Pattern of Crystalline Form A of Compound A

| Peak# | Diffraction angle (2-theta) | Spacing | Relative intensity |
|---|---|---|---|
| 1 | 6.359372 | 13.89889 | 54.67 |
| 2 | 8.592671 | 10.29083 | 81.24 |
| 3 | 8.670472 | 10.19866 | 100.00 |
| 4 | 9.929488 | 8.90817 | 28.96 |
| 5 | 10.381550 | 8.52126 | 18.33 |
| 6 | 11.042290 | 8.01281 | 28.75 |
| 7 | 11.115210 | 7.96041 | 34.55 |
| 8 | 12.609790 | 7.02005 | 22.56 |
| 9 | 12.838980 | 6.89525 | 18.79 |

TABLE 2-continued

X-ray Diffraction Pattern of Crystalline Form A of Compound A

| Peak# | Diffraction angle (2-theta) | Spacing | Relative intensity |
|---|---|---|---|
| 10 | 14.744730 | 6.00806 | 14.19 |
| 11 | 17.988780 | 4.93123 | 10.67 |
| 12 | 18.140240 | 4.89039 | 11.11 |
| 13 | 20.155290 | 4.40579 | 10.82 |
| 14 | 21.451250 | 4.14246 | 11.12 |
| 15 | 22.269250 | 3.99211 | 19.66 |
| 16 | 24.645850 | 3.61228 | 10.46 |
| 17 | 25.766010 | 3.45772 | 12.87 |
| 18 | 29.988540 | 2.97978 | 13.80 |

Figure 6:
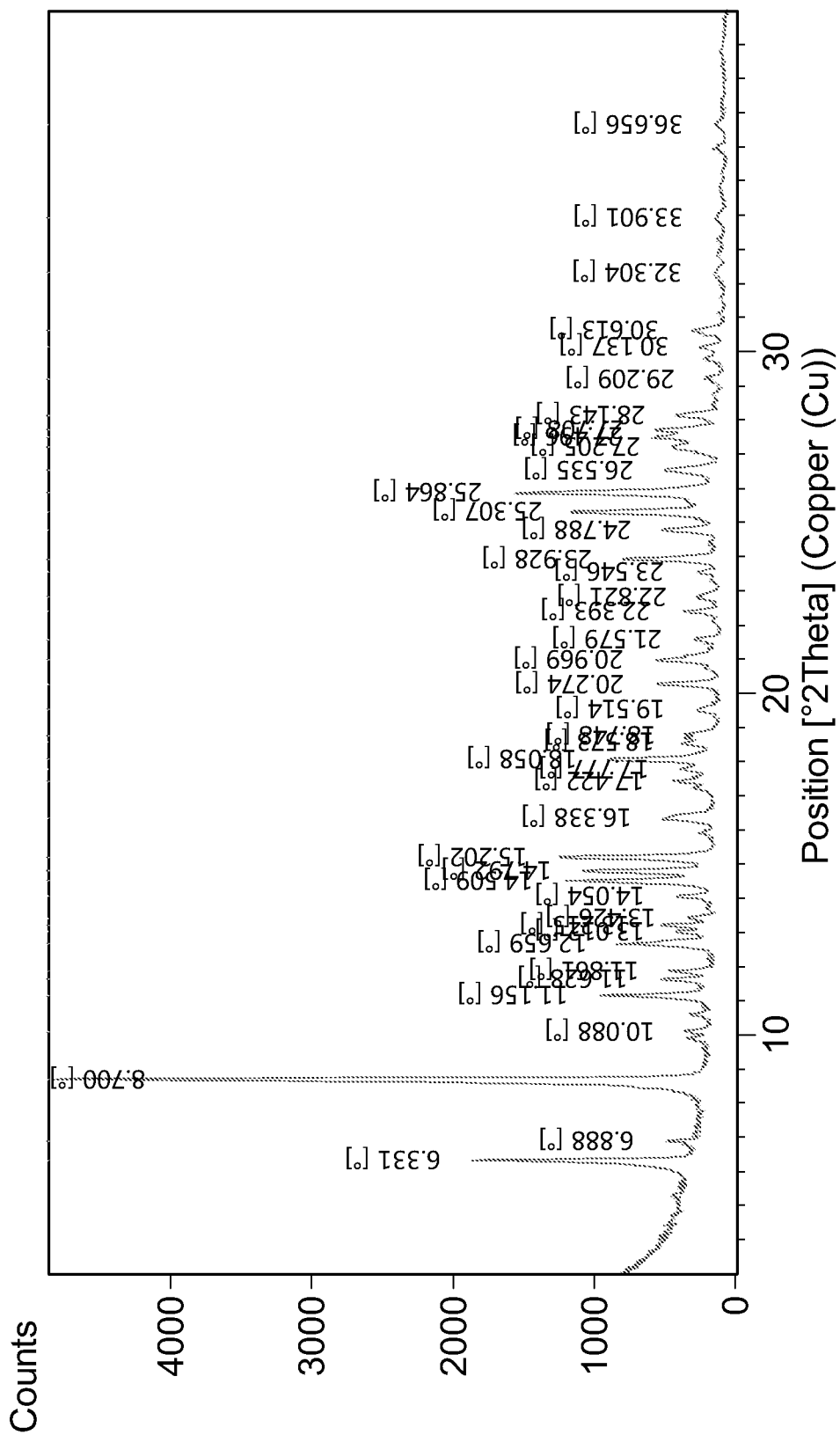
FIG. 6 shows an X-ray diffraction pattern of Crystalline Form B of Compound A.

In another embodiment, the present invention provides Crystalline Form B of Compound A. As shown in FIG. 6, Crystalline Form B's X-ray powder diffraction spectra typically have the following peak diffraction angles (where "spacing" is shown as the "d-value" in FIG. 6):

TABLE 3

X-ray Diffraction Pattern of Crystalline Form B of Compound A

| Peak# | Diffraction angle (2-theta) | Spacing | Relative intensity |
|---|---|---|---|
| 1 | 6.330541 | 13.96213 | 32.91 |
| 2 | 8.699873 | 10.16426 | 100.00 |
| 3 | 11.156260 | 7.93120 | 16.31 |
| 4 | 12.659450 | 6.99263 | 13.62 |
| 5 | 14.509300 | 6.10501 | 21.95 |
| 6 | 14.791890 | 5.98900 | 19.27 |
| 7 | 15.201870 | 5.82840 | 23.03 |
| 8 | 18.058410 | 4.91237 | 15.82 |
| 9 | 23.928100 | 3.71898 | 14.21 |
| 10 | 25.307050 | 3.51938 | 21.93 |
| 11 | 25.864130 | 3.44483 | 31.04 |

Figure 7A:
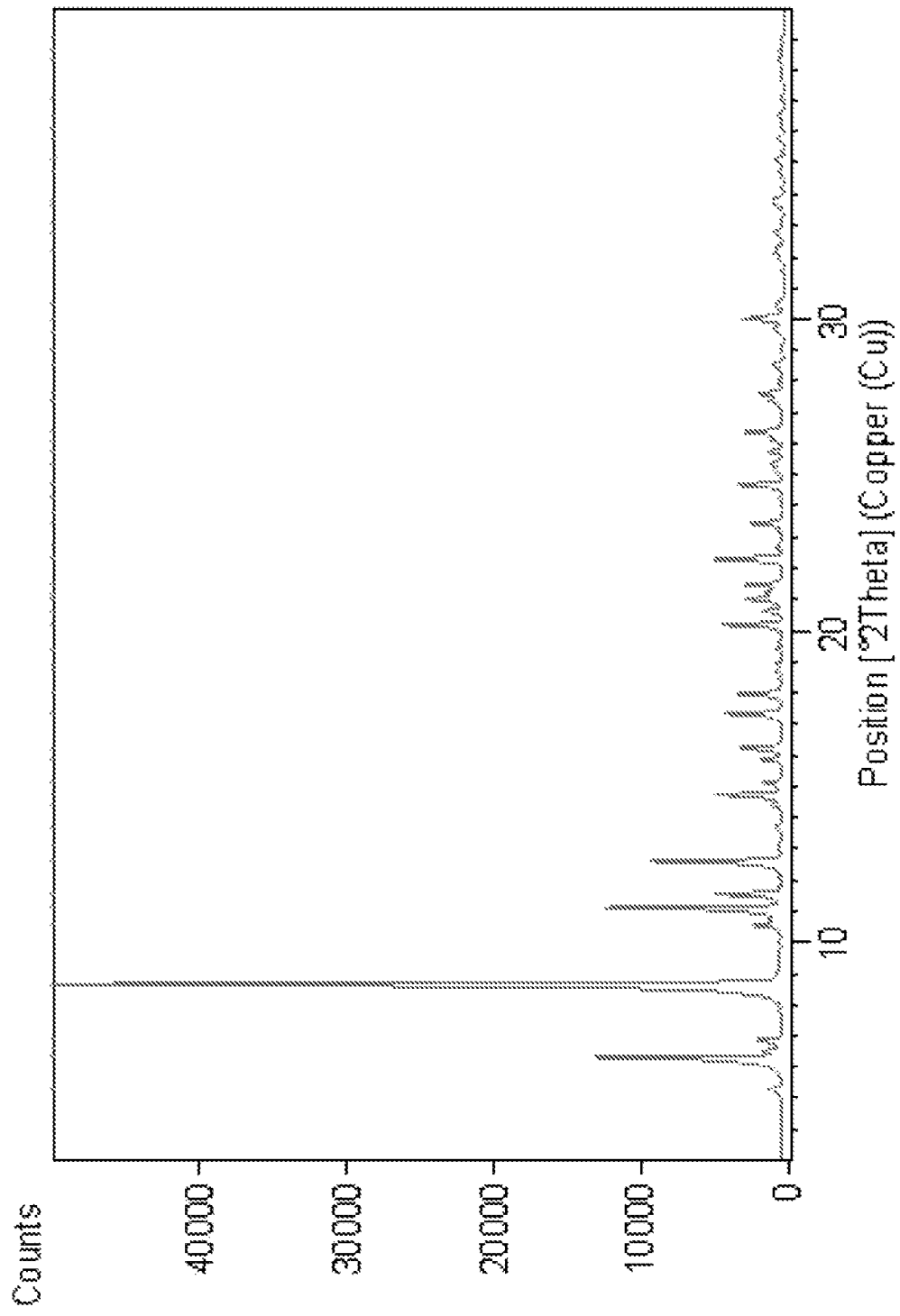
FIGS. 7A and 7B show an X-ray diffraction pattern of Crystalline Forms C and C* of Compound A Sesqui-Hydrate, respectively, wherein Crystalline Form C was prepared in a large scale by recrystallization from isopropanol/water as disclosed in Example 1, and Crystalline Form C* was prepared in a laboratory scale as disclosed in Example 5.

In another embodiment, the present invention provides Crystalline Form C of Compound A (Sesqui-Hydrate), which is prepared by the process disclosed in Example 1 in a large scale. As shown in FIG. 7A, Crystalline Form C's X-ray powder diffraction spectra typically have the following peak diffraction angles (where "spacing" is shown as the "d-value" in FIG. 7):

TABLE 4

X-ray Diffraction Pattern of Crystalline Form C of Compound A Sesqui-Hydrate

| Peak# | Diffraction angle (2-theta) | Spacing | Relative intensity |
|---|---|---|---|
| 1 | 5.311572 | 16.63811 | 1.74 |
| 2 | 6.324076 | 13.97639 | 26.02 |
| 3 | 6.542414 | 13.51044 | 2.57 |
| 4 | 6.879973 | 12.84830 | 3.34 |
| 5 | 8.676094 | 10.19207 | 100.00 |
| 6 | 10.577890 | 8.36353 | 4.12 |
| 7 | 11.120210 | 7.95683 | 24.78 |
| 8 | 11.574990 | 7.64521 | 9.48 |
| 9 | 12.609210 | 7.02038 | 18.70 |
| 10 | 13.112850 | 6.75185 | 0.56 |
| 11 | 13.719490 | 6.45463 | 1.08 |
| 12 | 14.416950 | 6.14390 | 1.84 |
| 13 | 14.755390 | 6.00374 | 9.51 |
| 14 | 15.126870 | 5.85713 | 2.77 |
| 15 | 15.874480 | 5.58293 | 3.04 |
| 16 | 16.239320 | 5.45831 | 6.38 |
| 17 | 17.346580 | 5.11231 | 8.40 |
| 18 | 17.971700 | 4.93587 | 6.78 |
| 19 | 18.713690 | 4.74181 | 1.09 |
| 20 | 18.931530 | 4.68774 | 1.21 |
| 21 | 19.405650 | 4.57426 | 0.83 |
| 22 | 20.186990 | 4.39895 | 8.72 |
| 23 | 20.633840 | 4.30468 | 2.89 |
| 24 | 21.025170 | 4.22544 | 5.37 |
| 25 | 21.205290 | 4.18995 | 2.85 |
| 26 | 21.480150 | 4.13695 | 5.72 |
| 27 | 22.299940 | 3.98669 | 10.32 |
| 28 | 22.714940 | 3.91478 | 0.65 |
| 29 | 23.444130 | 3.79465 | 4.94 |
| 30 | 23.815610 | 3.73629 | 0.37 |
| 31 | 24.266090 | 3.66794 | 0.50 |
| 32 | 24.656650 | 3.61072 | 6.52 |
| 33 | 25.316810 | 3.51804 | 1.60 |
| 34 | 25.734190 | 3.46193 | 2.25 |
| 35 | 26.108150 | 3.41318 | 1.95 |
| 36 | 26.374610 | 3.37930 | 5.52 |
| 37 | 27.390320 | 3.25625 | 1.99 |

Figure 7B:
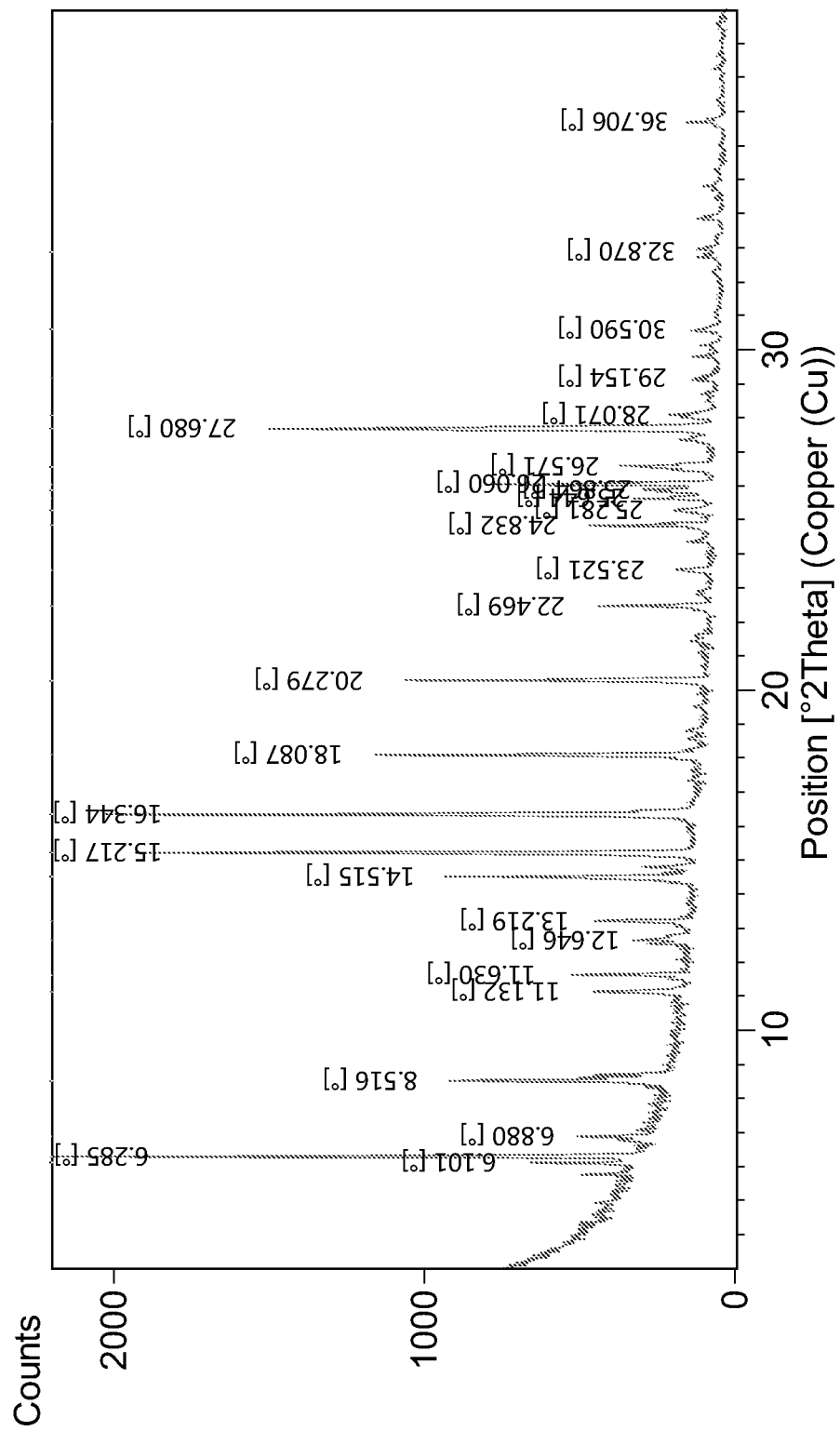

In yet another embodiment, the present invention provides Crystalline Form C* of Compound A (Sesqui-Hydrate), which is prepared by the process disclosed in Example 5 in a laboratory scale. As also shown in FIG. 7B, Crystalline Form C* has a X-ray powder diffraction spectra which typically have the following peak diffraction angles (where "spacing" is shown as the "d-value" in FIG. 7):

TABLE 4*

X-ray Diffraction Pattern of Crystalline Form C* of Compound A Sesqui-Hydrate

| Peak# | Diffraction angle (2-theta) | Spacing | Relative intensity |
|---|---|---|---|
| 1 | 6.100802 | 14.48738 | 17.25 |
| 2 | 6.285063 | 14.06305 | 100.00 |
| 3 | 6.880020 | 12.84822 | 9.77 |
| 4 | 8.516424 | 10.38279 | 36.51 |
| 5 | 11.132140 | 7.94834 | 15.13 |
| 6 | 11.630460 | 7.60887 | 19.60 |
| 7 | 13.218540 | 6.69810 | 14.93 |
| 8 | 14.514800 | 6.10271 | 41.64 |
| 9 | 15.216960 | 5.82265 | 94.45 |
| 10 | 16.343840 | 5.42364 | 99.88 |
| 11 | 18.086680 | 4.90476 | 55.30 |
| 12 | 20.278680 | 4.37926 | 52.30 |
| 13 | 22.468730 | 3.95712 | 18.78 |
| 14 | 24.832200 | 3.58559 | 20.66 |
| 15 | 26.060310 | 3.41934 | 22.92 |
| 16 | 26.570800 | 3.35479 | 13.74 |
| 17 | 27.679950 | 3.22283 | 75.52 |

Crystalline Form C of Compound A Sesqui-Hydrate is a rather stable crystalline form having an average particle size (D90) of approximately 50 microns, it can be readily formulated into drug product for clinical uses. Crystalline Form C of Compound A Sesqui-Hydrate and Crystalline Form C* of Compound A Sesqui-Hydrate have substantially the identical peak positions, while the relative intensities vary as shown in FIGS. 7A and 7B.

Figure 8:
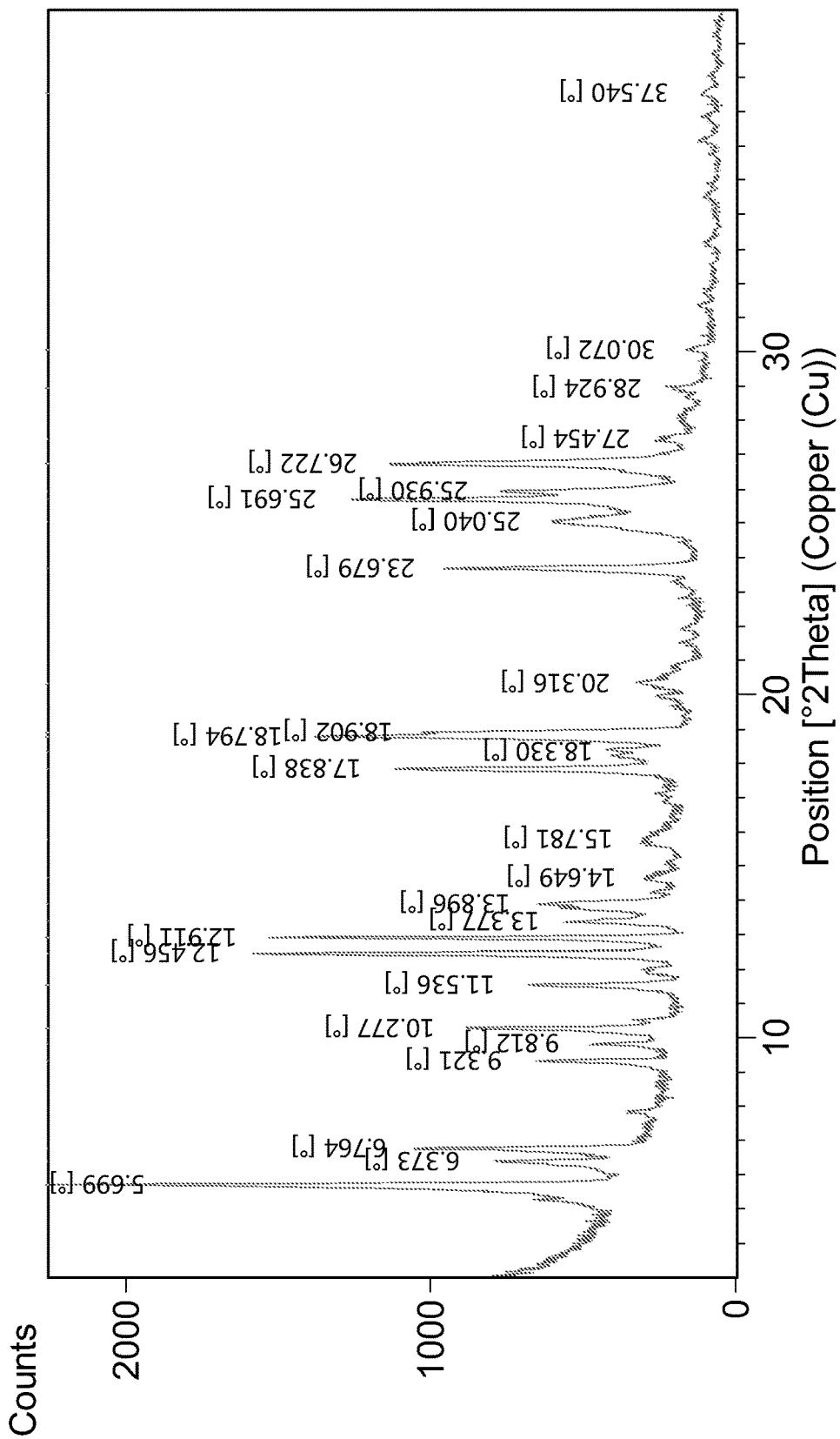
FIG. 8 shows an X-ray diffraction pattern of Crystalline Form D of Compound A.

In another embodiment, the present invention provides Crystalline Form D of Compound A. As shown in FIG. 8, Crystalline Form D's X-ray powder diffraction spectra typically have the following peak diffraction angles (where "spacing" is shown as the "d-value" in FIG. 8):

TABLE 5

X-ray Diffraction Pattern of Crystalline Form D of Compound A

| Peak# | Diffraction angle (2-theta) | Spacing | Relative intensity |
|---|---|---|---|
| 1 | 5.698822 | 15.50835 | 100.00 |
| 2 | 6.372973 | 13.86926 | 23.70 |
| 3 | 6.763580 | 13.06914 | 37.84 |
| 4 | 9.321335 | 9.48795 | 23.16 |
| 5 | 9.812119 | 9.01446 | 13.28 |
| 6 | 10.276560 | 8.60807 | 35.66 |
| 7 | 11.536360 | 7.67073 | 25.75 |
| 8 | 12.455850 | 7.10647 | 74.42 |
| 9 | 12.910680 | 6.85712 | 71.73 |
| 10 | 13.376630 | 6.61929 | 18.56 |
| 11 | 13.895960 | 6.37306 | 24.00 |
| 12 | 17.837810 | 4.97262 | 51.71 |
| 13 | 18.330370 | 4.84010 | 11.08 |
| 14 | 18.793570 | 4.72184 | 66.01 |
| 15 | 18.902030 | 4.69498 | 46.41 |
| 16 | 23.679050 | 3.75753 | 44.14 |
| 17 | 25.039630 | 3.55636 | 25.98 |
| 18 | 25.691290 | 3.46761 | 62.03 |
| 19 | 25.929530 | 3.43629 | 35.59 |
| 20 | 26.721510 | 3.33621 | 55.20 |

Figure 9:
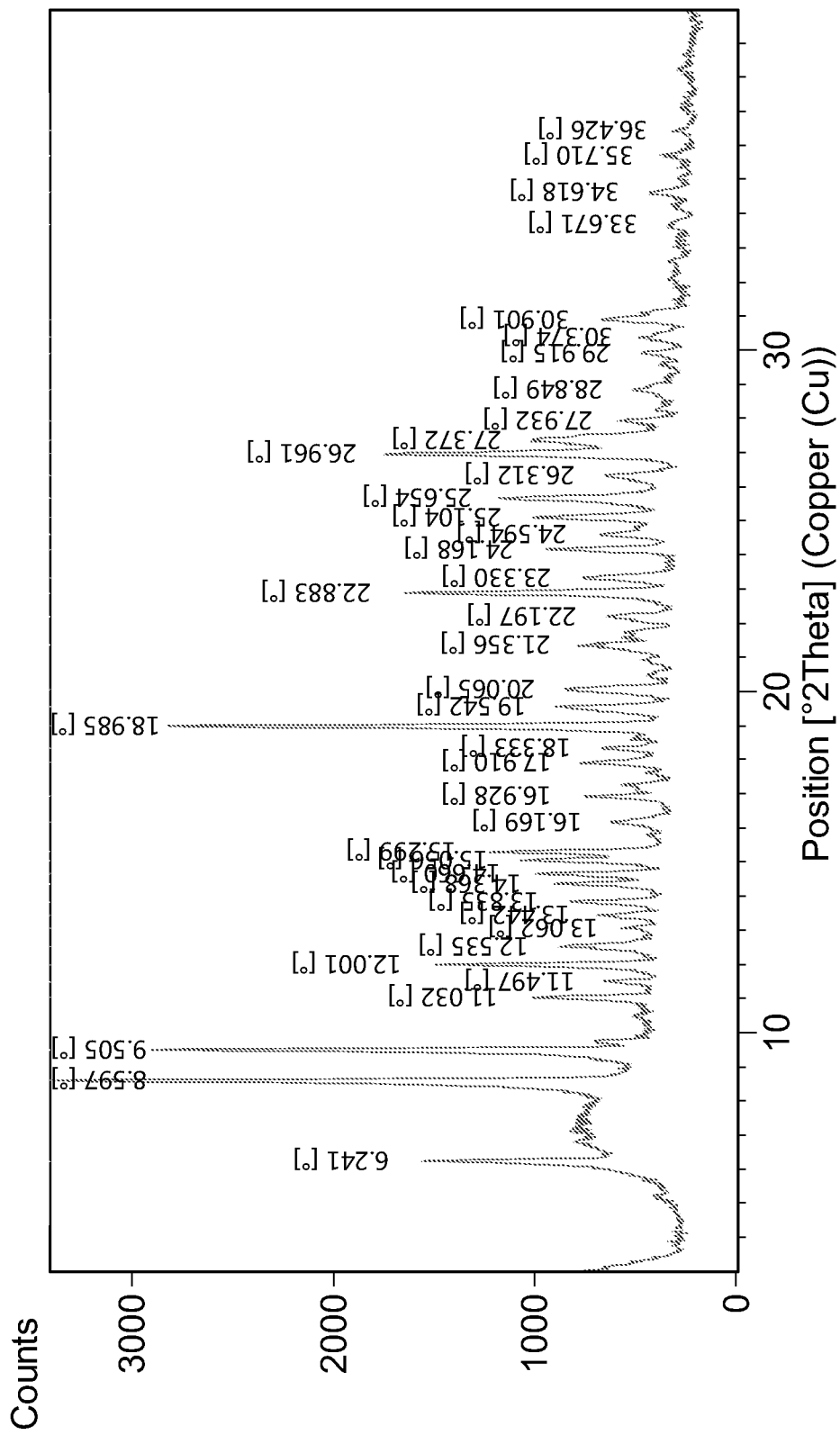
FIG. 9 shows an X-ray diffraction pattern of Crystalline Form E of Compound A.

In another embodiment, the present invention provides Crystalline Form E of Compound A. As shown in FIG. 9, Crystalline Form F's X-ray powder diffraction spectra typically have the following peak diffraction angles (where "spacing" is shown as the "d-value" in FIG. 9):

TABLE 6

X-ray Diffraction Pattern of Crystalline Form E of Compound A

| Peak# | Diffraction angle (2-theta) | Spacing | Relative intensity |
|---|---|---|---|
| 1 | 6.241343 | 14.16147 | 40.68 |
| 2 | 8.596938 | 10.28573 | 100.00 |
| 3 | 9.504722 | 9.30530 | 83.73 |
| 4 | 11.031640 | 8.02052 | 23.83 |
| 5 | 11.497400 | 7.69663 | 11.59 |
| 6 | 12.001170 | 7.37466 | 39.12 |
| 7 | 12.535330 | 7.06158 | 19.06 |
| 8 | 13.441520 | 6.58748 | 12.63 |
| 9 | 13.834690 | 6.40114 | 17.59 |
| 10 | 14.368380 | 6.16456 | 20.24 |
| 11 | 14.660220 | 6.04250 | 23.57 |
| 12 | 15.056200 | 5.88446 | 25.60 |
| 13 | 15.298870 | 5.79166 | 30.55 |
| 14 | 16.168720 | 5.48199 | 10.83 |
| 15 | 16.928060 | 5.23775 | 15.64 |
| 16 | 17.909930 | 4.95276 | 15.64 |
| 17 | 18.332760 | 4.83947 | 12.66 |
| 18 | 18.985490 | 4.67454 | 81.75 |
| 19 | 19.542210 | 4.54261 | 19.74 |
| 20 | 20.065340 | 4.42534 | 18.43 |
| 21 | 21.355580 | 4.16080 | 16.02 |
| 22 | 22.197250 | 4.00490 | 12.02 |
| 23 | 22.882840 | 3.88644 | 44.57 |
| 24 | 23.329540 | 3.81303 | 16.10 |
| 25 | 24.167640 | 3.68266 | 22.03 |
| 26 | 24.594340 | 3.61973 | 13.66 |
| 27 | 25.104500 | 3.54731 | 24.04 |
| 28 | 25.653540 | 3.47263 | 28.60 |
| 29 | 26.311740 | 3.38723 | 12.57 |
| 30 | 26.960840 | 3.30714 | 47.05 |
| 31 | 27.372450 | 3.25834 | 24.13 |
| 32 | 30.900990 | 2.89385 | 13.58 |

Figure 10:
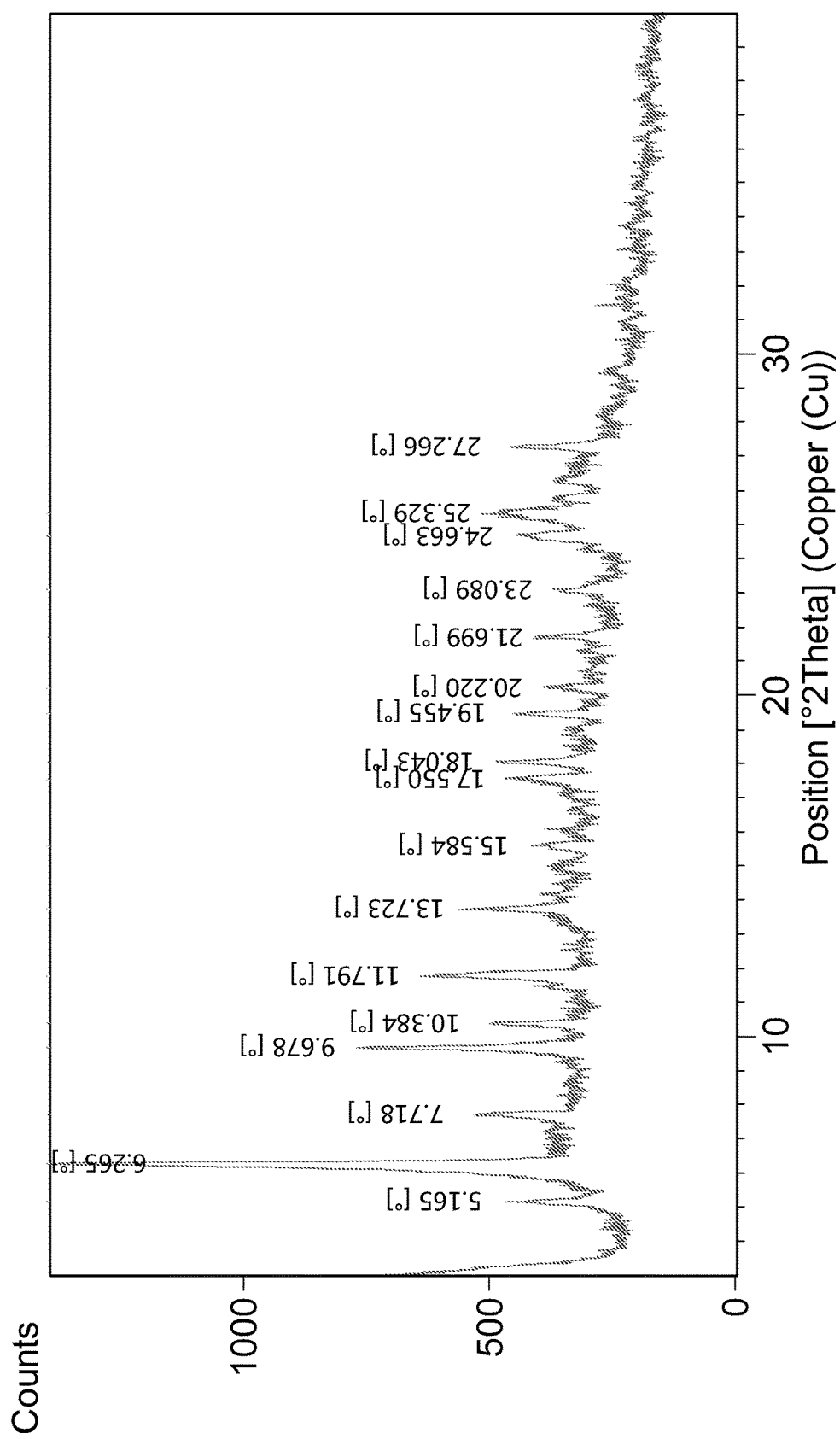
FIG. 10 shows an X-ray diffraction pattern of Crystalline Form F of Compound A.

In another embodiment, the present invention provides Crystalline Form F of Compound A. As shown in FIG. 10, Crystalline Form F's X-ray powder diffraction spectra typically have the following peak diffraction angles (where "spacing" is shown as the "d-value" in FIG. 10):

TABLE 7

X-ray Diffraction Pattern of Crystalline Form F of Compound A

| Peak# | Diffraction angle (2-theta) | Spacing | Relative intensity |
|---|---|---|---|
| 1 | 5.164817 | 17.11054 | 18.62 |
| 2 | 6.265009 | 14.10802 | 100.00 |
| 3 | 7.718327 | 11.45452 | 25.32 |
| 4 | 9.677702 | 9.13936 | 44.33 |
| 5 | 10.383570 | 8.51960 | 22.57 |
| 6 | 11.790820 | 7.50575 | 32.97 |
| 7 | 13.723440 | 6.45278 | 25.29 |
| 8 | 15.584450 | 5.68617 | 14.07 |
| 9 | 17.549580 | 5.05363 | 18.14 |
| 10 | 18.043220 | 4.91647 | 20.24 |
| 11 | 19.455350 | 4.56269 | 18.01 |
| 12 | 20.219940 | 4.39185 | 11.79 |
| 13 | 21.698520 | 4.09581 | 11.54 |
| 14 | 23.088810 | 3.85223 | 9.97 |
| 15 | 24.663300 | 3.60976 | 16.93 |
| 16 | 25.328640 | 3.51643 | 20.84 |
| 17 | 27.266460 | 3.27076 | 19.09 |

Figure 11:
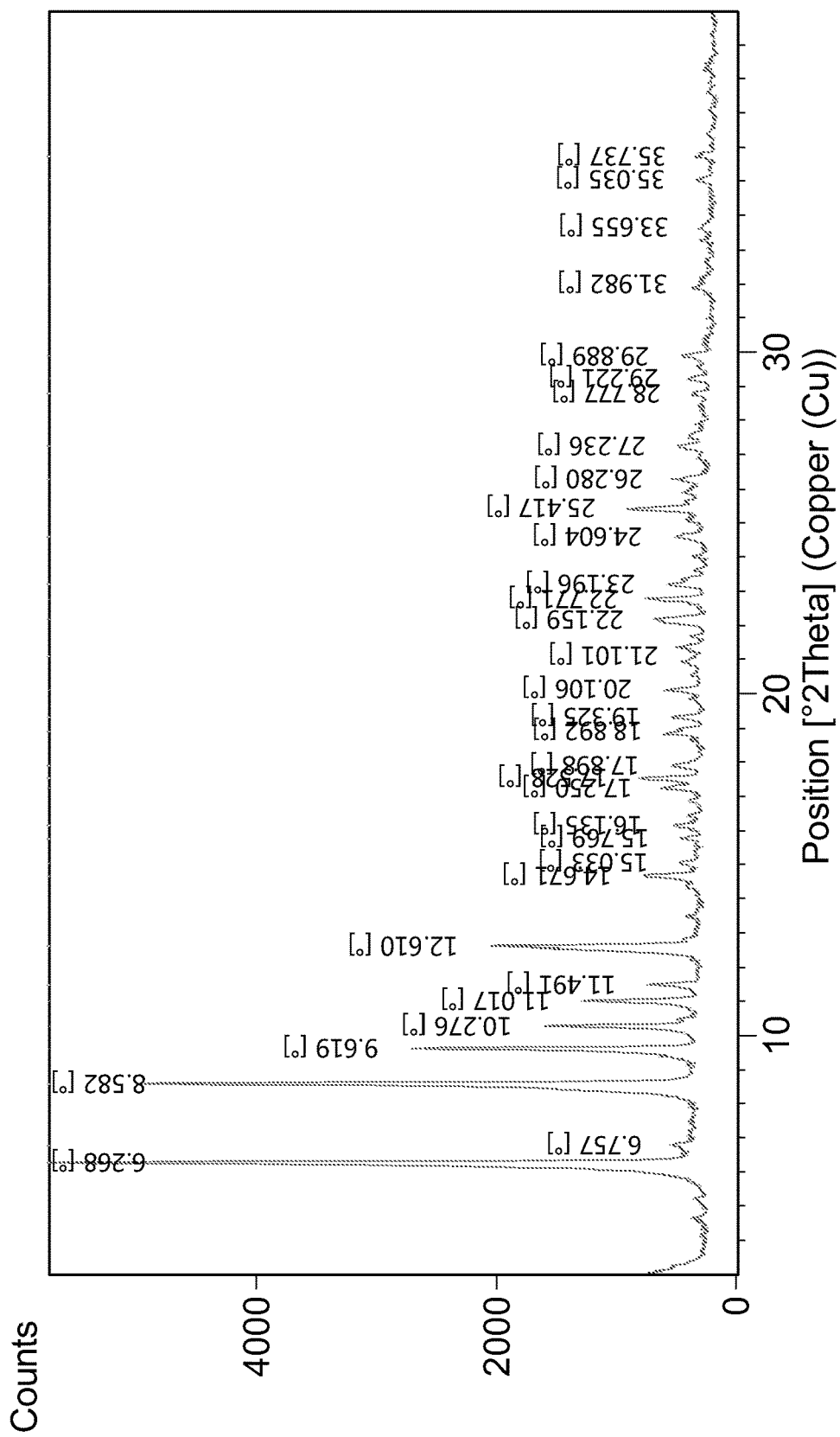
FIG. 11 shows an X-ray diffraction pattern of Crystalline Form G of Compound A.

In another embodiment, the present invention provides Crystalline Form G of Compound A. As shown in FIG. 11, Crystalline Form G's X-ray powder diffraction spectra typically have the following peak diffraction angles (where "spacing" is shown as the "d-value" in FIG. 11):

TABLE 8

X-ray Diffraction Pattern of Crystalline Form G of Compound A

| Peak# | Diffraction angle (2-theta) | Spacing | Relative intensity |
|---|---|---|---|
| 1 | 6.267537 | 14.10234 | 100.00 |
| 2 | 8.582008 | 10.30359 | 86.00 |
| 3 | 9.618750 | 9.19524 | 44.68 |
| 4 | 10.275970 | 8.60857 | 24.39 |
| 5 | 11.017290 | 8.03093 | 18.64 |
| 6 | 12.610230 | 7.01981 | 32.77 |
| 7 | 17.527530 | 5.05994 | 10.07 |
| 8 | 25.417370 | 3.50435 | 12.46 |

Figure 12:
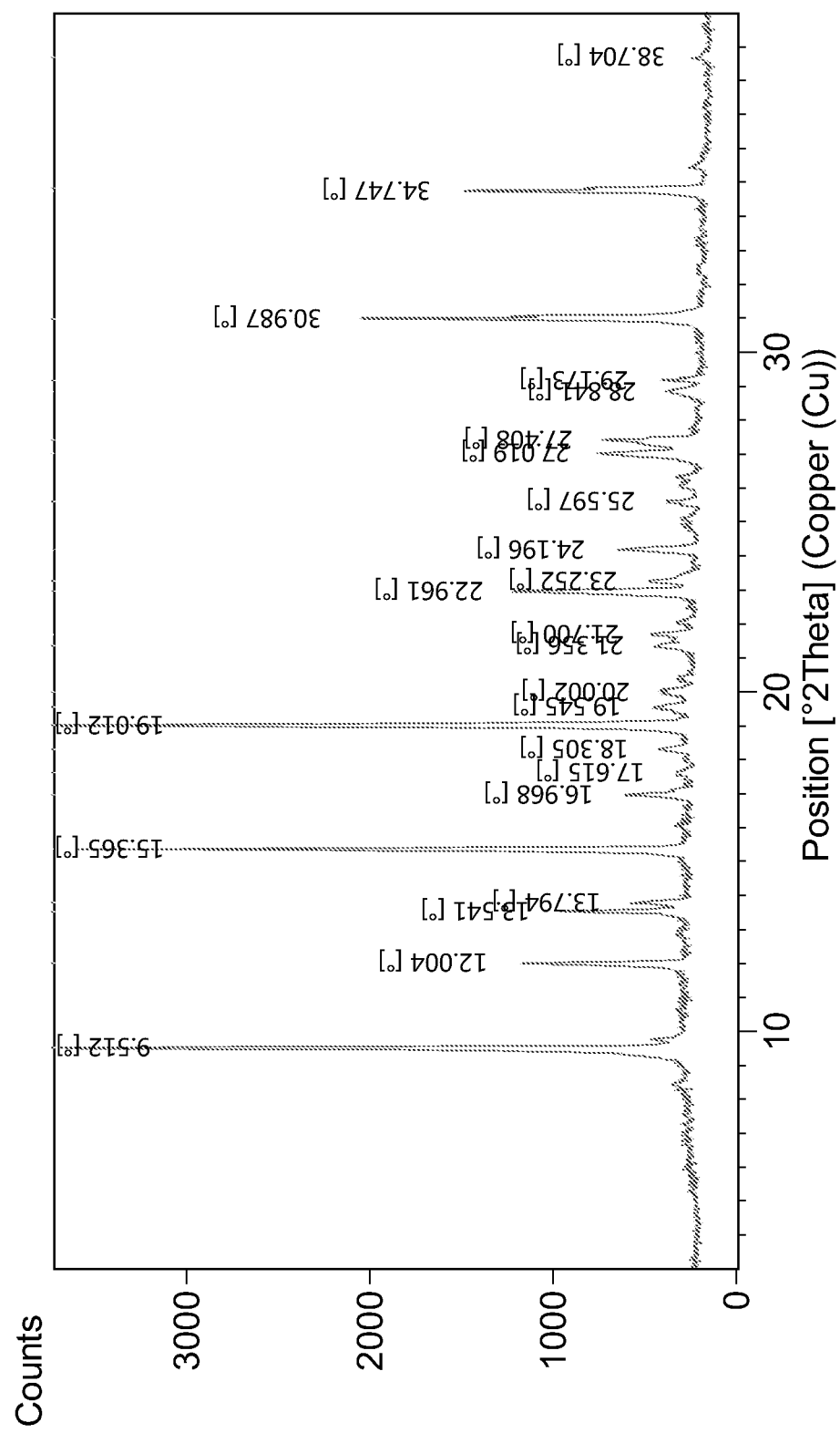
FIG. 12 shows an X-ray diffraction pattern of Crystalline Form H of Compound A.

In another embodiment, the present invention provides Crystalline Form H of Compound A. As shown in FIG. 12, Crystalline Form H's X-ray powder diffraction spectra typically have the following peak diffraction angles (where "spacing" is shown as the "d-value" in FIG. 12):

TABLE 9

X-ray Diffraction Pattern of Crystalline Form H of Compound A

| Peak# | Diffraction angle (2-theta) | Spacing | Relative intensity |
|---|---|---|---|
| 1 | 9.512062 | 9.29813 | 98.78 |
| 2 | 12.004320 | 7.37274 | 26.49 |
| 3 | 13.541340 | 6.53915 | 20.04 |
| 4 | 15.365480 | 5.76670 | 95.81 |
| 5 | 16.968260 | 5.22543 | 10.51 |
| 6 | 19.012000 | 4.66808 | 100.00 |
| 7 | 22.960770 | 3.87342 | 28.45 |
| 8 | 24.196220 | 3.67838 | 12.53 |
| 9 | 27.019090 | 3.30014 | 15.33 |
| 10 | 27.407580 | 3.25424 | 14.82 |
| 11 | 30.987400 | 2.88597 | 54.55 |
| 12 | 34.747080 | 2.57970 | 37.66 |
| 13 | 34.847130 | 2.57892 | 18.31 |

Figure 13:
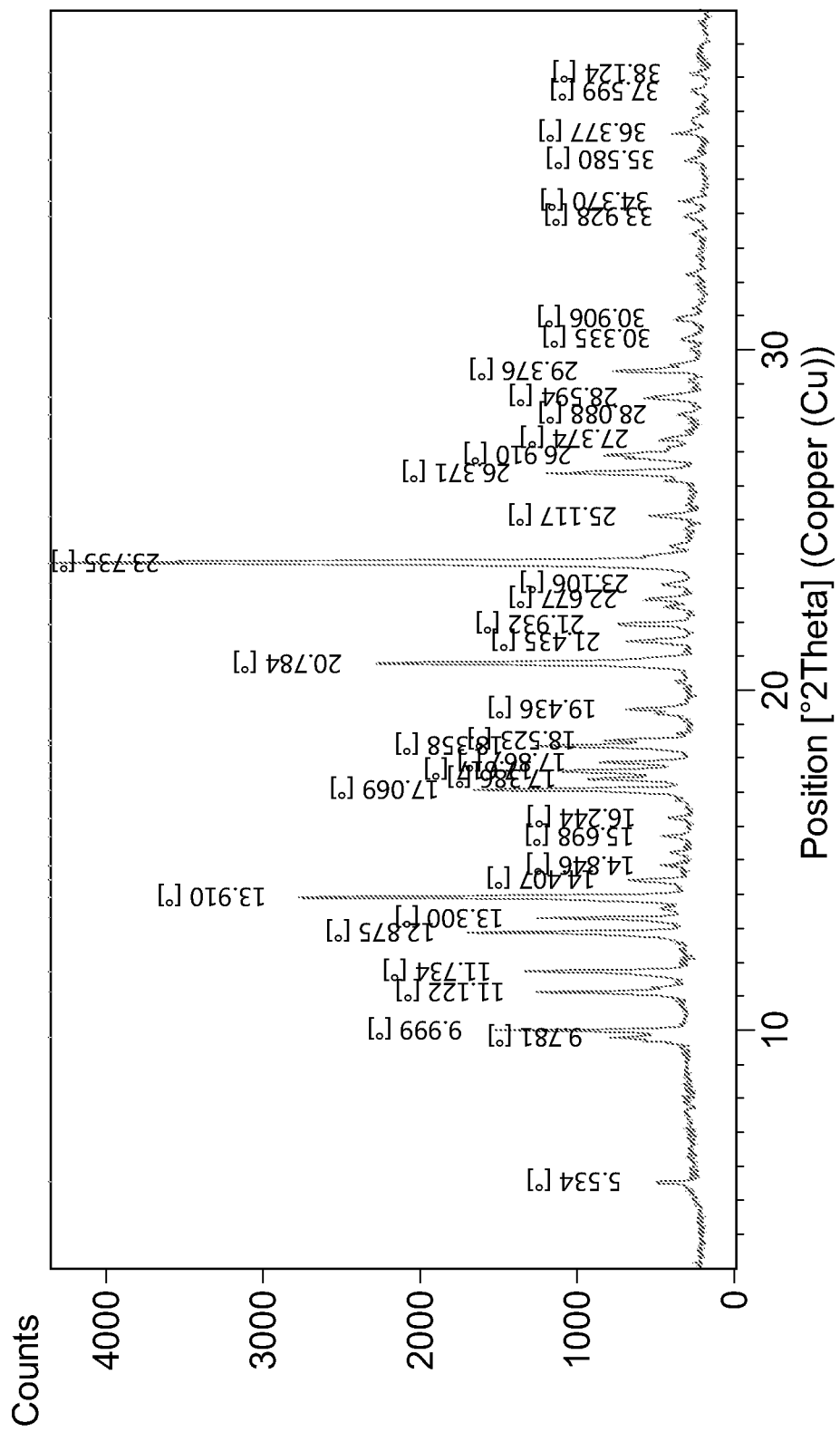
FIG. 13 shows an X-ray diffraction pattern of Crystalline Form I of Compound A.

In another embodiment, the present invention provides Crystalline Form I of Compound A. As shown in FIG. 13, Crystalline Form I's X-ray powder diffraction spectra typically have the following peak diffraction angles (where "spacing" is shown as the "d-value" in FIG. 13):

TABLE 10

X-ray Diffraction Pattern of Crystalline Form J of Compound A

| Peak# | Diffraction angle (2-theta) | Spacing | Relative intensity |
|---|---|---|---|
| 1 | 9.781318 | 9.04277 | 11.42 |
| 2 | 9.999168 | 8.84624 | 29.97 |
| 3 | 11.122150 | 7.95545 | 23.42 |
| 4 | 11.733710 | 7.54215 | 25.61 |
| 5 | 12.875280 | 6.87589 | 34.34 |
| 6 | 13.300160 | 6.65718 | 23.76 |
| 7 | 13.910390 | 6.36648 | 60.31 |
| 8 | 14.407420 | 6.14795 | 9.87 |
| 9 | 17.068630 | 5.19493 | 34.10 |
| 10 | 17.386020 | 5.10081 | 16.04 |
| 11 | 17.617300 | 5.03436 | 19.72 |
| 12 | 17.867220 | 4.96450 | 14.63 |
| 13 | 18.357910 | 4.83290 | 24.29 |
| 14 | 18.523090 | 4.79017 | 13.03 |
| 15 | 19.436470 | 4.56708 | 10.08 |
| 16 | 20.783590 | 4.27400 | 49.24 |
| 17 | 21.932050 | 4.05272 | 12.18 |
| 18 | 23.735310 | 3.74875 | 100.00 |
| 19 | 26.370620 | 3.37980 | 23.75 |
| 20 | 26.910000 | 3.31327 | 14.41 |
| 21 | 29.375560 | 3.04055 | 13.59 |

Figure 14:
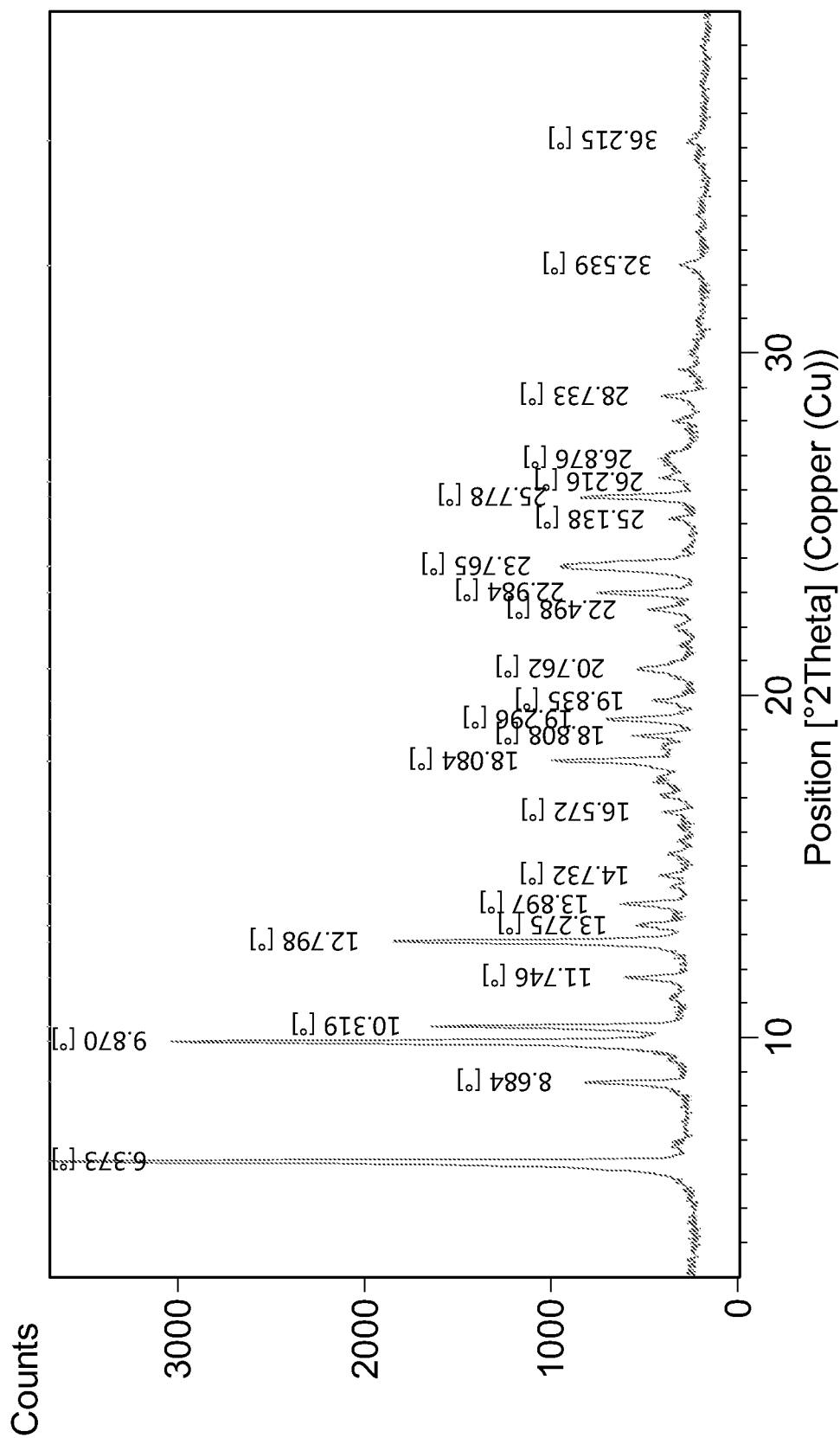
FIG. 14 shows an X-ray diffraction pattern of Crystalline Form J of Compound A.

In another embodiment, the present invention provides Crystalline Form J of Compound A. As shown in FIG. 14, Crystalline Form J's X-ray powder diffraction spectra typically have the following peak diffraction angles (where "spacing" is shown as the "d-value" in FIG. 14):

TABLE 11

X-ray Diffraction Pattern of Crystalline Form J of Compound A

| Peak# | Diffraction angle (2-theta) | Spacing | Relative intensity |
|---|---|---|---|
| 1 | 6.373412 | 13.86831 | 100.00 |
| 2 | 8.683933 | 10.18288 | 16.83 |
| 3 | 9.870480 | 8.96129 | 81.21 |
| 4 | 10.319060 | 8.57272 | 40.38 |
| 5 | 11.745780 | 7.53443 | 10.78 |
| 6 | 12.798320 | 6.91706 | 46.90 |
| 7 | 13.897120 | 6.37253 | 11.41 |
| 8 | 18.084060 | 4.90546 | 22.40 |
| 9 | 19.296010 | 4.60001 | 14.07 |
| 10 | 22.983790 | 3.86960 | 15.54 |
| 11 | 23.764680 | 3.74418 | 20.79 |
| 12 | 25.777610 | 3.45619 | 18.26 |

Figure 15:
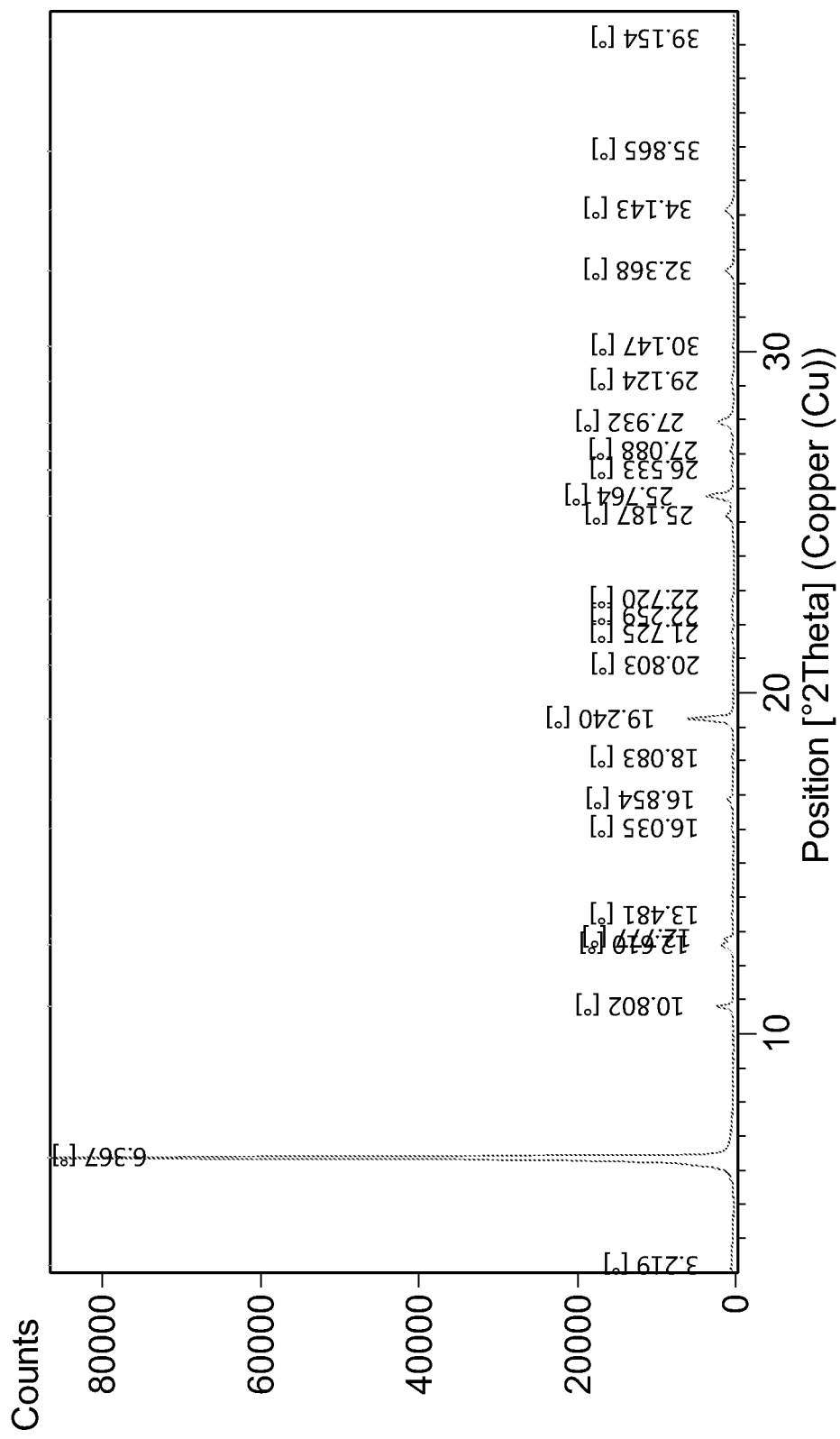
FIG. 15 shows an X-ray diffraction pattern of Crystalline Form K of Compound A.

In another embodiment, the present invention provides Crystalline Form K of Compound A. As shown in FIG. 15, Crystalline Form K's X-ray powder diffraction spectra typically have the following peak diffraction angles (where "spacing" is shown as the "d-value" in FIG. 15):

TABLE 12

X-ray Diffraction Pattern of Crystalline Form K of Compound A

| Peak# | Diffraction angle (2-theta) | Spacing | Relative intensity |
|---|---|---|---|
| 1 | 6.366743 | 13.88282 | 100.00 |
| 2 | 10.801500 | 8.19088 | 2.32 |
| 3 | 12.610210 | 7.01982 | 1.71 |
| 4 | 12.776830 | 6.92865 | 1.31 |
| 5 | 19.240180 | 4.61323 | 6.52 |
| 6 | 25.187350 | 3.53583 | 1.06 |
| 7 | 25.764490 | 3.45792 | 3.92 |
| 8 | 32.368130 | 2.76595 | 1.14 |
| 9 | 34.142730 | 2.62614 | 1.17 |

Figure 16:
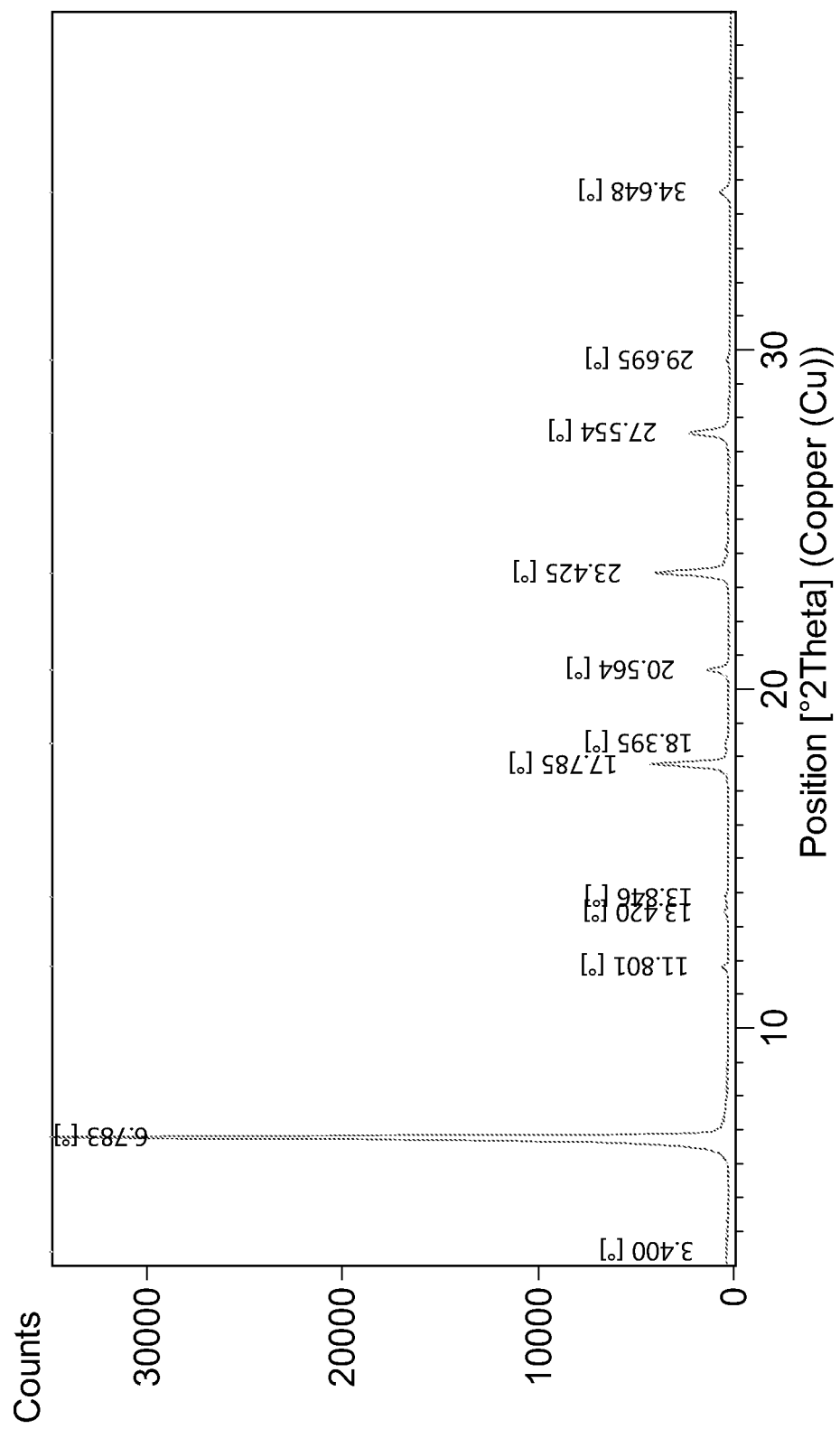
FIG. 16 shows an X-ray diffraction pattern of Crystalline Form L of Compound A.

In another embodiment, the present invention provides Crystalline Form L of Compound A. As shown in FIG. 16, Crystalline Form L's X-ray powder diffraction spectra typically have the following peak diffraction angles (where "spacing" is shown as the "d-value" in FIG. 16):

TABLE 13

X-ray Diffraction Pattern of Crystalline Form L of Compound A

| Peak# | Diffraction angle (2-theta) | Spacing | Relative intensity |
|---|---|---|---|
| 1 | 6.782871 | 13.03202 | 100.00 |
| 2 | 17.785330 | 4.98718 | 11.49 |
| 3 | 20.563890 | 4.31916 | 3.06 |
| 4 | 23.424800 | 3.79773 | 10.86 |
| 5 | 27.554460 | 3.23722 | 5.78 |

For Crystalline Forms A, B, C, C*, D, F, G, H, I, J, K and L described above, only the main peaks (i.e., the most characteristic, significant, unique and/or reproducible peaks) are summarized; additional peaks may be obtained from the diffraction spectra by conventional methods. The main peaks described above can be reproduced within the margin of error (+ or −2 at the last given decimal place, or + or −0.2 at the stated value). Crystalline Forms A, B, C, C*, D, F, G, H, I, J, K and L of Compound A are speculated as anhydrate, hydrate and solvate based on weight loss in TGA (wt %):

TABLE 14

Characterization Summary of Crystal Forms

| Crystalline Form | Weight Loss in TGA (wt %) | Speculated Form |
|---|---|---|
| Form A | 4.7 | Hydrate |
| Form B | 6.0 | Solvate/Hydrate |
| Form C | 8.6 | Hydrate |
| Form C* | 8.9 | Hydrate |
| Form D | 34.5 | Solvate/Hydrate |
| Form E | 38.3 | Solvate/Hydrate |
| Form F | 34.5 | Solvate/Hydrate |
| Form G | 6.5 | Hydrate |
| Form H | 24.8 | Solvate/Hydrate |
| Form I | 1.8 | Anhydrate |
| Form J | 1.1 | Anhydrate |
| Form K | 12.8 | Solvate/Hydrate |
| Form L | 1.8 | Anhydrate |

No melting endotherm was observed for any of the samples before decomposition.

Figure 22:
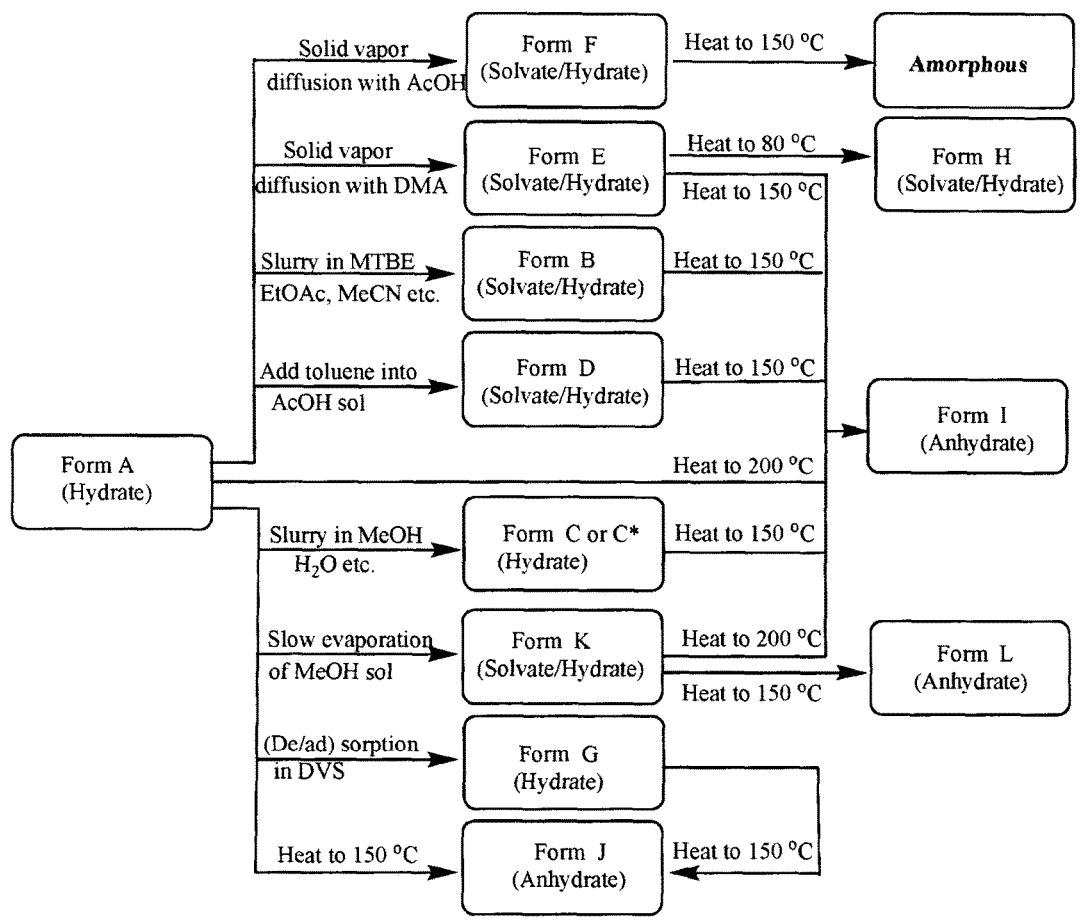
FIG. 22 shows interconversion of Crystalline Forms A, B, C, C*, D, F, G, H, I, J, K and L.

Interconversion of Crystalline Forms A, B, C, C*, D, F, G, H, I, J, K and L is shown in FIG. 22 (Form A was used as the starting material for the polymorph screening work), Among four hydrates (Forms A, C, C* and G), Form C is found to be the most practical and stable crystalline form during manufacturing process of Compound A as API. Heating hydrates or hydrates/solvates at very high temperature causes loss of water or solvents and produces anhydrates, however, it is notable that this process is used to study interconversion of various crystalline forms and may not be practical for the manufacture of Compound A.

In another aspect, the present invention provides Crystalline Forms A, B, C, C*, C, C*, D, F, G, H, I, J, K and L of Compound A in substantial purity. That is, each of the crystalline forms is substantially pure in one particular crystalline form of Compound I and substantially free of other crystalline forms of Compound I. In one embodiment, the present invention provides crystalline form A in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form B in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form C in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form D in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form F in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form G in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher.

In another embodiment, the present invention provides crystalline form H in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form I in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher.

In another embodiment, the present invention provides crystalline form J in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher. In another embodiment, the present invention provides crystalline form K in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher.

In another embodiment, the present invention provides crystalline form L in substantial purity, such as a purity level of 97.0%; 97.5%; 98.0; 98.5%; 98.6%; 98.7%; 98.8%; 98.9%; 99.0%; 99.1%; 99.2%; 99.3%; 99.4%; 99.5%; or higher.

In another aspect, the present invention provides methods for preparing the compound of Formula I, Formula II and Formula III.

In one embodiment, the present invention provides a Crystalline Form C of Compound A Sesqui-Hydrate prepared or purified according to the procedures depicted in the Scheme 1. The new synthetic methods and crystallization/recrystallization processes disclosed herein overcome many issues associated with the processes reported previously, such as the improved optical purity of Compound A free base via formation and recrystallization of the diasteromeric salt with a chiral acid such as (+)-di-p-methylbenzoyl-D-tartaric acid, and provide many advantages over the existing processes. Notably, the methods disclosed herein are especially suitable for reproducible, commercial-scale manufacture of Compound A Sesqui-Hydrate in high quality and good yields.

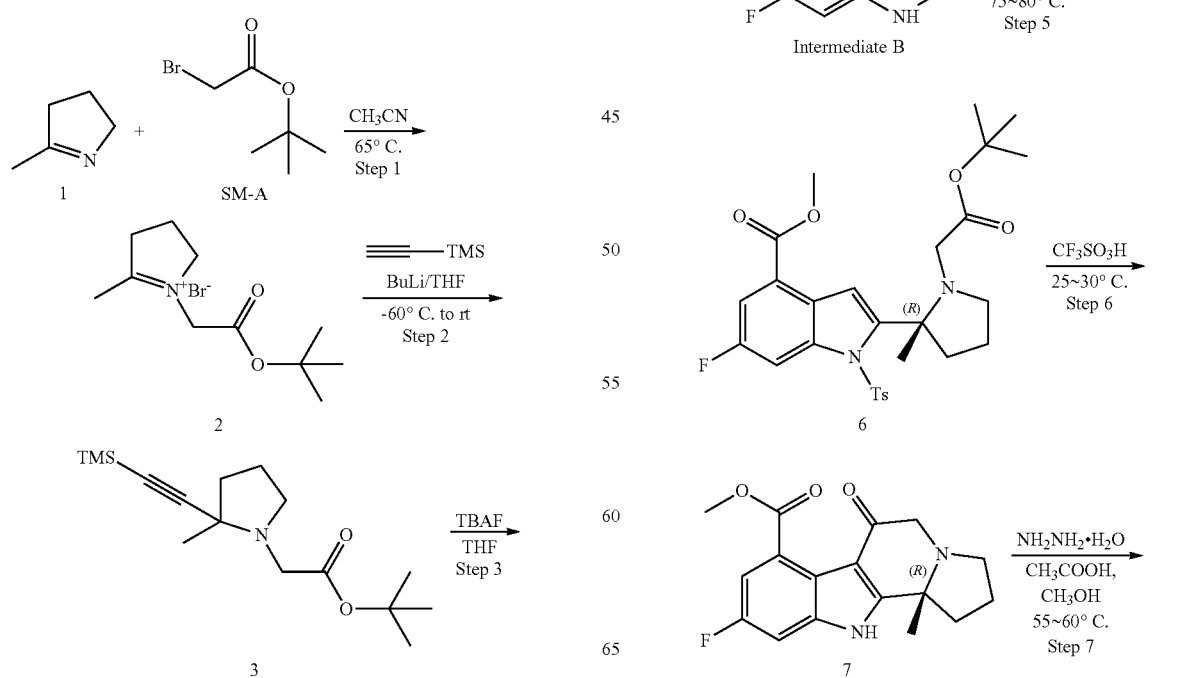

Scheme 1: Synthetic Process of Compound A in a large scale

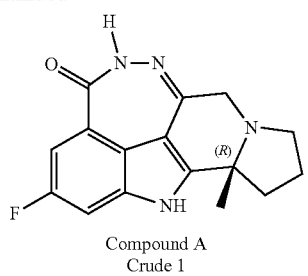

Compound A
Crude 1

As illustrated in Scheme 1, the present application provides a large scale process for preparing Compound A in free base form, comprising the following steps:

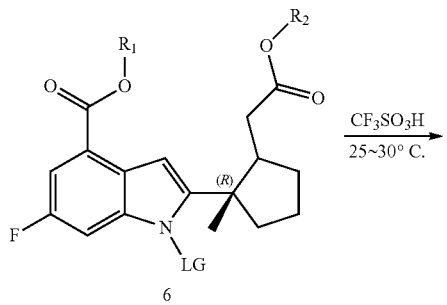

6

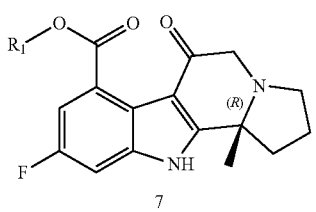

7

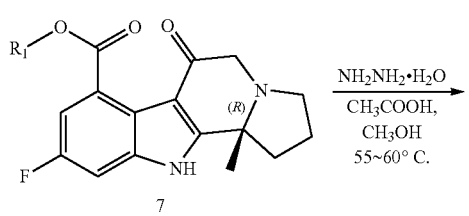

7

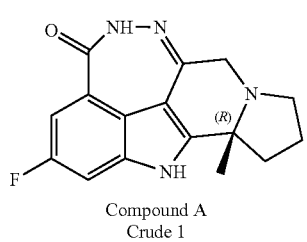

Compound A
Crude 1 wherein $R_1$ and $R_2$ are independently selected from $C_{1-6}$alkyl or halo $C_{1-6}$alkyl; and LG is a leaving group such as Ts.

Scheme 2: Synthetic Process of Compound A Sesqui-Hydrate (Crystalline Form C)

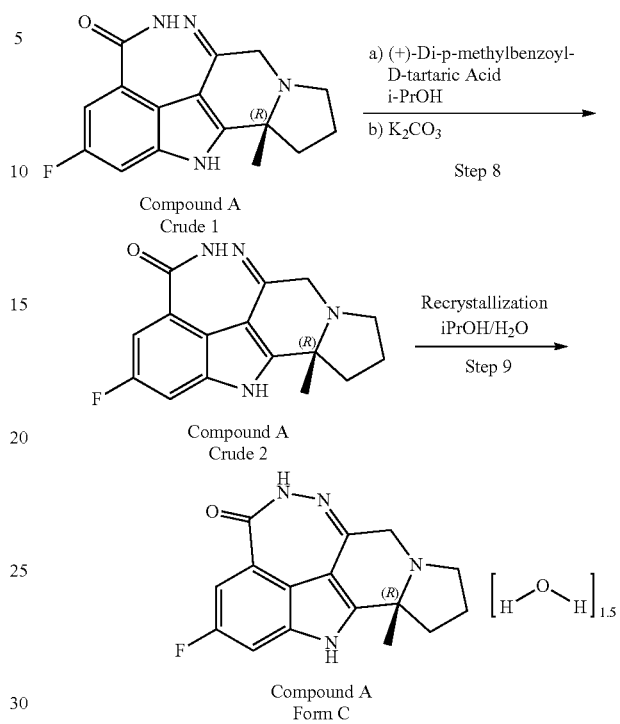

As illustrated in Scheme 2, the present application provides a large scale process for preparing Crystalline Form of Compound A Sesqui-Hydrate, comprising the following steps:

i. reacting the free base of Compound A with a resolving agent (such as a chiral acid, e.g., (+)-di-p-methylbenzoyl-D-tartaric acid) in an appropriate solvent (such as, alcohol, further such as isopropyl alcohol) in the presence of an alkaline to obtain Compound A-crude 2;

ii. recrystallizing Compound A-crude 2 in a mixed solvent such as i-PrOH and water for a certain time and at a certain temperature to obtain the crystalline forms of Compound A.

Crystalline Forms of Compound A can be prepared by the following general method: Crystalline Form C of Compound A Sesqui-Hydrate is heated with a solvent until completely dissolved. After filtration, cooling, crystallization, filtration and drying, the corresponding different crystalline forms are obtained. An example of crystallization process for preparing Crystalline Form A of Compound A is described in the Example 3 (below). The crystallization described above can be carried out in a single solvent, a mixture of organic solvents, or a mixture of water and organic solvent(s). Suitable organic solvents for the crystallization can be selected from, but not limited to, low alkyl alcohols, ketones, ethers, esters, halogenated hydrocarbons, alkanes, halogenated benzene, aliphatic nitrile, and other aromatic solvents. Preferred solvents include, e.g., isopropanol, ethyl acetate, water, N,N-dimethylformamide, methanol, ethanol, acetone, acetonitrile, and mixtures thereof.

The term "low alkyl alcohols" herein includes straight-chain or branched-chain $C_1$-$C_8$, preferably $C_1$-$C_6$, more preferably $C_1$-$C_4$, alkyl alcohols. Specific examples include, but not limited to, methanol, ethanol, isopropanol, and butanol.

The term "about" as used herein, unless indicated otherwise, denotes that a number (e.g., temperature, pH, volume, etc.) can vary within ±10%, preferably within ±5%.

A solvate herein is defined as a compound formed by solvation, for example as a combination of solvent molecules with molecules or ions of a solute. The known solvent molecules include water, alcohols and other polar organic solvents. Alcohols include methanol, ethanol, n-propanol, isopropanol, n-butanol, isobutanol, and t-butanol. Alcohols also include polymerized alcohols such as polyalkylene glycols (e.g., polyethylene glycol, polypropylene glycol). The preferred solvent is typically water. The solvate compounds formed by solvation with water are sometimes termed as hydrates.

The crystallization of the crystalline forms of the present invention can also be conducted in an appropriate solvent system containing at least one solvent by evaporation of solvent, cooling and/or by addition of anti-solvents (solvents that are less able to solubilize Compound A sesqui-hydrate, including but not limited to those described herein) to achieve super-saturation in the solvent system.

Crystallization may be done with or without seed crystals, which is described in the present invention.

The individual crystalline forms disclosed herein were developed under specific conditions dependent on the particular thermodynamic and equilibrium properties of the crystallization process. Therefore, a person skilled in the art will know that the crystals formed are a consequence of the kinetic and thermodynamic properties of the crystallization process. Under certain conditions (e.g., solvent, temperature, pressure, and concentration of the compound), a particular crystalline form may be more stable than another crystalline form (or in fact more stable than any other crystalline forms). However, the relatively low thermodynamic stability of particular crystals may have advantageous kinetic stability. Additional factors other than kinetics, such as time, impurity distribution, stirring, and the presence or absence of seed crystals, etc., may also affect the crystalline form.

In another aspect, the present invention provides pharmaceutical compositions each containing an effective amount of Compound A, in particular Compound A sesqui-hydrate, in any of the above-described Crystalline Forms A, B, C, C*, C**, D, E, F, G, H, I, J, K and L and a pharmaceutically acceptable carrier. The active compound(s) can be 1-99% (by weight), preferably 1-70% (by weight), or more preferably 1-50% (by weight), or most preferably, 5-40% (by weight), of the composition.

The pharmaceutical compositions can be administrated orally in forms such as capsules, tablets, pills, powders, sustained release injection in such form as a sterile solution, suspension or emulsion; through a local treatment form such as paste, cream, or ointment; or via a rectal form such as suppositories. The pharmaceutical compositions may be in a unit dosage form that is suitable for precise dosing applications. In addition, the pharmaceutical compositions may include other active ingredients.

Suitable pharmaceutical carriers include water, various organic solvents and various inert diluents or fillers. If necessary, the pharmaceutical compositions may contain various additives, such as spices, adhesives and excipients. For oral administration, tablets and capsules can contain various excipients such as citric acid, a variety of disintegrant agents such as starch, alginic acids, and some silicates, and a variety of adhesives such as sucrose, gelatin and Arabic gum. In addition, lubricants including magnesium stearate and talc fillers are commonly used in the production of tablets. The same types of solid components can also be used to formulate soft and hard gelatin capsules. When an aqueous suspension is needed for oral administration, the active compound can be mixed with a variety of sweeteners or flavoring agents, pigments or dye combinations. If necessary, a variety of emulsifiers can be employed or suspensions generated; diluents such as water, ethanol, propylene glycol, glycerin, or their combination can be utilized.

The above-described pharmaceutical compositions are preferably administrated orally.

The above-described pharmaceutical compositions are preferably in the capsule or tablet form.

In another aspect, the present invention provides use of the compounds of this invention (i.e., Compound A sesqui-hydrate and any of its above-described Crystalline Forms A, B, C, C*, C**, D, E, F, G, H, I, J, K and L) in the manufacture of medicaments that are useful for the treatment of cancers responsive to inhibition of Parp1 and Parp2.

In one embodiment, the present invention provides use of the compounds of this invention (i.e., Compound A sesqui-hydrate and any of its above-described Crystalline Forms A, B, C, C*, C**, D, E, F, G, H, I, J, K and L) in the manufacture of medicaments that are useful for the treatment or prevention of mammalian pancreatitis, kidney disease, cancer, angiogenesis, or angiogenesis-related diseases.

Compound A sesqui-hydrate and other free base Crystalline Forms A, B, C, C*, C**, D, E, F, G, H, I, J, K and L of this invention can be used to treat or prevent diseases selected from, but not limited to, tumor angiogenesis, chronic inflammatory disease such as rheumatoid arthritis, atherosclerosis, skin diseases such as psoriasis and scleroderma, diabetes-induced skin diseases, diabetic retinopathy, premature retinopathy, age-related degeneration stains, hemangioma, glioma, Kaposi internal tumor, ovarian cancer, breast cancer, lung cancer including small cell lung cancer, pancreatic cancer, lymphoma, prostate, colon and skin tumors, and their complications. Among the mammals mentioned herein, human beings are preferred.

The diseases to be treated by the above-described treatment methods are preferably selected from BRCA1 and BRCA2 mutant tumors such as BRCA1 and BRCA2 mutant breast cancer, ovarian cancer and their complications.

The above-described methods can be applied in combination with any chemical therapy (for examples, TMZ and docetaxel), biological therapy, or radiation therapy.

The dosage of the active ingredient or compound when administered will be determined by the individual needs of the patient to be treated, administration route, severity of disease or illness, dosing schedule, as well as evaluation and judgment of the designated doctor. However, based on the active compound, the preferred range of the effective dosage can be approximately 0.01-320 mg daily per kilogram of body weight; or more preferably 0.1-10 mg per day per kilogram of body weight in single or separate doses.

Another aspect of the present invention is to provide crystalline forms of Compound A for clinical applications. In particular, the present invention relates to clinical treatment with crystalline forms of Compound A with the following treatment options for cancer patients: the dosage of crystalline forms of Compound A selected from the group consisting of Crystalline Form A, B, C, C*, C**, D, E, F, G, H, I, J, K and L can be 1-320 mg/day with the administration frequency being 1-3 times a day; a preferred dosage is 5-240 mg/day with the administration frequency being 1-3 times a day; a more preferred dosage of 10-200 mg/day with the administration frequency being 2 times a day.

The following synthetic methods, specific examples, and efficacy tests further describe certain aspects of the present invention. They shall not limit or restrict the scope of the present invention in any way.

EXAMPLES

The examples below are intended to be exemplary and efforts have been made to ensure accuracy with respect to numbers used (for example, amounts, temperature, etc.), but some experimental errors and deviations should be accounted for within the knowledge of a person skilled in the art. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra and $^{13}$C NMR were recorded on a Varian instrument operating at 400 MHz.

X-ray intensity data from a colorless plate-like crystal were measured at 173(2) K using aBruker APEX-II CCD diffractometer (Cu Kα radiation, λ=1.54178 Å). Polarized light microscopic picture was captured at room temperature.

TGA was conducted using a TA Instruments Q500 TGA. The temperature was calibrated using nickel and the weight using TA-supplied standard weights and verified against calcium oxalate monohydrate dehydration and decomposition.

DSC was performed using a TA instruments Q2000 DSC ramping from 25° C. to desired temperature at a heating rate of 10° C./min using N$_2$ as the purge gas, with pan crimped.

In the following examples, the abbreviations below may be used:
AcOH Acetic acid
ACN Acetonitrile
Aq Aqueous
Brine Saturated aqueous sodium chloride solution
Bn Benzyl
BnBr Benzyl Bromide
CH$_2$Cl$_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
Et$_2$O or ether Diethyl ether
g grams
h or hr hour
HATU O-(7-Azabenzotriazol-1-yl)-N,N,N',N'-tetramethyluronium hexafluorophosphate
HCl Hydrochloric acid
HPLC High-performance liquid chromatography
IPA 2-propanol
i-PrOH Isopropyl alcohol
mg milligrams
mL milliliters
Mmol millimole
MeCN Acetonitrile
MeOH Methanol
Min minutes
ms or MS Mass spectrum
Na$_2$SO$_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography
TMSCl Trimethylsilyl chloride
μL microliters Example 1

Preparation of Compound A in Free Base form and Crystalline Form C of Compound A Sesqui-Hydrate in a Large Scale Step 1: Synthesis of Compound-2

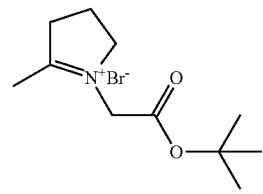

t-Butyl bromoacetate (51.7 Kg) was dissolved in anhydrous acetonitrile (72 Kg). The temperature was raised to 65-75° C., then methyl pyrroline (22 Kg) was added. The reaction mixture was condensed after the reaction was completed, the residual acetonitrile was removed by adding THF and then condensing. After GC showed a complete removal of acetonitrile, more THF was added and stirred. The resulting solid was filtered and collected. 44.1 Kg of off white solid Compound-2 was obtained. $^1$H NMR (400 MHz, DMSO-d6) δ 4.91 (s, 2H), 4.15 (m, 2H), 3.29 (m, 2H), 2.46 (s, 3H),), 2.14 (m, 2H), 1.46 (s, 9H) ppm.

Step 2: Synthesis of Compound-3

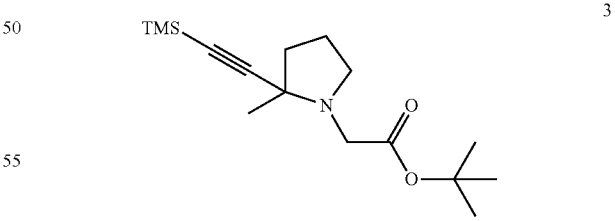

To a cool (−60° C.) solution of trimethylsilyl acetyne (12.4 Kg) in THF was added a solution of n-butyl lithium in hexane (43.4 Kg). After complete addition of n-butyl lithium solution, the resulting mixture was stirred for additional 1-2 h and then the entire solution was transferred into a suspension of Compound-2 (31 Kg) in THF cooled at −60° C. After transfer completion, the resulting mixture was warmed to room temperature and stirred for 1 h. The reaction was quenched with water, extracted with petroleum. The organic phase was washed with brine, dried over sodium sulfate, condensed to give 25.1 Kg of Compound-3. ¹H NMR (400 MHz, DMSO-d6) δ 3.34 (d, J=16.0 Hz, 1H), 3.15 (m, 1H), 2.78 (d, J=16.0 Hz, 1H), 2.27 (m, 1H), 1.93 (m, 1H), 1.68 (m, 3H), 1.41 (s, 9H), 1.24 (s, 3H), 0.13 (s, 9 H) ppm.

Step 3: Synthesis of Compound-4

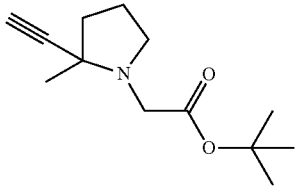

4

To a cool (0-5° C.) solution of 70.1 Kg of Compound-3 in THF was added tetrabutylammonium fluoride (13.3 Kg) in THF. After de-silylation was completed, the reaction was quenched with water, extracted with petroleum (290 Kg) and the organic phase was condensed and passed through a pad of silica gel. The filtrate was condensed to give 48 Kg of Compound-4. ¹H NMR (400 MHz, DMSO-d6) δ 3.36 (d, J=16.0 Hz, 1H), 3.15 (m, 1H), 2.82 (d, J=16.0 Hz, 1H), 2.28 (m, 1H), 1.97 (m, 1H), 1.70 (m, 3H), 1.41 (s, 9H), 1.26 (s, 3H) ppm.

Step 4: Syntheses of Compound-5

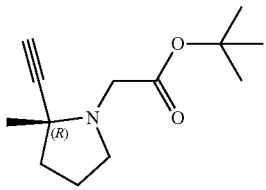

5

A solution of Compound-4 (48 Kg) in THF was warmed to 50-60° C. To the above solution was added a solution of (−)-di-p-methylbenzoyl-L-tartaric acid (69.6 Kg) in THF. The resulting mixture was stirred at 50-60° C. 1-2 h and then gradually cooled to 0-10° C. The resulting salt solid was filtered and re-suspended in methyl tert-butyl ether and heated at 50-60° C. for 1 h. The mixture was gradually cooled to 0-5° C. The resulting solid was filtered to give 13.1 Kg of off-white solid. The solid was treated with aqueous sodium hydroxide, extracted with petroleum, condensed to give 13.1 Kg of Compound-5 (ee≥96%). ¹H NMR (400 MHz, DMSO-d6) δ 3.36 (d, J=16.0 Hz, 1H), 3.15 (m, 1H), 2.82 (d, J=16.0 Hz, 1H), 2.29 (m, 1H), 1.97 (m, 1H), 1.70 (m, 3H), 1.41 (s, 9H), 1.26 (s, 3H) ppm.

Step 5: Syntheses of Compound-6

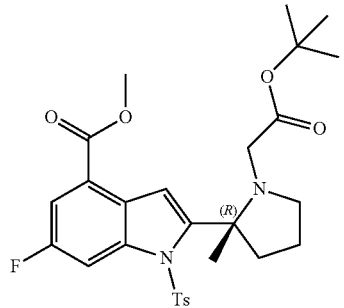

6

Intermediate B (14 Kg), bis(triphenyl)palladium dichloride (0.7 Kg), CuI (0.42 Kg) and tetramethyl guanidine (11.5 Kg) were dissolved in DMF (48.1 Kg). The resulting solution was stirred and de-gassed and then heated under nitrogen. A solution of Compound-5 (9.24 Kg) in DMF (16 Kg) was added dropwise. After coupling, the organic phase was condensed, the residue was stirred with water (145 Kg) and methyl t-butyl ether (104 Kg), the entire mixture passed trough a pad of celite, separated. The organic phase was washed with a solution of thiourea (14 Kg) in water (165 kg) and brine (100 Kg), condensed. The residue was dissolved in a mixture of n-heptane (120 Kg) and ethyl acetate (28 Kg). The solution was mixed with charcoal (1.4 kg), heated at 40-50° C. for 1-2 h, filtered though a pad of silica gel. The filtrate was condensed to give Compound-6 solid (14.89 Kg) and the liquid filtrate (13 Kg heptane solution, contains 1.24 Kg of Compound-6). ¹H NMR (400 MHz, DMSO-d6) δ 7.85 (d, J=9.6 Hz, 1H), 7.55 (m, 3H), 7.32 (m, 2H), 3.87 (s, 3H), 3.37 (d, J=16.0 Hz, 1H), 3.22 (m ,1H), 2.94 (d, J=16.0, Hz, 1H), 2.60 (m, 1H), 2.48 (m, 1H), 2.29 (s, 3h), 2.26 (m,1 H), 1.82 (m, 2H), 1.49 (s, 3H), 1.43 (s, 9H) ppm.

Step 6: Syntheses of Compound-7

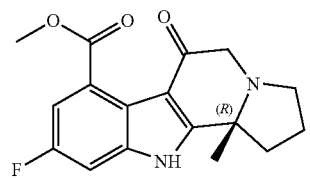

7

The above heptane solution of Compound-6 was added into a cold trifluoromethane sulfonic acid (66.1 Kg) while maintaining the internal temperature below 25° C. Then solid Compound-6 (14.87 Kg) was added batchwise. After complete addition of Compound-6, the reaction mixture was warmed to 25-30° C. and stirred until the reaction was completed. The entire mixture was poured into a solution of sodium acetate (123.5 Kg) in water (240 Kg). pH of the solution was then adjusted to 7-8 by adding solid potassium carbonate (46.1 Kg). The mixture was extracted with dichloromethane (509 Kg), condensed. The residue was mixed with n-heptane (41 Kg), condensed again to give the precipitate which was filtered and washed by n-heptane (8 Kg) and dried. 8.78 Kg of Compound-7 was obtained. ¹H NMR (400 MHz, DMSO-d6) δ 12.30 (s, 1H), 7.35 (dd, J=9.2, 1.6 Hz, 1H), 7.08 (dd, J=9.2, 1.6 Hz, 1H), 3.79 (s, 3H), 3.68 (d, J=17.2 Hz, 1H), 3.21 (d, J=17.2 Hz, 1H), 3.06 (m, 1H), 2.68 (m, 1H), 1.96 (m, 1H), 1.74 (m, 1H), 1.49 (s, 3H) ppm.

Step 7: Syntheses of Compound A-Crude 1

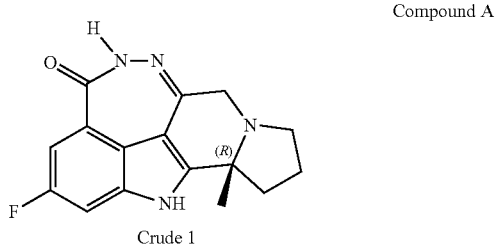

Compound-7 (8.76 Kg) was dissolved in methanol (69 Kg) and internally cooled below 25° C. Acetic acid (9.3 Kg) and hydrazine hydrate (7.4 Kg, 85%) were added while maintaining internal temperature below 25° C. After de-gassed and re-filled with nitrogen (repeated three times), the reaction mixture was stirred at 55-60° C. for 4 h. After a complete reaction, the mixture was mixed with water (29 Kg). The organic phase was condensed and potassium carbonate (12.5 Kg) in water (40 Kg) was added. The resulting solid was filtered, washed with water (18.3 Kg). The solid was slurred with water (110 Kg), centrifuged, dried and slurred with ethanol (9.4 Kg), centrifuged, filtered, washed with ethanol, dried in vacuum to give Compound A-Crude 1 (7.91 Kg). $^1$H-NMR (600 MHz, DMSO-d6) δ 12.0 (s, 1H), 10.2 (s, 1H), 7.31 (dd, 1H, J=9.6, 2.0 Hz), 7.19 (dd, 1H, J=9.6, 2.0 Hz), 3.77 (d, 1H, J=16.4 Hz), 3.34 (d,1H, J=16.4 Hz), 2.97-3.02 (m, 1H), 2.54-2.58 (m, 1H), 2.35-2.40 (m, 1H), 1.90-1.94 (m, 1H), 1.73-1.75 (m, 1H), 1.47 (s, 3H), 1.43-1.45(m, 1H) ppm. MS (ESI) m/e [M+1]$^+$299.

Step 8: Synthesis of Compound A-Crude 2

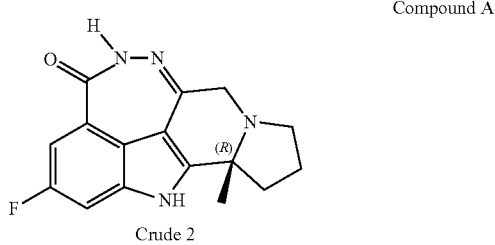

Under nitrogen protection, Compound A (Crude 1) (7.88 Kg) was stirred with isopropanol (422 Kg) and heated at 70-80° C. for 1-2 h until the solid disappeared completely. A solution of (+)-di-p-methylbenzoyl-D-tartaric acid (10.25 Kg) in isopropanol (84.4 Kg) was added. The mixture was stirred for 14-16 h, filtered and washed with isopropanol (16 Kg), dried. The resulting salt was added into a stirred solution of potassium carbonate (6.15 Kg) in water (118 Kg). The precipitate was centrifuged, filtered, washed with water (18 Kg). The solid was slurred with water (110 Kg), centrifuged, dried. The solid was dissolved in THF (75 Kg), active carbon (0.8 Kg) was added. The mixture was degassed and re-protected by nitrogen, stirred and heated at 40-45° C. for 1-2 h, cooled, filtered through celite, condensed to give the solid which was further slurred with ethanol (6.5 Kg), filtered to give 5.6 Kg of Compound A crude 2. $^1$H NMR (400 MHz, DMSO-d6) δ 12.0 (s, 1H), 10.2 (s, 1H), 7.31 (dd, 1H, J=9.6, 2.0 Hz), 7.19 (dd, 1H, J=9.6, 2.0 Hz), 3.77 (d, 1H, J=16.4 Hz), 3.34 (d,1H, J=16.4 Hz), 2.97-3.02 (m, 1H), 2.54-2.58 (m, 1H), 2.35-2.40 (m, 1H), 1.90-1.94 (m, 1H), 1.73-1.75 (m, 1H), 1.47 (s, 3H), 1.43-1.45(m, 1H) ppm. MS (ESI) m/e [M+1]$^+$299.

Step 9: Synthesis of Compound A Sesqui-Hydrate

Formula III

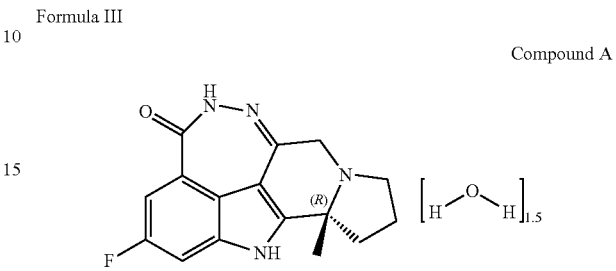

Compound A-Crude 2 (5.3 Kg) was mixed with a solution of isopropanol (41.6 Kg) and water (15.9 Kg). The mixture was degassed and re-protected under nitrogen and then heated to 60° C. and stirred for 2-4 h until the solid was dissolved completely. The temperature was raised to 70-80° C. and water (143 Kg) was added. The resulting mixture was heated to the internal temperature of 70-80° C. and then the heating was stopped but stirred gently for 16 h. The precipitate was filtered, washed with water (19 Kg) and slurred with water (21 kg) for 2 h. The resulting solid was filtered, washed with water (20 Kg). The filtered solid was dried at the temperature below 45° C. for 24-36 h. Compound A sesqui-hydrate (4.22 kg) was obtained with particle sizes of D90=51.51 um, D50=18.62 um, D10=7.63 um. This range of PSD is almost ideal for formulation development.

Figure 17:
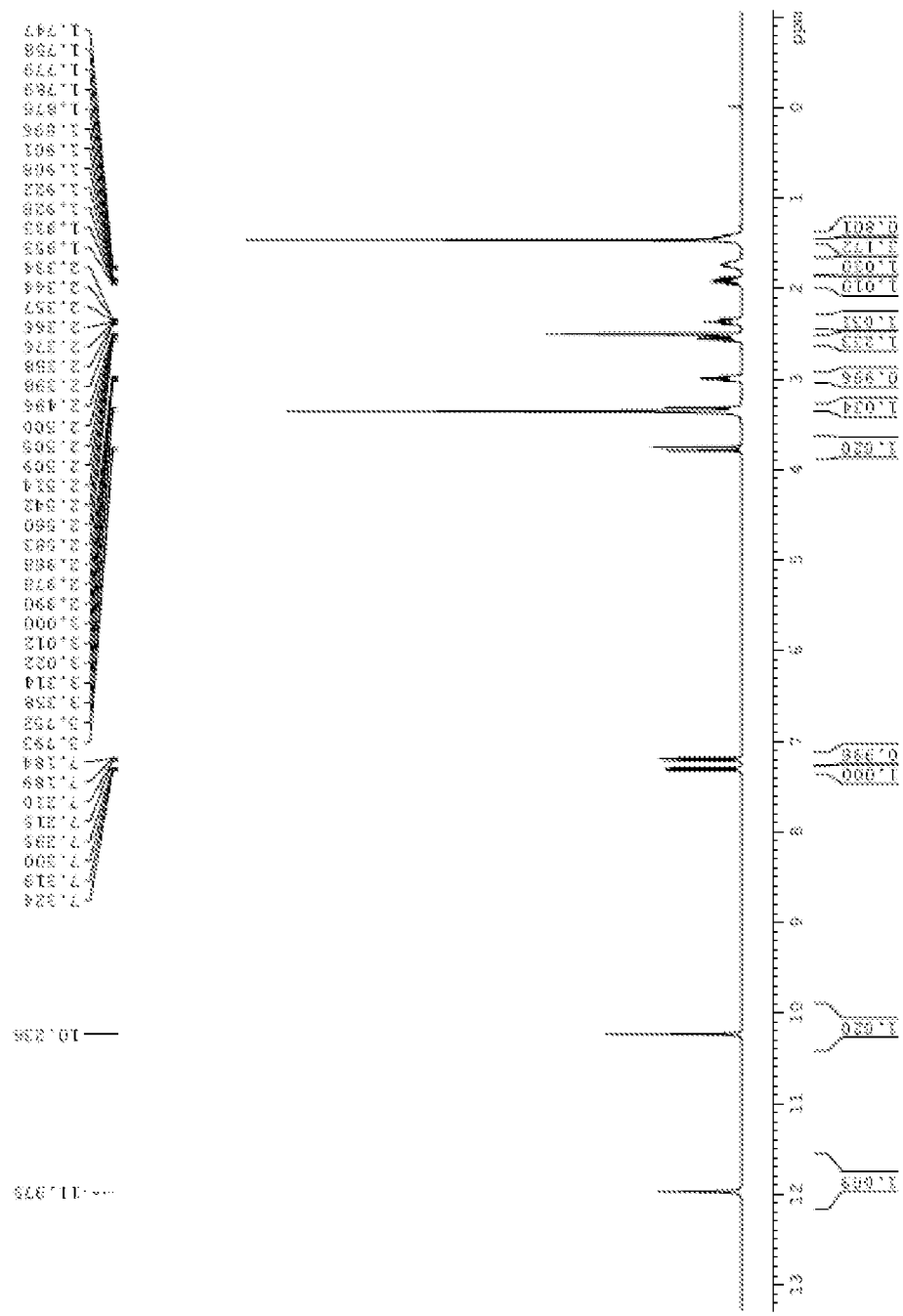
FIG. 17 shows a $^1$H-NMR spectrum of Crystalline Form C of Compound A Sesqui-Hydrate.
Figure 18:
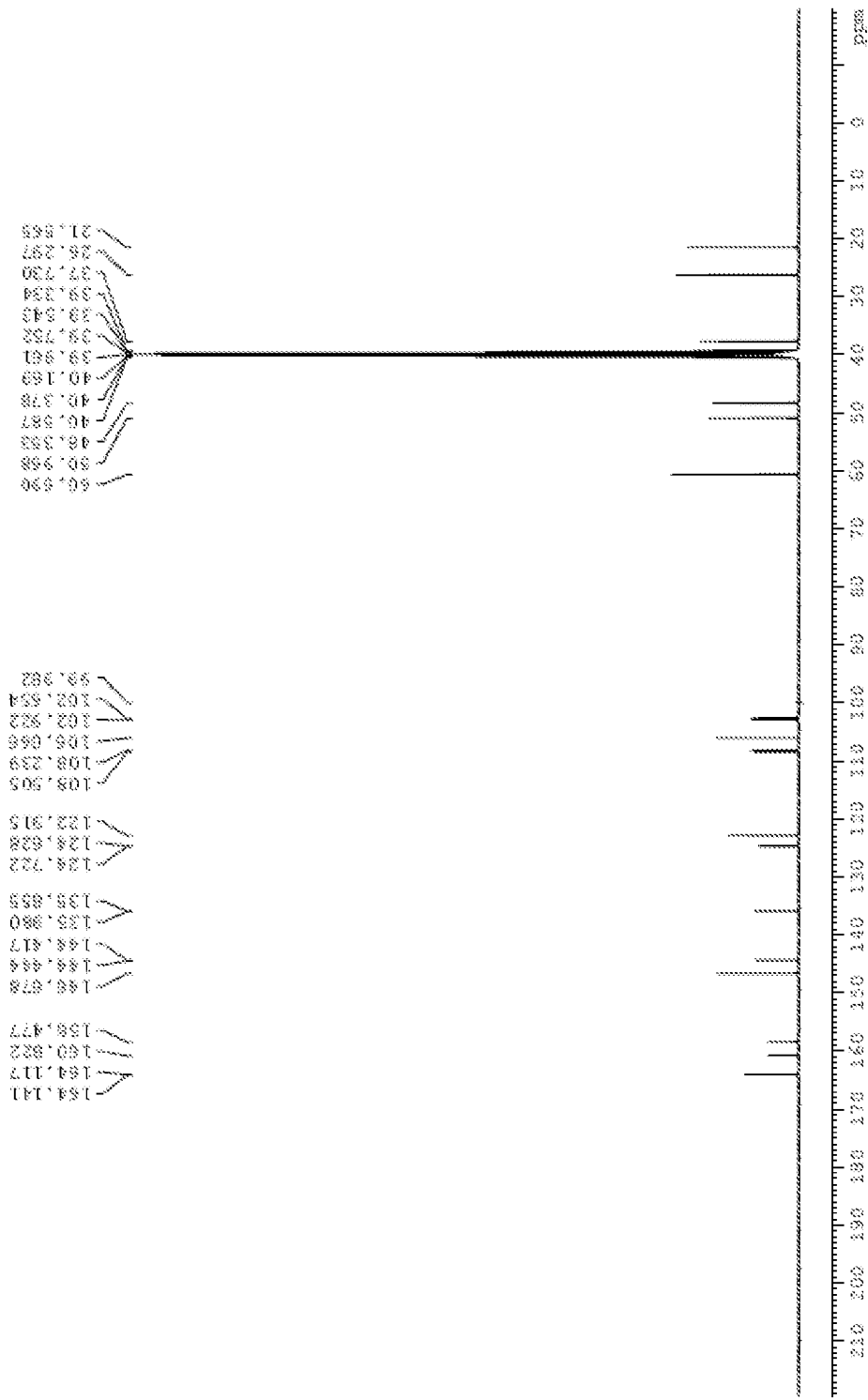
FIG. 18 shows a $^{13}$C-NMR spectrum of Crystalline Form C of Compound A Sesqui-Hydrate.
Figure 19:
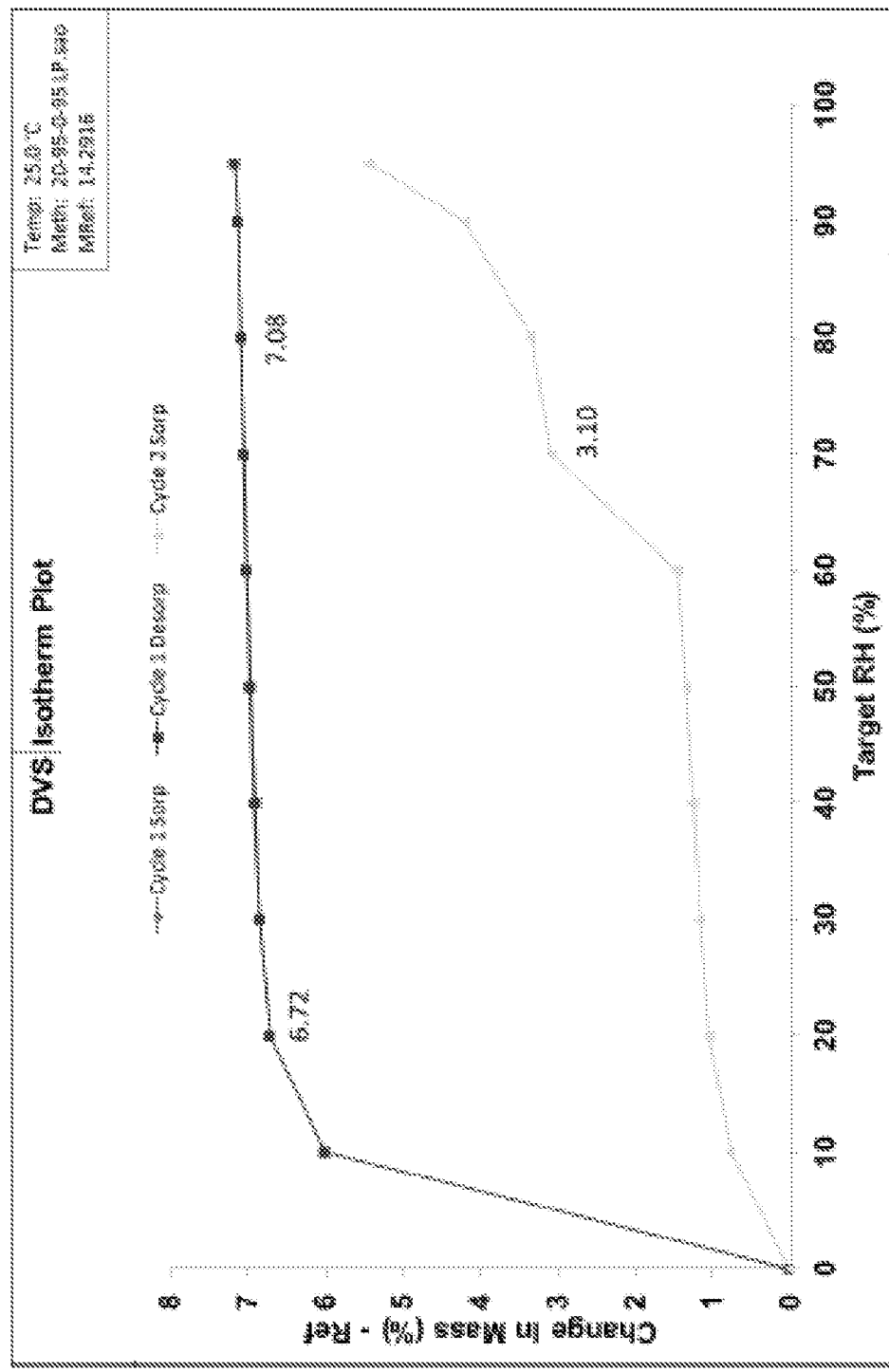
FIG. 19 shows a DVS spectrum of Crystalline Form C of Compound A Sesqui-Hydrate.
Figure 20:
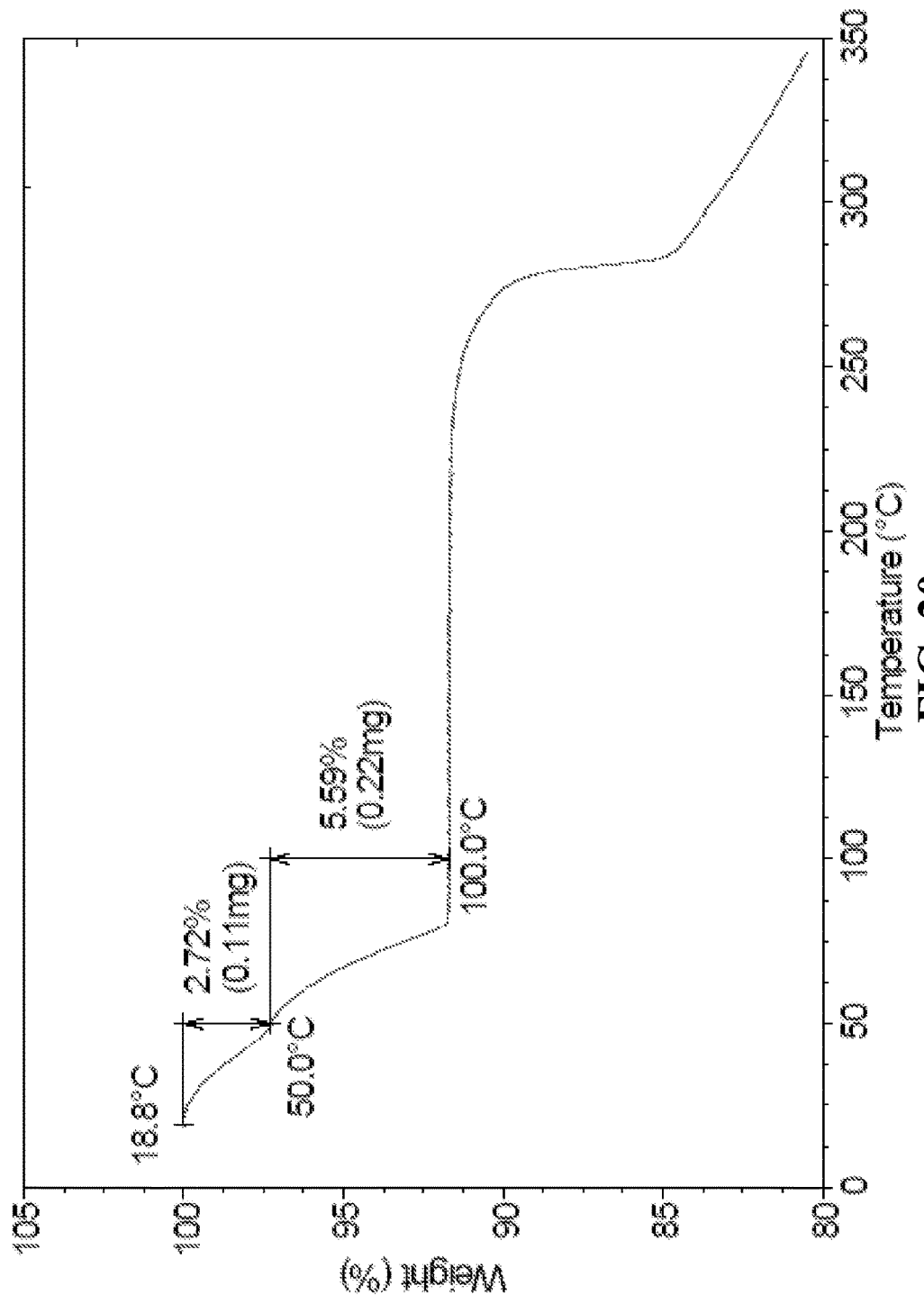
FIG. 20 shows a TGA spectrum of Crystalline Form C of Compound A Sesqui-Hydrate.
Figure 21:
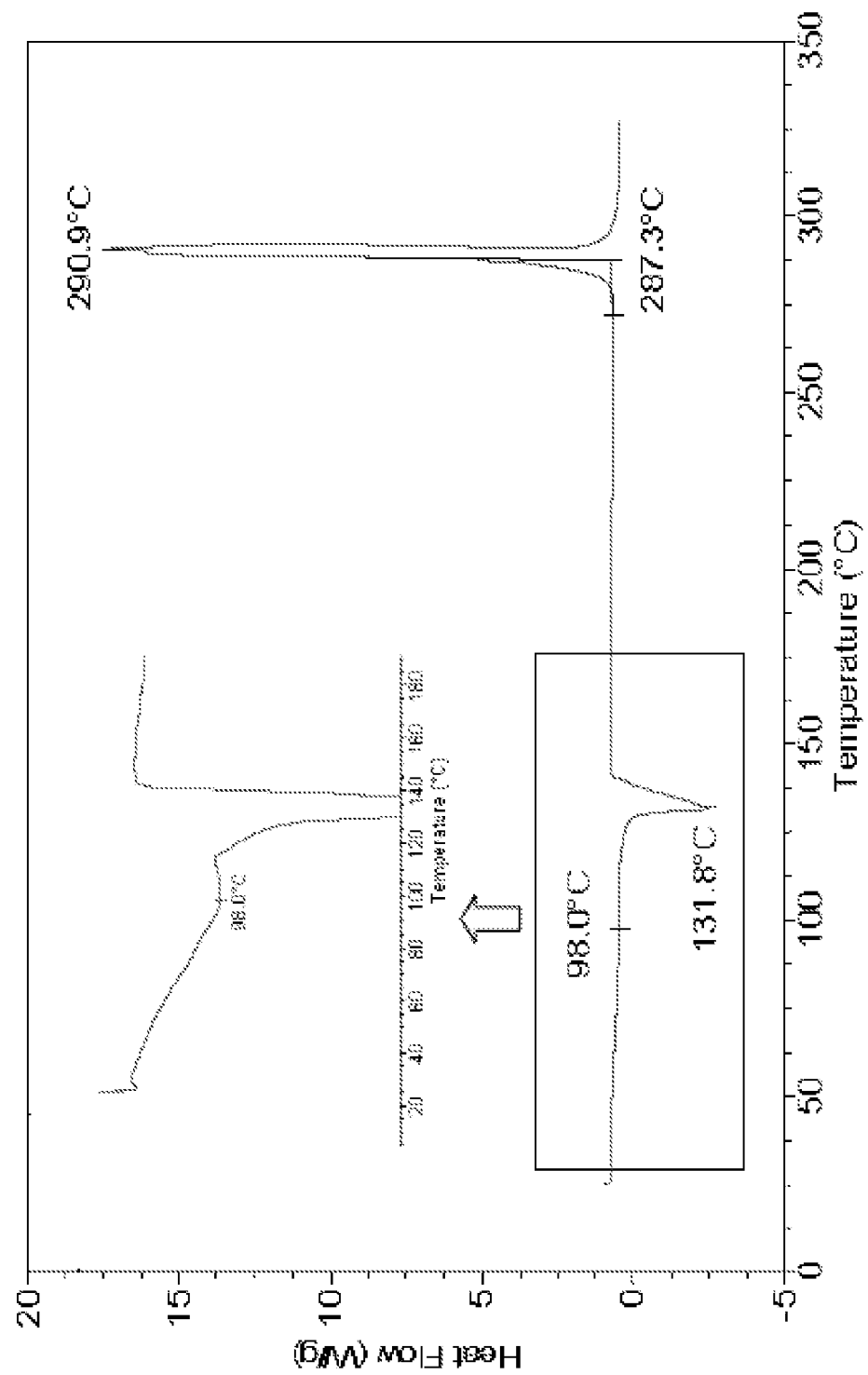
FIG. 21 shows a DSC spectrum of Crystalline Form C of Compound A Sesqui-Hydrate.

The powder X-ray diffraction pattern method was used to characterize the structure of Crystalline Form C, see FIG. 7A. $^1$H-NMR spectra for Crystalline Form C of Compound A Sesqui-Hydrate is shown in FIG. 17. $^{13}$C-NMR spectra for Crystalline Form C of Compound A Sesqui-Hydrate is shown in FIG. 18. DVS spectrum of Crystalline Form C of Compound A Sesqui-Hydrate is shown in FIG. 19. TGA spectrum of Compound A Sesqui-hydrate Crystalline Form C is shown in FIG. 20, wherein 0.5 water molecule is lost at 50° C. and another 1.0 water molecule is lost at 100° C., confirming the molar number of water in the crystalline form is 1.5. DSC spectrum of Compound A Sesqui-hydrate Crystalline Form C is shown in FIG. 21.

The quantitative elemental analysis of Crystalline Form C of Compound A Sesqui-Hydrate is presented in Table 16. The absolute difference of C, H, N content found and calculated is below 0.3% and is consistent with its molecular formula, $C_{16}H_{15}FN_4O \cdot 1.5H_2O$. Analysis was performed in duplicate.

TABLE 16

| Quantitative Elemental Analysis of Crystalline Form C of Compound A Sesqui-Hydrate | | | |
|---|---|---|---|
| Analysis | Theory (%) | Found (%) | Absolute Difference (%) |
| C | 59.07 | 59.05 | 0.02 |
| H | 5.58 | 5.59 | 0.01 |
| N | 17.22 | 17.48 | 0.26 |

The residual levels of all the solvents used in the production of Crystalline Form C of Compound A Sesqui-Hydrate were tested in clinical batch (03035-20131201) and controlled well below ICH standard.

TABLE 17

Residual Solvents

| Residual Solvent | Acceptable Criteria | Residual Level |
| --- | --- | --- |
| Iso-Propanol | NMT 5000 ppm | 194 ppm |
| n-Heptane | NMT 5000 ppm | ND |
| Dichloromethane | NMT 600 ppm | ND |
| Methyl T-Butyl Ether | NMT 5000 ppm | ND |
| Methanol | NMT 3000 ppm | 37 ppm |
| Ethanol | NMT 5000 ppm | 28 ppm |
| Ethyl Acetate | NMT 5000 ppm | ND ppm |
| N,N-Dimethylformamide | NMT 880 ppm | ND ppm |
| Tetrahydrofuran | NMT 720 ppm | 3 ppm |

The water content of Crystalline Form C of Compound A Sesqui-Hydrate was found to be 8.6% (KF method), which is consistent with thereotic water content (8.3% as demonstrated in TGA diagram in FIG. 20) of its molecular formula, $C_{16}H_{15}FN_4O \cdot 1.5H_2O$.

The aqueous solubility of Crystalline Form C of Compound A Sesqui-Hydrate is very small (~0.04 mg/mL), however, its solubility in stomach juice (SGF) is pretty high (~4.5 mg/mL). This dramatic solubility difference makes Crystalline Form C of Compound A Sesqui-Hydrate as a good form of drug substance (API). Recrystallization and slurry of Compound A API can readily be performed in water-alcohol solution, a preferred solvent system for API manufacture. The high solubility in SGF renders Compound A sesqui-hydrate to be dissolved and absorbed in stomach quickly.

Scheme 3: Preparation of Intermediate B:

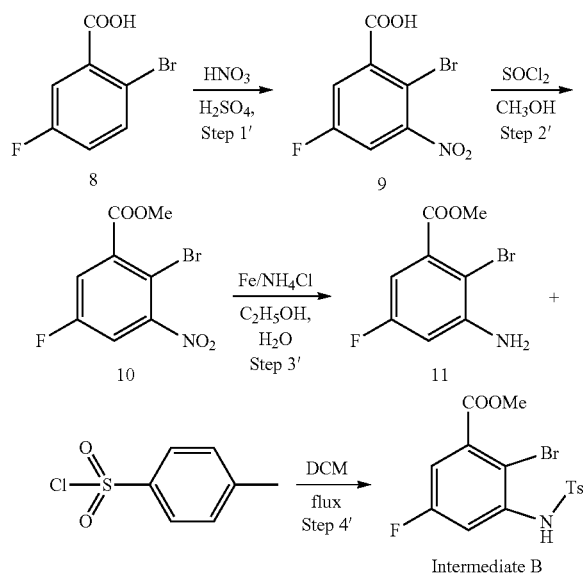

Step 1': Synthesis of Compound-9

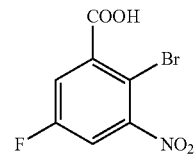

The commercially available Compound-8 (50 Kg) was dissolved in concentrated sulfuric acid (349.5 Kg) and stirred. A mixture of concentrated nitric acid (95%, 24.9 Kg) and concentrated sulfuric acid (50.0 Kg) was added while the internal temperature was controlled between 35-43° C. The reaction mixture was poured into ice-water. The resulting suspension was centrifuged and the solid was collected and slurred with water (245 Kg), centrifuged and dried at 45° C. with a flow of air to give 48.5 Kg of Compound-9.

Step 2': Synthesis of Compound-10

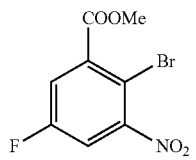

Compound-9 (48.5 Kg) was dissolved in methanol (121.5 Kg) and thionyl chloride (49.5 Kg) was added. After the esterification was complete, the reaction mixture was cooled to 0-5° C. for 2-12 h. The precipitate was centrifuged and filtered, washed with methanol, slurred with water, centrifuged and filtered again, dried to give 26.4 Kg of Compound-10. $^1$H-NMR (600 MHz, DMSO-$d_6$) δ 8.31 (dd, J=8.0, 2.8 Hz, 1H), 7.98 (dd, J=8.0, 2.8 Hz, 1H), 3.91 (s, 3H) ppm.

Step 3': Synthesis of Compound-11

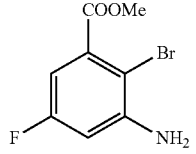

Compound-10 was dissolved in a mixture of ethanol (106 Kg) and water (132 Kg). Ammonium chloride (26.4 Kg) was added, iron powder (26.4 Kg) was then added batchwise. The mixture was stirred at 75-85° C. for 3 h, cooled to RT, extracted with ethyl acetate (236 Kg). The organic phase was washed with aqueous NaHCO3 (230 Kg) and then aqueous sulfate, condensed to give 24 Kg of Compound-11. $^1$H-NMR (600 MHz, DMSO-$d_6$) δ 6.73 (dd, J=8.0, 2.8 Hz, 1H), 6.63 (dd, J=8.0, 2.8 Hz, 1H), 5.92 (s, 2H), 3.82 (s, 3H) ppm.

Step 4': Synthesis of Intermediate B

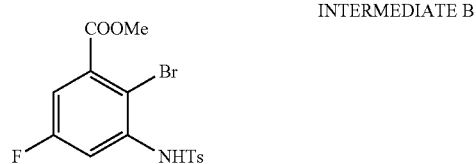

INTERMEDIATE B

Compound-11 (24.6 Kg) was dissolved in a mixture of methylene dichloride (240 Kg) and pyridine (24.3 Kg) and stirred for 30 min. Toluene sulfonyl chloride (18.5 Kg) was added. The mixture was stirred and heated at 38-45° C. for 20-22 h. Water (187 Kg) was added and stirred and separated. The organic phase was washed with concentrated hydrochloric acid (49 Kg) and water (49 Kg), condensed and petroleum was added. A large quantity of precipitate formed. Filtered and dried to give the crude INTERMEDIATE B. The crude product was dissolved in toluene (32 Kg) and heated at 60-65° C. until all the precipitates dissolved completely. The solution was stirred for 20 min and cooled to 5-15° C. and standed still. The suspension was centrifuged and separated. The resulting solid was slurred with a mixture of toluene (24.6 Kg) and petroleum (37 Kg), filtered and washed with petroleum, dried to give the INTERMEDIATE B with good quality. $^1$H-NMR (600 MHz, DMSO-d6) δ 10.27 (s, 1H), 7.69 (m, 2H), 7.45 (m, 3H), 7.18 (dd, J=9.6, 3.2 Hz, 1H) ppm.

The long term stability studies of Crystalline Form C of Compound A Sesqui-Hydrate showed there was no significant chemical purity change occurred when stored at 25° C.° C./60% RH for up to 12 months (Assay w/w: T0=99.1% and T12=99.0%) and at 40° C./75% RH condition for up to 12 months (Assay w/w: T0=99.0% and T12=98.9%). In addition, no crystal form and optical purity changes were observed when stored at 25° C.° C./60% RH for up to 12 months and at 40° C./75% RH condition for up to 12 months.

The solubility study showed Crystalline Form C of Compound A Sesqui-Hydrate was barely soluble in water (0.04 mg/mL), however, it was dissolved in SGF (stomach juice) very well and the solubility of 4.5 mg/mL was obtained.

Crystalline Form C of Compound A Sesqui-Hydrate was found to be slightly hygroscopic.

Example 2

Preparation of Compound A Single Crystalline Form C**

A single crystal growth screening was conducted under 94 different conditions by varying solvent, temperature, and recrystallization methods, from which single crystals suitable for structure determination were obtained by vapor diffusion at room temperature from IPA/water. The crystal structure of Compound A has been successfully determined using a set of diffraction data collected from a single crystal.

Example 3

Preparation of Crystalline Form A of Compound A

Crystalline Form A of Compound A was obtained by recrystallization of Compound A free base in the solution of i-PrOH/H$_2$O.

Crystalline Form A was manufactured by a procedure similar to that in Example 1, i.e., recrystallization from i-PrOH/H$_2$O, while dried in vacuum which caused partial dehydration.

Procedure: Compound A (23 g, 77.2 mmol) was suspended in solvent of i-PrOH/H$_2$O (240 ml/360 ml) and heated to reflux (about 86° C.), stirred at reflux for about 3.0 h until the entire solid was dissolved. The mixture was gradually cooling down (about 1° C./min) to 65° C. with stirring, and crystal seed was added (about 20 mg, 99.1% ee), and then continue to cool down to room temperature, stayed at room temperature overnight (about 16 h). Then mixture was filtered, washed with water (80 mL×2). And the solid was dried in vacuum for 2 h at 40° C. to give title product (18 g) as crystalline crystals. A powder X-ray diffraction pattern method was used to characterize the structure of Crystalline Form A; see FIG. 6. Results showed that Crystalline Form A is a hydrate, and TGA result indicated a weight loss of 4.7 wt % up to 150° C. as shown in Table 14 before. DSC result showed a melting endotherm at 285.0° C. (onset temperature).

Example 4

Preparation of Crystalline Form B of Compound A

A Compound A Free Base Crystalline Form B sample was obtained via slurry Free Base Crystalline Form A in MTBE at RT.

Procedure: 15.1 mg of Form A solid was weighed into a 1.5-mL vial, and 0.3 mL of MTBE was added into the vial to get a suspension. The mixture was stirred at RT magnetically with a speed of 800 RPM for 2 days to obtain Crystalline Form B. A powder X-ray diffraction pattern method was used to characterize the structure of Crystalline Form B; see FIG. 6. TGA result indicated a weight loss of 6.0 wt % up to 150° C. DSC result showed three overlapped endotherms before decomposed at 283.5° C. (onset temperature).

Example 5

Alternative Procedure for Preparation of Crystalline Form C* of Compound A Sesqui-Hydrate Crystalline Form C* was obtained in a laboratory scale via vapor diffusion between 2-methyltetrahydrofuran solution and water. To be distinguished from Crystalline Form C prepared in a large scale in Example 1, this crystalline form prepared in the laboratory scale in Example 5 is referred to as Crystalline Form C* (Crystalline Form C* is also sometimes referred to as Crystalline Form C in a laboratory scale, and Crystalline Form C is also sometimes referred to as Crystalline Form C in a large scale).

18.9 mg of Form A solid was weighed into a 3-mL glass vial and 0.4 mL of 2-methyltetrahydrofuran was added to get a clear solution. The 3-mL vial was sealed into a 20-mL glass vial with 3 mL of water. The system was kept at RT for 2 days, allowing the vapor to interact with solution so as to obtain Crystalline Form C*. A powder X-ray diffraction pattern method was used to characterize the structure of the resultant crystalline form, which is consistent with FIG. 7B. TGA result of this experimental scale indicated a weight loss of 8.9 wt % up to 150° C. DSC result showed two endotherms and an exotherm before decomposed at 281.9° C.

Example 6

Preparation of Crystalline Form D of Compound A

Crystalline Form D of Compound A sample was obtained via adding anti-solvent of toluene into acetic acid solution of Crystalline Form A of Compound A.

Procedure: 16.3 mg of Form A solid was weighed into a 20-mL glass vial. 0.2 mL of acetic acid was added into the vial to get a clear solution. Cloud was observed after stirring at RT. Add 2 mL of toluene into the solution stepwise to induce more precipitation to obtain Crystalline Form D. A powder X-ray diffraction pattern method was used to characterize the structure of Crystalline Form D; see FIG. 8. TGA result indicated a weight loss of 34.5 wt % up to 160° C. DSC result showed three overlapped endotherms before decomposed at 269.5° C.

Example 7

Preparation of Crystalline Form E of Compound A

Crystalline Form E of Compound A sample was prepared via vapor diffusion between Compound A freebase Crystalline Form A solid and DMA vapor.

Procedure: 12.2 mg of Form A solid was weighed into a 3-mL glass vial. The 3-mL vial was sealed into a 20-mL glass vial with 2 mL of DMA. The system was kept at RT for 7 days, allowing the vapor to interact with solid to obtain Crystalline Form E. A powder X-ray diffraction pattern method was used to characterize the structure of Crystalline Form E; see FIG. 9. TGA result indicated a weight loss of 38.3 wt % up to 150° C. (contained molecules of crystal hydrate). DSC result showed two endotherms before decomposed at 277.1° C. (onset temperature).

Example 8

Preparation of Crystalline Form F of Compound A

Crystalline Form F of Compound A sample was prepared via vapor diffusion between Crystalline Form A solid of Compound A and acetic acid vapor.

Procedure: 11.0 mg of Form A solid was weighed into a 3-mL glass vial. The 3-mL vial was sealed into a 20-mL glass vial with 2 mL of acetic acid. The system was kept at RT for 7 days, allowing the vapor to interact with solid to obtain Crystalline Form F. A powder X-ray diffraction pattern method was used to characterize the structure of Crystalline Form F; see FIG. 10. TGA result indicated a two step weight loss of 34.5 wt % up to 160° C. DSC result showed four overlapped endotherms before decomposition.

Example 9

Preparation of Crystalline Form G of Compound A

Crystalline Form G of Compound A sample was prepared via humidity-induced phase transition of Compound A Crystalline Form A during DVS (dynamic vapor sorption) test at 25° C. A powder X-ray diffraction pattern method was used to characterize the structure of Crystalline Form G; see FIG. 11. TGA result indicated a two step weight loss of 6.5 wt % up to 150° C. DSC result showed three overlapped endotherms before decomposed at 284.9° C. (onset temperature).

Example 10

Preparation of Crystalline Form H of Compound A

Crystalline Form H of Compound A sample was prepared via heating Crystalline Form E of Compound A to 80° C. and cooling to RT under protection of nitrogen. A powder X-ray diffraction pattern method was used to characterize the structure of Crystalline Form H; see FIG. 12. TGA result indicated a two step weight loss of 24.8 wt % up to 150° C. DSC result showed two overlapped endotherms before decomposed at 277.9° C. (onset temperature).

Example 11

Preparation of Crystalline Form J of Compound A

Crystalline Form J of Compound A sample was obtained via heating Crystalline Form E of Compound A to 150° C. and cooling to RT under protection of nitrogen. A powder X-ray diffraction pattern method was used to characterize the structure of Crystalline Form I; see FIG. 13. TGA result indicated a weight loss of 1.8 wt % up to 150° C. DSC result showed a decomposition exotherm at 277.0° C. (onset temperature).

Example 12

Preparation of Crystalline Form J of Compound A

Crystalline Form J of Compound A sample was obtained via heating Crystalline Form A of Compound A to 150° C. and cooling to RT under protection of nitrogen. A powder X-ray diffraction pattern method was used to characterize the structure of Crystalline Form J; see FIG. 14. TGA result indicated a weight loss of 1.1 wt % up to 150° C. DSC result showed a decomposition exotherm at 285.1° C. (onset temperature).

Example 13

Preparation of Crystalline Form K of Compound A

Crystalline Form K of Compound A sample was obtained via slow evaporation of Crystalline Form A of Compound A MeOH solution at RT.

Procedure: 18.3 mg of Form A solid was weighed into a 3-mL glass vial, and 1.8 mL of MeOH was added into the vial to get a clear solution. The solution was evaporated at RT to induce precipitation to obtain Crystalline Form K. A powder X-ray diffraction pattern method was used to characterize the structure of Crystalline Form K; see FIG. 15. TGA result indicated a weight loss of 12.8 wt % up to 150° C. DSC result showed endotherm and an exotherm before decomposed at 284.2° C. (onset temperature).

Example 14

Preparation of Crystalline Form L of Compound A

Crystalline Form L of Compound A sample was obtained via heating Crystalline Form K of Compound A to 150° C. and cooling to RT under protection of nitrogen. A powder X-ray diffraction pattern method was used to characterize the structure of Crystalline Form L; see FIG. 16. TGA result indicated a weight loss of 1.8 wt % up to 150° C. DSC result showed an endotherm before decomposed at 281.7° C. (onset temperature).

Efficacy Tests

Test 1: Inhibition and Selectivity of poly(ADP-ribosyl)ation (PARylation) Enzymes by Compound A Sesqui-Hydrate (Crystalline Form C tested)

Biochemical potency of Compound A Sesqui-Hydrate in inhibiting poly(ADP-ribosyl)ation (PARylation) activity of PARP1, PARP2, TNKS1 and TNKS2 was determined by using commercial PARP1/2 Chemiluminescent Assay Kits (BPS Bioscience Inc.) and. GST-tagged-enzymes were expressed and purified from baculovirus infected Sf9 cell (see Table 18 for enzyme constructs). PARP1 and PARP2 enzymes were from the assay kits, while TNKS1 and TNKS2 enzymes were produced in-house. The assays were performed according to the manufacture's instruction. Briefly, H2A and H2B proteins were immobilized on the surface of plates and then incubated with a serial dilution of compounds and the target enzyme for 0.5 hr. Then, biotinylated NAD and DNA (no DNA needed for TNKS1 or TNKS2) were added to the wells to initiate reactions. The biotinylated PARsylation product was measured by chemiluminescence after adding streptavidin-HRP and HRP substrates. The $IC_{50}$s of Compound A sesqui-hydrate were derived from fitting the dose-response % inhibition data to the four-parameter logistic model using Graphpad Prism software.

Table 18 summarizes $IC_{50}$s of Compound A sesqui-hydrate for PARP1, PARP2, TNKS1 and TNKS2 enzymes. As shown in Table 18 Compound A sesqui-hydrate potently inhibits catalytic activity of PARP1 and PARP2, with $IC_{50}$ of 1.3 and 0.92 nM, respectively. It is more than 100-fold weaker in inhibition of TNKS1 and TNKS2 than PARP1 or PARP2.

TABLE 18

INHIBITION OF PARPS BY COMPOUND A SESQUI-HYDRATE IN BIOCHEMICAL ASSAYS

| Enzyme | $IC_{50}$ of Compound A sesqui-hydrate |
| --- | --- |
| Full length PARP1 | 1.3 ± 0.058 nM (n = 3) |
| PARP2 (aa2-583) | 0.92 nM |
| TNKS1 (aa1021-1327) | 0.23 μM |
| TNKS2 (aa667-1166) | 0.14 μM | n: number of determinations;
n = 1 where not specified.

Test 2:1 Intracellular Target Inhibition

HeLa cells were gifted from National Institute of Biological Sciences (Beijing) and maintained in DMEM supplemented with fetal bovine serum (10% FBS), 100 units/mL penicillin and 0.1 mg/mL streptomycin and kept at 95% humidity and 5% $CO_2$ in a 37° C. incubator. Upon incubation with hydrogen peroxide ($H_2O_2$), Intracellular PARP activity was induced and endogenous PAR level was elevated. The assay was performed as follows:

Cells were plated into a 96-well plate with clear bottom and black wall at a density of 5000 cells per well (100 μL). The plates were incubated for 4 hours at 37° C. under 5% $CO_2$ atmosphere, and then incubated with specific concentrations of test compounds (typically 0.01 nM-10 μM). In the following day, $H_2O_2$ solution in PBS (final concentration 200 μM) was added and the plate was kept at 37° C. for 5 minutes. Then the medium was gently removed by plate inversion, and the cells were fixed by ice-cold MeOH at −20° C. for 20 minutes. After removal of the fixative and repeated wash with PBS, the detection buffer (50 μL/well, containing PBS, Tween (0.1%), and BSA (1 mg/mL)) together with the primary PAR mAb (Alexis ALX-804-220, 1:2000), the secondary anti-mouse Alexa Fluor 488 antibody (Molecular Probes A11029, 1:2000), and nuclear dye DAPI (Molecular Probes D3571, 150 nM) were added and incubation at 4° C. in the dark overnight. After removal of solution and repeated wash with PBS, the PAR polymer level was estimated by ArrayScan VTI (ThermoFisher). Percent inhibition was determined on the basis of the residual enzyme activity in the presence of increasing PARP inhibitor concentration. $IC_{50}$ values were calculated by fitting dose-dependent data to the four-parameter logistic model using XLfit software.

Under these conditions, Crystalline Form C of Compound A Sesqui-Hydrate inhibited intracellular PAR formation with an $IC_{50}$ of 0.24 nM and was more potent than veliparib and olaparib, which had cellular PAR formation $IC_{50}$s of 2.66 nM and 0.47 nM, respectively.

TABLE 19

INHIBITION OF CELLULAR PAR FORMATION IN HYDROGEN PEROXIDE PRE-TREATED HELA CELLS.

| | $IC_{50}$ (nM) in PARylation assay |
| --- | --- |
| Olaparib | 0.47 ± 0.13 (n = 10) |
| Veliparib | 2.66 ± 0.66 (n = 10) |
| Compound A sesqui-hydrate | 0.24 ± 0.10 (n = 10) |

Test 3:1 Synthetic Lethality of Cancer Cells Killing

MDA-MB-231 cells that is not BRCA gene mutant or other homologous recombination deficient were maintained in DMEM supplemented with fetal bovine serum (10% FBS), 100 units/ml penicillin and 0.1 mg/ml streptomycin. BRCA1-deficient cell line MDA-MB-436 was maintained in RPMI-1640 supplemented with 10% FBS, 100 units/ml penicillin and 0.1 mg/ml streptomycin. Both two cell lines were kept at 95% humidity and 5% $CO_2$ in a 37° C. incubator.

The number of tumor cells seeded per well of a 96-well plate was optimized for each cell line to ensure logarithmic growth over the 7 days treatment period. Cells were left to attach for 16 hours and then treated with specific concentrations of test compounds. Following a 7-day exposure to the compound, the growth-inhibitory activity of compounds was determined using CellTiter-Glo luminescent cell viability assay (Promega). Luminescent signal was measured using PHERAstar FS reader (BMG Labtech). Cell viability was expressed as relative to mock treatment control. $EC_{50}$ values for growth inhibition were calculated by fitting dose-dependent data to the four-parameter logistic model using XLfit software.

Under these conditions, MDA-MB-231 of which BRCA gene is widetype was relatively resistant to Compound A with $EC_{50}$s about 9 μM. In contrast, tumor cell lines that was BRCA1-deficient (MDA-MB-436) was profoundly sensitive to Compound A. Compound A was shown to be more potent than veliparib and similar to olaparib in the tumor cells tested.

TABLE 20

SELECTIVE KILLING OF TUMOR CELLS WITH BRCA1 OR BRCA2 MUTATIONS

| Cell Line | Olaparib | Veliparib | Compound A |
| --- | --- | --- | --- |
| MDA-MB-231 | ~5000 | >10000 | ~9000 |
| MDA-MB-436 (BRCA1 Deficient) | 21 ± 7 | 820 ± 300 | 41 ± 15 |

Test 5:1 In Vivo Pharmacology of Crystalline Form C of Compound A Sesqui-Hydrate The in Vivo pharmacodynamics activity (PD) of Compound A on PARP was evaluated in BALB/c nude mice bearing subcutaneous human MDA-MB-436 (BRCA1 mutant) breast cancer. In addition, the relationship between Compound A concentration (PK, pharmacokinetics) in plasma and tumor tissues and its effect on PARylation (PD, pharmacodynamics) was investigated in this xenograft model. Oral administration of Compound A resulted in time-dependent and dose-dependent inhibition of PARylation in MDA-MB-436 breast cancer xenografts in mice. Inhibition of PARylation in the tumor tissues correlates well with tumor drug concentrations of Compound A. Potent inhibition of PARylation was observed at 4 hours after single oral dose of Compound A at 0.34 mg/kg or higher. At 5.45 mg/kg, Compound A induced a strong and sustained PARylation inhibition in MDA-MB-436 tumor tissues. Compound A induced a dose-dependent inhibition on PAR levels in MDA-MB-436 xenograft at 4 hours after single oral administration of 0.17 to 10.9 mg/kg of Compound A. At 5.45 mg/kg, Compound A induced rapid and potent inhibition on PAR levels. The PARylation inhibition was 98% at 0.5 hour after treatment. This inhibition remained at a high level (>80%) through the first 12 hours but was back to 53% at 24 hours. These data support BID dosing in efficacy studies in mouse xenograft models. Both dose titration and time course study suggested that Compound A concentration in tumor tissues needs to be over 0.5 µmol/kg to achieve at least 80% PARylation inhibition.

The in vivo efficacy of Compound A was explored in H209 SCLC xenograft model to evaluate the combination effect of Compound A and Temozolomide (TMZ), a DNA alkylating agent. TMZ single agent was quite effective in this model. One cycle of treatment resulted in all animals tumor-free. However, resistance occurred quickly during the second cycle. Combination of Compound A and TMZ significantly delayed resistance without additional toxicity. Tumors remained sensitive to the combination treatment after multiple cycles. In order to investigate whether Compound A could overcome the TMZ resistance, TMZ-resistant (TR) H209 tumors were generated by treating the H209 tumors with multiple cycles of TMZ in vivo. The derived H209-TR lines remained sensitive to the combination of Compound A and TMZ in this xenograft mouse model. Compound A has significant brain penetration, making it attractive for combining with TMZ in treating brain tumors or tumors with brain metastasis. Mice with established intracranial H209 xenografts were used to further investigate the combination activity of Compound A and TMZ on SCLC in brain. Addition of Compound A significantly prolonged animal survival compared to TMZ single agent in this intracranial model.

Test 6:1 Toxicology of Compound A Sesqui-Hydrate (Crystalline Form C)

The nonclinical toxicity profile of Compound A was characterized in both rats and dogs in single and repeat dose studies up to 28 days. The adverse effects included decrease in body weights or body weight gain and food consumption; decrease in WBC, NEUT, LYMP, RBC, HGB, HCT and APTT; and increase in PLT. The bone marrow was considered to be the major target organ and the severity of histopathological changes ranged from minimal to marked. The toxicity was dose dependent, correlated with systemic exposure and reversible after 28-day recovery phase. Compound A showed no apparent impact on hERG current with $IC_{50}$=25.97 µM. No mutagenicity was noted in an Ames assay. In summary, the available toxicological data are adequate to support the clinical development of Compound A on late stage and advanced cancer patients in phase I study. The toxicity could be monitored and manageable clinically.

Test 7: Pharmacokinetics of Compound A Sesqui-Hydrate Crystalline Form C

The species used for the pharmacokinetic studies were rat and dog. Compound A had good to excellent oral bioavailability (>40%) in both species. Elimination half-lives ranged from 3.1 to 5.0 hours in rats and 1.5 to 2.5 hours in dogs after oral administration. Clearance was moderate in both rats (8.67-15.2 mL/min/kg) and dogs (18.3-18.5 mL/min/kg). Steady state volume of distribution in rats and dogs was 2.4 L/kg and 1.9 L/kg, respectively. There was no accumulation of Compound A following multiple oral dosing in both species.

Test 8: ADME of Crystalline Form C of Compound A Sesqui-Hydrate

Plasma protein binding (PPB) for Compound A was 95.7%, 88.9%, 79.0%, 84.9% and 85.0% in human, monkey, dog, rat, and mouse plasma, respectively. After oral administration in rats, Compound A was detected in all organs checked. The drug concentrations reached maximum at 0.25 to 1 hour post-dosing and decreased to less than 10% of the peak concentration at 24 hours post-dosing.

Compound A was metabolized slowly in human, dog, rat, and mouse liver microsomes, while quickly in monkey liver microsomes, with a total of 5 metabolites (M1, M2, M3, M4 and M5) identified. Six metabolites, M1, M2, M3, M5, M6 and M7, were observed in the feces, plasma, urine and bile of the rat after oral administration. Compound A was primarily excreted in feces. The accumulative excretion amounts of Compound A in feces were 15% to 20% (up to 48 hours) after oral administration. Less than 1% of Compound A was excreted in urine and bile in rats.

CYP3A was the major CYP isoform responsible for Compound A metabolism while CYP2C8 contribute to Compound A metabolism to a lesser extent. Compound A is a moderate inhibitor for CYP2C9 ($IC_{50}$=6.48 µM) while its $IC_{50}$s for other CYP isozymes are all larger than 10 µM. Compound A is not an inducer of human CYP1A2, CYP2B6 and CYP3A.

Test 9: Clinical Trials

Using Crystalline Form C of Compound A Sesqui-Hydrate to prepare capsules, a Phase I clinical safety study was completed on 25 subjects administered bid doses of 2.5, 5, 10, 20, 40, 80 and 120 mg. The results showed that 2.5-120 mg bid doses were safe and well tolerated. Compound A treatment caused partial or complete responses in BRCA1/2 mutant ovary cancer patients. These preliminary data demonstrated that Compound A Sesqui-Hydrate (Crystalline Form C) was effective in the treatment of BRCA1/2 mutant or HR-deficient cancers.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

What is claimed is:

1. A compound of Formula I,

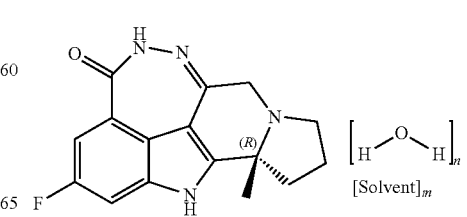

Formula I wherein n is a number from 0.0 to 2.0; m is a number from 0.0 to 20.0; and wherein the solvent is formed by solvation of solvent selected from isopropanol, ethanol, methanol, acetone, THF, 1,4-dioxane, acetic acid, acetonitrile, water, or a combination thereof;

wherein the compound has:

a) a Crystalline Form D, which has a powder X-ray diffraction pattern comprising three or more diffraction peaks having 2θ angle values independently selected from the group consisting of: 5.7±0.2, 6.4±0.2, 6.8±0.2, 9.3±0.2, 9.8±0.2, 10.3±0.2, 11.5±0.2, 12.4±0.2, 12.9±0.2, 13.4±0.2, 13.9±0.2, 17.8±0.2, 18.3±0.2, 18.8±0.2, 18.9±0.2, 23.7±0.2, 25.0±0.2, 25.7±0.2, 25.9±0.2, and 26.7±0.2 degrees; or b) a Crystalline Form E, which has a powder X-ray diffraction pattern comprising three or more diffraction peaks having 2θ angle values independently selected from the group consisting of: 6.2±0.2, 8.6±0.2, 9.5±0.2, 11.0±0.2, 11.5±0.2, 12.0±0.2, 12.5±0.2, 13.4±0.2, 13.8±0.2, 14.4±0.2, 14.7±0.2, 15.1±0.2, 15.3±0.2, 16.2±0.2, 16.9±0.2, 17.9±0.2, 18.3±0.2, 19.0±0.2, 19.5±0.2, 20.1±0.2, 21.3±0.2, 22.2±0.2, 22.9±0.2, 23.3±0.2, 24.2±0.2, 24.6±0.2, 25.1±0.2, 25.7±0.2, 26.3±0.2, 27.0±0.2, 27.4±0.2, and 30.9±0.2 degrees; or c) a Crystalline Form F, which has a powder X-ray diffraction pattern comprising three or more diffraction peaks having 2θ angle values independently selected from the group consisting of: 5.2±0.2, 6.3±0.2, 7.7±0.2, 9.7±0.2, 10.4±0.2, 11.8±0.2, 13.7±0.2, 15.6±0.2, 17.5±0.2, 18.0±0.2, 19.5±0.2, 20.2±0.2, 21.7±0.2, 23.1±0.2, 24.7±0.2, 25.3±0.2, and 27.3±0.2 degrees; or d) a Crystalline Form H, which has a powder X-ray diffraction pattern comprising four or more diffraction peaks having 2θ angle values independently selected from the group consisting of: 9.5±0.2, 12.0±0.2, 13.5±0.2, 15.4±0.2, 17.0±0.2, 19.0±0.2, 23.0±0.2, 24.2±0.2, 27.0±0.2, 27.4±0.2, 31.0±0.2, 34.7±0.2, and 34.8±0.2 degrees; or e) a Crystalline Form K, which has a powder X-ray diffraction pattern comprising three or more diffraction peaks having 2θ angle values independently selected from the group consisting of: 6.4±0.2, 10.8±0.2, 12.6±0.2, 12.8±0.2, 19.2±0.2, 25.2±0.2, 25.8±0.2, 32.4±0.2, and 34.1±0.2 degrees; or f) a Crystalline Form I, which has a powder X-ray diffraction pattern comprising four or more diffraction peaks having 2θ angle values independently selected from the group consisting of: 9.8±0.2, 10.0±0.2, 11.1±0.2, 11.7±0.2, 12.9±0.2, 13.3±0.2, 13.9±0.2, 14.4±0.2, 17.1±0.2, 17.4±0.2, 17.6±0.2, 17.9±0.2, 18.4±0.2, 18.5±0.2, 19.4±0.2, 20.8±0.2, 21.9±0.2, 23.7±0.2, 26.4±0.2, 26.9±0.2, and 29.4±0.2 degrees; or g) a Crystalline Form J, which has a powder X-ray diffraction pattern comprising four or more diffraction peaks having 2θ angle values independently selected from the group consisting of: 6.4±0.2, 8.7±0.2, 9.9±0.2, 10.3±0.2, 11.7±0.2, 12.8±0.2, 13.9±0.2, 18.1±0.2, 19.3±0.2, 23.0±0.2, 23.8±0.2, and 25.8±0.2 degrees.

2. A hydrate of (R)-2-fluoro-10a-methyl-7,8,9,10,10a,11-hexahydro-5,6,7a,11-tetraazacyclohepta[def]cyclopenta[a]fluoren-4(5H)-one free base:

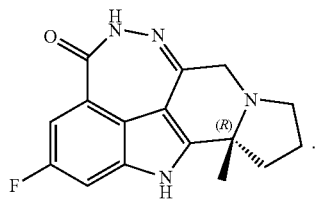

3. The compound of claim 2, which is a crystalline sesqui-hydrate of (R)-2-fluoro-10a-methyl-7,8,9,10,10a,11-hexahydro-5,6,7a,11-tetraazacyclohepta[def]cyclopenta[a]fluoren-4(5H)-one having the structure of Formula III:

Formula III

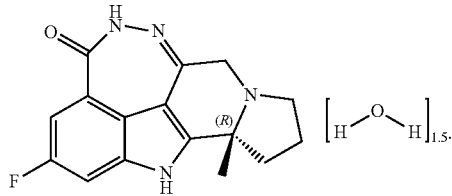

4. The compound of claim 3 in Crystalline Form C**, which is a single crystal as substantially illustrated in FIGS. 1, 2, 3, and/or 4.

5. The compound of claim 2,
a) having Crystalline Form A, which has a powder X-ray diffraction pattern comprising three or more diffraction peaks having 2θ angle values independently selected from the group consisting of: 6.3±0.2, 8.5±0.2, 8.6±0.2, 9.9±0.2, 10.4±0.2, 11.0±0.2, 11.1±0.2, 12.6±0.2, 12.8±0.2, 14.7±0.2, 18.0±0.2, 18.1±0.2, 20.1±0.2, 21.4±0.2, 22.2±0.2, 24.6±0.2, 25.7±0.2, and 30.0±0.2 degrees; or b) having Crystalline Form G, which has a powder X-ray diffraction pattern comprising three or more diffraction peaks having 2θ angle values independently selected from the group consisting of: 6.3±0.2, 8.6±0.2, 9.6±0.2, 10.3±0.2, 11.0±0.2, 12.6±0.2, 17.5±0.2, and 25.4±0.2 degrees; or c) having Crystalline Form B, which has a powder X-ray diffraction pattern comprising three or more diffraction peaks having 2θ angle values independently selected from the group consisting of: 6.3±0.2, 8.7±0.2, 11.1±0.2, 12.6±0.2, 14.5±0.2, 14.8±0.2, 15.2±0.2, 18.0±0.2, 23.9±0.2, 25.3±0.2, and 25.8±0.2 degrees.

6. The compound of claim 2 having Crystalline Form C, which has a powder X-ray diffraction pattern comprising three or more diffraction peaks having 2θ angle values independently selected from the group consisting of: 5.3±0.2, 6.3±0.2, 6.5±0.2, 6.9±0.2, 8.7±0.2, 10.6±0.2, 11.1±0.2, 11.6±0.2, 12.6±0.2, 13.1±0.2, 13.7±0.2, 14.4±0.2, 14.8±0.2, 15.1±0.2, 15.9±0.2, 16.2±0.2, 17.3±0.2, 18.0±0.2, 18.7±0.2, 19.0±0.2, 19.4±0.2, 20.2±0.2, 20.6±0.2, 21.0±0.2, 2±0.2, 21.5±0.2, 22.3±0.2, 22.7±0.2, 23.4±0.2, 23.8±0.2, 24.3±0.2, 24.7±0.2, 25.3±0.2, 25.7±0.2, 26.1±0.2, 26.4±0.2, and 27.4±0.2 degrees.

7. The compound of claim 2 having Crystalline Form C*, which has a powder X-ray diffraction pattern comprising three or more diffraction peaks having 2θ angle values independently selected from the group consisting of: 6.1±0.2, 6.3±0.2, 6.9±0.2, 8.5±0.2, 11.1±0.2, 11.6±0.2, 13.2±0.2, 14.5±0.2, 15.2±0.2, 16.3±0.2, 18.1±0.2, 20.3±0.2, 22.5±0.2, 24.8±0.2, 26.1±0.2, 26.6±0.2, and 27.7±0.2 degrees.

8. The compound of claim 6, wherein the compound has a crystalline form which is substantially Crystalline Form C.

9. The compound of claim 1, having a powder X-ray diffraction pattern substantially similar to a pattern selected from the group consisting of FIGS. 8, 9, 10, 12, 13, 14, 15, and 16.

10. A method for preparing a crystalline form of a hydrate, an anhydrate or a solvate/hydrate of (R)-2-fluoro-10a-methyl-7,8,9,10,10a,11-hexahydro-5,6,7a,11-tetraazacyclohepta[def]cyclopenta[a]fluoren-4(5H)-one comprising any one of the following procedures:
  (a) dissolving free base or a hydrate of (R)-2-fluoro-10a-methyl-7,8,9,10,10a,11-hexahydro-5,6,7a,11-tetraazacyclohepta[def]cyclopenta[a]fluoren-4(5H)-one in a solvent or a solvent mixture to form a solution or a suspension; and precipitating out (R)-2-fluoro-10a-methyl-7,8,9,10,10a,11-hexahydro-5,6,7a,11-tetraazacyclohepta[def]cyclopenta[a]fluoren-4(5H)-one sesqui-hydrate in a crystalline form;
  (b) dissolving or suspending (R)-2-fluoro-10a-methyl-7,8,9,10,10a,11-hexahydro-5,6,7a,11-tetraazacyclohepta[def]cyclopenta[a]fluoren-4(5H)-one hydrate in a solvent or a solvent mixture; and precipitating out (R)-2-fluoro-10a-methyl-7,8,9,10,10a,11-hexahydro-5,6,7a,11-tetraazacyclohepta[def]cyclopenta[a]fluoren-4(5H)-one hydrate in a crystalline form with an anti-solvent;
  (c) storing a crystalline (R)-2-fluoro-10a-methyl-7,8,9,10,10a,11-hexahydro-5,6,7a,11-tetraazacyclohepta[def]cyclopenta[a]fluoren-4(5H)-one solvate/hydrate for an extended period to obtain a crystalline form;
  (d) heating a crystalline or an amorphous (R)-2-fluoro-10a-methyl-7,8,9,10,10a,11-hexahydro-5,6, 7a,11-tetraazacyclohepta[def]cyclopenta[a]fluoren-4(5H)-one to an elevated temperature, and cooling to obtain a crystalline form; and
  (e) exposing a crystalline or an amorphous (R)-2-fluoro-10a-methyl-7,8,9,10,10a,11-hexahydro-5,6,7a,11-tetraazacyclohepta[def]cyclopenta[a]fluoren-4(5H)-one to a vapor of a solvent to obtain a crystalline form.

11. The method of claim 10, wherein:
  (i) the procedure (a) or (b) further comprises one or more procedures independently selected from heating, filtering to remove undissolved impurities, distilling solvent, adding a counter solvent or solvent mixture, adding crystal seeds, adding precipitation inducing agent(s), cooling, precipitating, or filtering to collect the crystalline product;
  (ii) the procedure (a) or (b), wherein the solvent or the solvent mixture is selected from the group consisting of water, lower alkyl alcohols, ketones, ethers, esters, lower aliphatic carboxylic acids, lower aliphatic nitriles, optionally halogenated aromatic solvents, and combinations thereof;
  (iii) the solvent is isopropanol, ethanol, methanol, acetone, THF, 1,4-dioxane, acetic acid, acetonitrile, water, or a combination thereof;
  (iv) the free base is an isolated and purified free base, an isolated but unpurified free base, or a crude reaction product containing the free base;
  (v) the procedure (c), wherein said extended period is at least three days, at least one week, or at least two weeks;
  (vi) the procedure (d), wherein said elevated temperature is at least 40° C., at least 60° C., at least 80° C., or at least 100° C., but lower than decomposition temperature of the sesqui-maleate salt; or
  (vii) the procedure (e), wherein the vapor is a vapor of acetic acid.

12. The method of claim 11,
  (i) comprising the procedure (a) or (b), wherein the solvent or solvent mixture is selected from the group consisting of water, lower alkyl alcohols, ketones, ethers, esters, lower aliphatic carboxylic acids, lower aliphatic nitriles, optionally halogenated aromatic solvents, and combinations thereof; or
  (ii) wherein the solvent is isopropanol, ethanol, methanol, acetone, THF, 1,4-dioxane, acetic acid, acetonitrile, water, or a combination thereof.

13. The method of claim 10, wherein:
  1) said procedure (a) or (b) using isopropanol-water (v/v=20/40) as the solvent to produce Crystalline Form C**;
  2) said procedure (a) or (b) using MTBE as the solvent to produce Crystalline Form B;
  3) said procedure (a) or (b) using i-PrOH/H$_2$O as the solvent to produce Crystalline Form C or C*;
  4) said procedure (c) adding toluene into HOAc as the solvent to produce Crystalline Form D;
  5) said procedure (d) letting Crystalline Form A interact with DMA vapor to produce Crystalline Form E;
  6) said procedure (e) letting Crystalline Form A interact with acetic acid vapor to produce Crystalline Form F;
  7) said procedure (d) subjects Crystalline Form A to a desorption and adsorption cycle in DVS (dynamic vapor sorption) to produce Crystalline Form G;
  8) said procedure (d) heating Crystalline Form E to 80° C. to produce Crystalline Form H;
  9) said procedure (d) heating Crystalline Form E to 150° C. to produce Crystalline Form I;
  10) said procedure (d) heating Crystalline Form A to 150° C. to produce Crystalline Form J;
  11) said procedure (e) letting Crystalline Form A interact with MeOH vapor to produce Crystalline Form K;
  12) said procedure (d) heating Crystalline Form K to 150° C. to produce Crystalline Form L.

14. A pharmaceutical composition comprising a therapeutically effective amount of the compound of claim 1 and a pharmaceutically acceptable carrier.

15. A method of treating cancer in a patient, comprising administering to said patient a therapeutically effective amount of the compound of claim 1, wherein the cancer is selected from BRCA1 and BRCA2 mutant breast and or ovarian cancer.

16. The method of claim 15, wherein the compound of claim 1 is administered to the patient at a dose in the range of 1-320 mg/day, 2.5-320 mg/day, or 5-240 mg/day, and the administration frequency is one to three times a day.

17. The method of claim 15, wherein said compound is (R)-2-fluoro-10a-methyl-7,8,9,10,10a,11-hexahydro-5,6,7a,11-tetraazacyclohepta[def]cyclopenta[a]fluoren-4(5H)-one free base in a crystalline form selected from the group consisting of Crystalline Forms A, B, C, C*, C**, D, E, F, G, H, I, J, K and L.

18. A process for preparing a crystalline (R)-2-fluoro-10a-methyl-7,8,9,10,10a,11-hexahydro-5,6,7a,11-tetraazacyclohepta[def]cyclopenta[a]fluoren-4(5H)-one sesqui-hydrate of claim 3 comprising mixing (R)-2-fluoro-10a-methyl-7,8,9,10,10a,11-hexahydro-5,6,7a,11-tetraazacyclohepta[def]cyclopenta[a]fluoren-4(5H)-one free base in a mixed solvent of i-PrOH and H$_2$O at about 80° C. to provide a mixture.

19. The process off claim 18, further comprising adding crystal seeds into the mixture after cooling to room temperature, and letting the mixture stand for a certain duration.

20. The process of claim 18, wherein the mixing is performed with stirring.

21. The compound of claim 2, wherein the compound is in a crystalline form.

22. A method for preparing Crystalline Form C of claim 6 comprising:
   (i) reacting (R)-2-fluoro-10a-methyl-7,8,9,10,10a,11-hexahydro-5,6,7a,11-tetraazacyclohepta[def]cyclopenta[a]fluoren-4(5H)-one free base (Compound A) with a resolving agent in an appropriate solvent in the presence of an alkaline to provide a crude Compound A; and
   (ii) recrystallizing the crude Compound A from step (i) in a mixed solvent to obtain Crystalline Form C.

23. The compound of claim 2, having a powder X-ray diffraction pattern substantially similar to a pattern selected from the group consisting of FIGS. 4, 5, 6, 7A, 7B, and/or 11.

* * * * *

UNITED STATES PATENT AND TRADEMARK OFFICE
CERTIFICATE OF CORRECTION

PATENT NO.         : 10,457,680 B2
APPLICATION NO.    : 15/753993
DATED              : October 29, 2019
INVENTOR(S)        : Hexiang Wang et al.

Page 1 of 1

It is certified that error appears in the above-identified patent and that said Letters Patent is hereby corrected as shown below:

In the Claims

In Claim 6, at Column 42, Line 60, please replace:
"2±0.2, 21.5±0.2, 22.3±0.2, 22.7±0.2, 23.4±0.2, 23.8±0.2,"
With:
-- 21.2±0.2, 21.5±0.2, 22.3±0.2, 22.7±0.2, 23.4±0.2, 23.8±0.2, --.

In Claim 10, at Column 43, Lines 36-40, please replace:
"(d) heating a crystalline or an amorphous (R)-2-fluoro-10a-methyl-7,8,9,10,10a,11-hexahydro-5,6,7a,11-tetraazacyclohepta[def]cyclopenta[a]fluoren-4(5H)-one to an elevated temperature, and cooling to obtain a crystalline form; and"
With:
-- (d) heating a crystalline or an amorphous (R)-2-fluoro-10a-methyl-7,8,9,10,10a,11-hexahydro-5,6,7a,11-tetraazacyclohepta[def]cyclopenta[a]fluoren-4(5H)-one to an elevated temperature, and cooling to obtain a crystalline form; and --.

Signed and Sealed this
Fifth Day of May, 2020

Andrei Iancu
*Director of the United States Patent and Trademark Office*